US011701372B2

(12) United States Patent
Ellis et al.

(10) Patent No.: US 11,701,372 B2
(45) Date of Patent: Jul. 18, 2023

(54) INHALATION FORMULATIONS OF 1'-CYANO SUBSTITUTED CARBA-NUCLEOSIDE ANALOGS

(71) Applicant: Gilead Sciences, Inc., Foster City, CA (US)

(72) Inventors: Scott Ellis, San Carlos, CA (US); Davin S. Rautiola, Pacifica, CA (US); Dustin S. Siegel, Half Moon Bay, CA (US); Maria M. Toteva, South San Francisco, CA (US); Adelle A. Vandersteen, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 82 days.

(21) Appl. No.: 17/222,125

(22) Filed: Apr. 5, 2021

(65) Prior Publication Data

US 2021/0330685 A1 Oct. 28, 2021

Related U.S. Application Data

(60) Provisional application No. 63/160,622, filed on Mar. 12, 2021, provisional application No. 63/033,679, filed on Jun. 2, 2020, provisional application No. 63/022,290, filed on May 8, 2020, provisional application No. 63/005,724, filed on Apr. 6, 2020.

(51) Int. Cl.
| | |
|---|---|
| *A61K 31/685* | (2006.01) |
| *A61P 31/14* | (2006.01) |
| *A61K 9/00* | (2006.01) |
| *A61K 9/19* | (2006.01) |
| *A61K 31/675* | (2006.01) |
| *A61K 47/40* | (2006.01) |

(52) U.S. Cl.
CPC .......... *A61K 31/685* (2013.01); *A61K 9/0019* (2013.01); *A61K 9/0078* (2013.01); *A61K 9/19* (2013.01); *A61K 31/675* (2013.01); *A61K 47/40* (2013.01); *A61P 31/14* (2018.01)

(58) Field of Classification Search
CPC .................................................. A61K 31/685
USPC ......................................................... 514/80
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Natjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |

(Continued)

FOREIGN PATENT DOCUMENTS

| | | |
|---|---|---|
| CN | 110330540 | 10/2019 |
| CN | 110776512 | 2/2020 |

(Continued)

OTHER PUBLICATIONS

Bobrowski et al., "Synergistic and Antagonistic Dmg Combinations against SARS-CoV-2", Molecular Therapy, Feb. 2021, 29(2):873-885.

Grein et al., "Compassionate Use of Remdesivir for Patients with Severe Covid-19", The New England Journal of Medicine, Apr. 2020, 382(24): 2327-2336.

Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.

Sun, "Remdesivir for Treatment of COVID-19: Combination of Pulmonary and IV Administration May Offer Additional Benefit", The AAPS Journal, 2020, 22(77):1-6.

(Continued)

*Primary Examiner* — Taofiq A Solola
(74) *Attorney, Agent, or Firm* — Fish & Richardson P.C.

(57) ABSTRACT

The present disclosure provides pharmaceutical formulations of the compound of Formula I, Formula Ia, or Formula Ib, or a pharmaceutically acceptable salt thereof, and an aqueous vehicle. The pharmaceutical formulations of the disclosure are useful in treatment and prevention of viral infections in subjects in need thereof and are for administration by inhalation.

16 Claims, 24 Drawing Sheets

(56) References Cited

U.S. PATENT DOCUMENTS

| | | | |
|---|---|---|---|
| 8,871,737 B2 | 10/2014 | Smith et al. |
| 8,889,159 B2 | 11/2014 | Clearly et al. |
| 8,980,865 B2 | 3/2015 | Wang |
| 9,090,642 B2 | 7/2015 | Cho et al. |
| 9,243,022 B2 | 1/2016 | Beigelman et al. |
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0393653 A1 | 12/2021 | Cihlar et al. |
| 2021/0393659 A1 | 12/2021 | O'Neil et al. |
| 2021/0403497 A1 | 12/2021 | Butler et al. |
| 2022/0081462 A1 | 3/2022 | Chun et al. |
| 2022/0175805 A1 | 6/2022 | Cihlar |
| 2022/0280549 A1 | 9/2022 | Larson et al. |
| 2022/0354873 A1 | 11/2022 | Axt et al. |

FOREIGN PATENT DOCUMENTS

| | | | |
|---|---|---|---|
| CN | 111548384 A | * | 3/2020 |
| CN | 111171078 | | 5/2020 |
| CN | 111205294 | | 5/2020 |
| CN | 111205327 | | 5/2020 |
| CN | 111233869 | | 6/2020 |
| CN | 111265532 | | 6/2020 |
| CN | 111440176 | | 7/2020 |
| CN | 111548384 | | 8/2020 |
| CN | 111961057 | | 11/2020 |
| CN | 202011613943.3 | | 12/2020 |
| CN | 112778310 | | 5/2021 |
| CN | 202110562244.9 | | 5/2021 |
| CN | 113754665 | | 6/2021 |
| CN | 113185519 | | 7/2021 |
| CN | 113292565 | | 8/2021 |
| CN | 113387954 | | 9/2021 |
| CN | 113735862 | | 9/2021 |
| CN | 114292272 | | 12/2021 |
| CN | 114437159 | | 5/2022 |
| IN | 202134041493 | | 9/2021 |
| IN | 202011021676 | | 11/2021 |
| JP | 2005185235 | | 7/2005 |
| JP | 2005187428 | | 7/2005 |
| WO | WO1991019721 | | 12/1991 |

(56) References Cited

FOREIGN PATENT DOCUMENTS

| | | |
|---|---|---|
| WO | WO1999045029 | 9/1999 |
| WO | WO2000056734 | 9/2000 |
| WO | WO200075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046159 | 6/2004 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017165489 | 9/2017 |
| WO | WO2017184668 | 10/2017 |
| WO | WO2018085307 | 5/2018 |
| WO | WO2018121678 | 7/2018 |
| WO | WO2018145148 | 8/2018 |
| WO | WO2018204198 | 11/2018 |
| WO | WO2019014247 | 1/2019 |
| WO | WO2019053696 | 3/2019 |
| WO | WO2022098371 | 11/2020 |
| WO | WO2021021717 | 2/2021 |
| WO | WO2021040356 | 3/2021 |
| WO | WO2021050961 | 3/2021 |
| WO | WO2021147236 | 7/2021 |
| WO | WO2021175296 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2022143473 | 12/2021 |
| WO | WO2022029704 | 2/2022 |
| WO | WO2022047065 | 3/2022 |
| WO | WO2022047441 | 3/2022 |
| WO | WO2022165386 | 8/2022 |
| WO | WO2022174194 | 8/2022 |
| WO | WO2022217153 | 10/2022 |
| WO | WO2022217154 | 10/2022 |
| WO | WO2022217155 | 10/2022 |
| WO | WO2022251663 | 12/2022 |

OTHER PUBLICATIONS

Adlington et al., "Synthesis of novel C-nucleosides with potential applications in combination and parallel synthesis," Tetrahedron Letters, 2000, 41:575-578.

Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.

Huang et al., "Recent development of therapeutics for chronic HCV infection," Antiviral Research, Sep. 2006, 71(2-3): 351-362.

Kushner et al., "Pharmacological uses and perspectives of heavy water and deuterated compounds," Canadian Journal of Physiology and Pharmacology, Feb. 1999, 77(2):79-88.

Martin et al., "Hint2, A Mitochondrial Apoptotic Sensitizer Down-Regulated in Hepatocellular Carcinoma," Gastroenterology, Jun. 2006, 130(7):2179-2188.

(56) References Cited

OTHER PUBLICATIONS

Sahakijpijam et al., "Development of Remdesivir as a Dry Powder for Inhalation by Thin Film Freezing," Pharmaceutics, Oct. 2020, 12(11):1002, 27 pages.
Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.
Shi et al., "Synthesis and anti-viral activity of a series of d- and l-2'-deoxy-2'-fluororibonucleosides in the subgenomic HCV replicon system," Bioorganic & Medicinal Chemistry, Mar. 2005, 13(5): 1641-1652.
Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.
Stein et al., "Phosphorylation of Nucleoside Analog Antiretrovirals: A Review for Clinicians," Pharmacotherapy, Jan. 2001, 21(1):11-34.
Stella et al., "Cyclodextrins," Toxicologic Pathology, 2008, 36(1):30-42.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Xie et al., "Weinreb Amide Approach to the Practical Synthesis of a Key Remdesivir Intermediate," The Journal of Organic Chemistry, 2021, 86:5065-5072.
PCT International Search Report and Written Opinion in International Application No. PCT/US2021/025719, dated Sep. 29, 2021, 15 pages.
Taiwanese Office Action in TW Patent Application No. 110112444, dated Jan. 24, 2022, 15 pages (with English translation).
Beer et al., "Characteristics of Filoviridae: Marburg and Ebola Viruses," Naturwissenschaften, 1999, 86:8-17.
Brands et al., "Crystallization-Induced Diastereomer Transformations," Chem. Rev., 2006, 106(7):2711-2733.
Brotschi et al., "Bipyridyl and biphenyl DNA: A recognition motif based on interstrand aromatic stacking," Chemistty—A European Journal, 2005, 11(6):1911-1923.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Leyssen et al., "Molecular strategies to inhibit the replication of RNA Viruses," Antiviral Research, 2008, 78:9-25.
McGuigan et al., "Design, synthesis and biological evaluation of phosphorodiamidate prodrugs of antiviral and anticancer nucleosides," European Journal of Medical Chemistry, 2013, 70:326-340.
Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940): 1-16.
Sheahan et al., "Comparative therapeutic efficacy of remdesivir and combination lopinavir, ritonavir, and interferon beta against MER-CoV," Nature Communications, 2020, 11(222): 1-14.
Tschesnokov et al., "Template-dependent inhibition of coronavirus RNA-dependent RNA polymerase by remdesivir reveals a second mechanism of action," J. Biol. Chem., 2020, 295(47): 16156-16165.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Bowie et al., "RIG-I: tri-ing to discriminate between self and non-self RNA," Trends in Immunology, Apr. 2007, 28(4): 147-150.

Cox et al., "Therapeutically administered ribonucleoside analogue MK-4482/EIDD-2801 blocks SARS-CoV-2 transmission in ferrets," Nature Microbiology, 2020, 6(1): 11-18.
Dinnon et al., "A mouse-adapted model of SARS-CoV-2 to test COVID-19 countermeasures," Nature, Aug. 2020, 586: 560-566.
Flint et al., "Functional analysis of cell surface-expressed hepatitis C virus E2 glycoprotein," J. Virol., Aug. 1999, 73(8): 6782-6790.
Freeman et al., "3 Prodrug Design for Phosphates and Phosphonates," Progress in Medicinal Chemistry, 1997, 34: 111-147.
Pelet et al., "High throughput screening assay for negative single stranded RNA virus polymerase inhibitors," J. Virol. Methods, Sep. 2005, 128(1-2): 29-36.
Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.
Vermillion et al., "Inhaled remdesivir reduces viral burden in a nonhuman primate model of SARS-CoV-2 infection," Science Translation Medicine, Dec. 2021, 20 pages.
Wang et al., "ANNOVAR: functional annotation of genetic variants from high-throughput sequencing data," Nucleic Acids Research, 2010, 38(16): e!64, 7 pages.
Wolfel et al., "Virological assessment of hospitalized patients with COVID-2019," Nature, Apr. 2020, 581: 465-470.
Yoon et al., "High-throughput screening-based identification of paramyxovims inhibitors," J. Biomol. Screen., Aug. 2008, 13(7): 591-608.
Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.
Alessandrini, et al., Synthesis of Differently Protected 1-C-methyl-ribofuranoses Intermediates for the Preparation of Biologically Active 1'-C-methyl-ribonucleosides, Journal of Carbohydrate Chemistiy, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Anonymous, "Gillings research on broad-spectrum antiviral could aid public health response to coronavirus outbreaks", -UNC Gillings School of Global Public Health, Jan. 10, 2020, retrieved on May 13, 2021, revrieved from URL <"https://sph.unc.edu/sph-news/gillings-research-on-broad-spectrum-antiviral-could-aid-public-health-response-to-coronavirus-outbreaks/">, 5 pages.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Ballini, et al., Enantio selective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of Feline (FIPV) and Human (SARS) Coronavims by Semisynthetic Derivatives of Glycopeptide Antibiotics, Antiviral Research, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistiy, 1961, pp. 4605-4609, vol. 26, No. 11.
Barl, et al., The halogen/magnesium-exchange using iPrMgCl•LiCl and related exchange reagents, Heterocycles, Jan. 2014, pp. 827-844, vol. 88, No. 2.
Belokon, et al., Optimized catalysts for the asymmetric addition of trimethylsilyl cyanide to aldehydes and ketones, Tetrahedron, 2001, pp. 771-779, vol. 57.
Benksim, et al., A Novel Stereospecific Synthesis of Glycosyl Cyanides from 1,2-O-sulfinyl Derivatives, Organic Letters, 2004, pp. 3913-3915, vol. 6, No. 22.

(56) References Cited

OTHER PUBLICATIONS

Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.
Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, et al., Design and Synthesis of Inhibitors of Adenosine and AMP Deaminases, Organic Letters, 2001, pp. 839-842, vol. 3, No. 6.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
Brittain, Polymorphism in Pharmaceutical Solids, 2nd Edition, 2009, pp. 183-226, Informa Healthcare USA, Inc.
Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.
Brown, Progress towards improving antiviral therapy for hepatitis C virus polymerase inhibitors. Part O: Nucleoside analogues, 2009, pp. 709-725, vol. 18.
Bullard-Feibelman, et al., The FDA-approved drug Sofosbuvir inhibits Zika Virus infection, Antiviral Res., Jan. 1, 2018, pp. 134-140, vol. 137.
Burns, A Glimmer of Hope for Fatal Feline Disease, JAVMAnews, Dec. 15, 2017, 5 pages.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.
Cabirol, et al., Robust and Efficient, yet Uncatalyzed, Synthesis of Triarylsilyl-protected Cyanohydrins from Ketones, 2008, pp. 2446-2449, vol. 73.
Caira, Crystalline Polymorphism of Organic Compounds, Topics in Current Chemistry, 1998, pp. 163-208, vol. 198.
Calès, et al., Treatment of liver fibrosis: clinical aspects, Gastroenterologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple -αβ-butenolides-II, Tetrahedron, 1982, pp. 2395-2402, vol. 38, No. 15.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.

CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.
Chapman, et al., RSV604, a Novel Inhibitor of Respiratory Syncytial Virus Replication, Antimicrobial Agents and Chemotherapy, 2007, pp. 3346-3353, vol. 51, No. 9.
Cho, et al., "Synthesis and antiviral Activity of a Series of 1'-Substituted 4-aza-7,9-dideazaadenosine C-Nucleosides", Bioorganic & Medicinal Chemistry Letters, 2012, 22:2705-2707.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Clarke, et al., Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases, Bioorganic & Medicinal Chemistry Letters, Apr. 29, 2015, pp. 2484-2487, vol. 25.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Dai, et al., Synthesis of 2'-C-β-Fluoromethyluridine, Organic Letters, 2003, pp. 807-810, vol. 5, No. 6.
Damont et al., "Synthesis of 1'-C-Fluoromethyladenosine," Nucleosides, Nucleotides, and Nucleic Acids, 2007, 26:1431-1434.
De Clercq, Antiviral Drugs: Current State of the Art, J. Clin. Virol., 2001, pp. 73-89, vol. 22, No. 1.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.2 4.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4-f][1,2,4]triazines as Inhibitors of Adenosine and AMP Deaminasses, J. Chem. Soc., Perkin Trans. 1, 1999, pp. 2937-2942.
Dudfield, P. et al., Synthesis of C-ribosyl imidazo[2,1-f][1,2,4]triazines as inhibitors of adenosine and AMP deaminases, J. Chem. Soc, Perkin Trans I, 1999, pp. 2929-2936.

(56) References Cited

OTHER PUBLICATIONS

Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Dymock, et al., Novel approaches to the treatment of hepatitis C virus infection, Antiviral Chemistry & Chemotherapy, 2000, pp. 79-96, vol. 11, No. 2.
El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
Farquhar, et al., Biologically Reversible Phosphate-Protective Groups, Journal of Pharmaceutical Sciences, 1983, pp. 324-325, vol. 72, No. 3.
Fauquet et al., "Abbreviations for vertebrate virus species names", Archives of Virology, Dec. 31, 1999, pp. 1865-1880.
Foster et al., "Deuterium isotope effects in studies of drug metabolism," Trends in Pharmacological Sciences, Jan. 1984, 5:524-527.
Franchetti et al., Antitumor Activity of C-Methyl-β-D-ribofuranosyladenine Nuceoside Ribonuceotide Reductase Inhibitors, J. Med. Chem. 2005, pp. 4983-4989, vol. 48.
Fukumoto, et al., Viral Dynamics of Hepatitis C Early After Orthotopic Liver Transplantation: Evidence for Rapid Turnover of Serum Virions, Hepatology, 1996, pp. 1351-1354, vol. 24.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
George et al., "Preparation of silyl-and germylmetallic compounds," Journal of the American Chemical Society, Jan. 1960, 82(2):403-6.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, et al., Protective Groups in Organic Synthesis, 1991, pp. 118-142, John Wiley & Sons.
Greene, T.W. and Wuts, P.G.M. (1991) Protective Groups in Organic Synthesis, published by John Wiley & Sons,v Inc., p. 1-4, 10-14, 47-53 and 100-103.
Gudmundsson, et al., Synthesis of imidazo[1,2-a]pyridine C-Nucleosides with an Unexpected Site of Ribosylation, Journal of Organic Chemistiy, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.
Gunic, et al., Cyclic monophosphate prodmgs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy- and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, K. et al., Stereoselective Synthesis of 1'-C-Branched Uracil Nucleosides From Uridine, Nucleosides & Nucleotides, 1995, pp. 417-420, vol. 14, No. 3-5.

Harcourt, et al., Molecular Characterization of the Polymerase Gene and Genomic Termini of Nipah Virus, Virology, 2001, pp. 192-201, vol. 287.
Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.
Hayashi, et al., C-Nucleosides, A Synthesis of 2-Substituted 7-(b-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.
Hecker, et al., Liver Targeted Prodmgs of 2'-C-Methyladenosine for Therapy of Hepatitis C Vims Infection, J. Med. Chem., 2007, pp. 3891-3896, vol. 50, No. 16.
Hoffmann, et al., "When, in the context of drug design, can a fluorine atom successfully substitute a hydroxyl group?", International Journal of Quantum Chemistry, 2002, pp. 419-427, vol. 89.
Holshue et al., "First Case of 2019 Novel Coronavirus in the United States", The New England Journal of Medicine, Jan. 2020, 9 pages.
Itoh, et al., Divergent and Stereocontrolled Approach to the Synthesis of Uracil Nucleosides Branched at the Anomeric Position, J. Org. Chem., 1995, pp. 656-662, vol. 60.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.
Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.
Kaewkhao et al., "High sensitivity methods to quantify chloroquine and its metabolite in human blood samples using LC-MS/MS", Bioanalysis, Mar. 2019, 11(5):333-347.
Kalil et al., "Baricitinib plus Remdesivir for hospitalized adults with Covid-19," New England Journal of Medicine, Dec. 11, 2020, 13 pages.
Khamnei, et al., Neighboring Group Catalysis in the Design of Nucleotide Prodmgs, J. Med. Chem., 1996, pp. 4109-4115, vol. 39, No. 20.
Kim, et al., Reversal of the Progression of Fatal Coronavims Infection in Cats by a Broad-Spectrum Coronavims Protease Inhibitor, PLOS Pathogens, Mar. 30, 2016, 18 pages.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistiy, 2006, pp. 3793-3799, vol. 281, No. 7.
Knaggs, et al., A QSAR Study Investigating the Effect of L-Alanine Ester Variation on the Anti-HIV Activity of Some Phosphoramidate Derivatives of d4T, 2000, pp. 2075-2078.
Knutsen, et al., Synthesis of Imidazo-fused Bridgehead-nitrogen C-Nucleosides : Coupling-Elimination Reactions of 2,5-Anhydro-3,4,6-tri-O-benzoyl-D- allonic Acid, J. Chem. Soc. Perkin Trans I, 1985, pp. 621-630.
Knutsen, et al., Synthesis of Imidazo-fused Bridgehead-nitrogen C-Nucleosides via Dehydrative Coupling Reactions of 2,5-Anhydro-3,4,6-tri-O-benzoyl-D- allonic Acid, J. Chem. Soc. Perkin Trans I, 1984, pp. 229-238.
Kobe, et al., Use of Distance Geometry Approach for the In Vitro Antiviral Activity Evaluation of N-bridgehead C-nucleosides, European J. Med. Chem., 1992, pp. 259-266, vol. 27, No. 3.
Kuzik et al., "Nebulized Hypertonic Saline in the Treatment of Viral Bronchiolitis in Infants", The Journal of Pediatrics, Sep. 2007, 151(3):266-270.e1.
Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.

(56) References Cited

OTHER PUBLICATIONS

Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.
Lo et al., "GS-5734 and its parent nucleoside analog inhibit Filo-, Pneumo-, and Paramyxoviruses," Scientific Reports, 2017, 7(43395): 1-7.
Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.
Lu, Chengping, Veterinary Microbiology 5th edition, Jan. 31, 2013, p. 431, China Agriculure Press (No English Translation available).
Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.
Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.
Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.
Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.
McGuigan, et al. Application of Phosphoramidate ProTide Technology Significantly Improves Antiviral Potency of Carbocyclic Adenosine Derivatives, 2006, pp. 7215-7226.
McGuigan, et al., Aryl Phosphoramidate Derivatives of d4T Have Improved Anti-HIV Efficacy in Tissue Culture and May Act by the Generation of a Novel Intracellular Metabolite, J. Med. Chem., 1996, pp. 1748-1753, vol. 39.
McGuigan, et al., Intracellular Delivery of Bioactive AZT Nucleotides by Aryl Phosphate Derivatives of AZT, J. Med. Chem., 1993, pp. 1048-1052, vol. 36, No. 8.
Mehellou, et al., Aryloxy Phosphoramidate Triesters: a Technology for Delivering Monophosphorylated Nucleosides and Sugars into Cells, ChemMedChem, 2009, pp. 1779-1791, vol. 4.
Meppen, et al., Cyclic phosphoramidates as prodrugs of 2'-C-methylcytidine, European Journal of Medicinal Chemistiy, 2009, pp. 3765-3770, vol. 49, No. 9.
Meppen, et al., Medi-404—A Prodrug Approach for the Treatment of HCV Infection, Abstracts of papers, 236th ACS National Meeting, Philadelphia, PA, United States, Aug. 17-21, 2008.
Metobo, et al., Practical synthesis of 1'-substituted Tubercidin C-nucleoside analogs, Tetrahedron Letters, Feb. 2012, pp. 484-486, vol. 53, No. 5.
Migliaccio, et al., Characterization of Resistance to Non-obligate Chain-terminating Ribonucleoside Analogs That Inhibit Hepatitis C Virus Replication in vitro, The Journal of Biological Chemistiy, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Morris, "Mechanisms of action and therapeutic role of corticosteroids in asthma", J. Allergy Clin. Immunol., Januaiy 1985, 75(1 Pt): 1-13.

Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.
Mossel et al., "Exogenous ACE2 expression allows refractory cell lines to support severe acute respiratoiy syndrome coronavirus replication," Journal of Virology, Mar. 15, 2005, 79(6):3846-50.
Munster et al., "Hydroxychloroquine concentration-response relationships in patients with rheumatoid arthritis", Arthritis Rheumatology, Jun. 2002, 46(6)4460-1469.
Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.
Murakami, et al., Mechanism of Activation of PSI-7851 and Its Diastereoisomer PSI-7977, The Journal of Biological Chemistiy, 2010, pp. 34337-34347, vol. 285, No. 45.
Murphy, et al., The Nucleoside Analog GS-441524 Strongly Inhibits Feline Infectious Peritonisitis (FIP) Virus in Tissue Culture and Experimental Cat Infection Studies, Veterinary Microbiology, 2018, pp. 226-233, vol. 219.
Neumann, et al., Hepatitis C Viral Dynamics in Vivo and the Antiviral Efficacy of Interferon-α Therapy, Science, 1998, pp. 103-107, vol. 282.
Nishimura, et al., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.
Ogura, et al., Reaction of Ethynyl Compounds with Lactones, Journal of Organic Chemistry, 1972, pp. 72-75, vol. 37, No. 1.
Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.
Otter, B. et al., Conformational Properties of Purine-Like C-Nucleosides, Nucleosides & Nucleotides, 1996, pp. 793-807, vol. 15, No. 1-3.
Pankiewicz, et al., C-Nucleoside Analogues of Nicotinamide Mononucleotide (NMN), Nucleosides and Nucleotides, 1988, pp. 589-593, vol. 7, No. 5&6.
Pankiewicz, et al., Efficient Synthesis of 5-(β-D-Ribofuranosyl)nicotinamide and its α-Isomer, Journal of Organic Chemistiy, 1988, pp. 3473-3479, vol. 53.
Patani et al., "Bioisosterism: a rational approach in drug design," Chem. Rev., 1996, 96:3147-3176.
Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.
Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.
Patil, et al., Synthesis of some new thieno[3,4-d]pyrimidines and their C-nucleosides, Journal of Heterocyclic Chemistiy, 1993, pp. 509-515, vol. 30, No. 2.
Patil, S. et al., 4-Aza-7,9-Dideazaadenosine, a New Cytotoxic Synthetic C-Nucleoside Analogue of Adenosine, Tetrahedron Letters, 1994, pp. 5339-5342, vol. 35, No. 30.
Perrone, et al., Application of the Phosphoramidate ProTide Approach to 4'-Azidouridine Confers Sub-micromolar Potency versus Hepatitis C Virus on an Inactive Nucleoside, Journal of Medicinal Chemistry, 2007, pp. 1840-1849, vol. 50, No. 8.
Peterson, et al., Prodrug approaches to improving the oral absorption of antiviral nucleotide analogues, Expert Opinion, Drug Deliv., 2009, pp. 405-420, vol. 6, No. 4.
Piccirilli, et al., A Direct Route to 3-(D-Ribofuranosyl)pyridine Nucleosides, Helvetica Chimica Acta, 1991, pp. 397-406, vol. 74.
Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.
Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.

(56) References Cited

OTHER PUBLICATIONS

Porter, et al., Zika virus, drug discovery, and student projects, ScienceBlogs, Mar. 9, 2016, 7 pages.

Puech, et al., Intracellular Delivery of Nucleoside Monophosphates through a Reductase-mediated Activation Process, Antiviral Research, 1993, pp. 155-174, vol. 22, No. 4.

Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.

Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.

Reddy, et al., Stereoselective Synthesis of Nucleoside Monophosphate HepDirectTM Prodrugs, Tet. Lett., 2005, pp. 4321-4324, vol. 46.

Ross, et al., Synthesis of Diastereomerically Pure Nucleotide and Phosphoramidates, J. Org. Chem., 2011, pp. 8311-8319, vol. 76.

Sacramento, et al., The clinically approved antiviral drug Sofosbuvir inhibits Zika Virus replication, Nature, Jan. 18, 2017.

Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.

Schultz, Prodrugs of Biologically Active Phosphate Esters, Bioorganic & Medicinal Chemistry, 2003, pp. 885-898, vol. 11.

Scott, et al., Interferon-a-2b Plus Ribavirin: A Review of its Use in the Management of Chronic Hepatitis C, Drugs, 2002, pp. 507-556, vol. 62, No. 3.

Sheahan et al., "Broad-spectrum antiviral GS-5734 inhibits both epidemic and zoonotic coronaviruses", Science Translational Medicine, Jun. 2017, 9(396):eaa13653, 11 pages.

Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.

Shekunov, et al., Crystallization processes in pharmaceutical technology and drug delivery design, Journal of Crystal Growth, 2000, pp. 122-136, vol. 211.

Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.

Siegel, et al., Discovery and Synthesis of a Phosphoramidate Prodrug of a Pyrrolo[2,1-f][triazin-4-amino] Adenine C-Nucleoside (GS-5734) for the Treatment of Ebola and Emerging Viruses, J. Med. Chem., 2017, 60, 5, 1648-1661 Supplementary Material.

Silverman et al., The Organic Chemistry of Drug Design and Drug Action, 1992, pp. 19-23.

Silverman, The Organic Chemistry of Drug Design and Drug Action, 2nd Ed., 2004, pp. 29-34.

Srivastav, et al., Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus(HBV) Replication, Journal of Medicinal Chemistry, 2010, pp. 7156-7166, vol. 53, No. 19.

Tapia, et al., Combination of a Mutagenic Agent with a Reverse Transcriptase Inhibitor Results n Systematic Inhibition of HIV-1 Infection, Virology, 2005, pp. 1-8, vol. 338.

Totura et al., "Broad-spectrum coronavirus antiviral drug discovery", Expert Opinion on Drug Discovery, Mar. 2019, 17 pages.

Towner, et Al., Newly Discovered Ebola Virus Associated with Hemorrhagic Fever Outbreak in Uganda, PLoS Pathogens, 2008, 6 pages, vol. 4, Issue 11.

Uchiyama, et al., O-selective Phosphorylation of Nucleosides without N-protection, J. Org. Chem., Jan. 1, 1993, vol. 58, No. 2.

Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.

Venkatachalam, et al. Effect of change in nucleoside structure on the activation and antiviral activity of phosphoramidate derivatives, 2005, pp. 5408-5423.

Walker et al., "Plasma chloroquine and desethylchloroquine concentrations in children during and after chloroquine treatment for malaria.", British Journal Clinical Pharmacology, Dec. 1983, 16(6):701-705.

Wang et al., "Remdesivir and chloroquine effectively inhibit the recently emerged novel coronavirus (2019-nCoV) in vitro", Cell Research, 2020, 30:269-271.

Warren et al., "Protection against filovirus diseases by a novel broad-spectrum nucleoside analogue BCX4430", Nature, Apr. 2014, 508(7496):402-405.

Warren, et al., Therapeutic efficacy of the small molecules GS-5734 against EBOLA virus in rhesus monkeys, Nature, Mar. 17, 2016, 19 pages.

Wu, et al., Synthetic Methodologies for C-Nucleosides, Synthesis, 2004, pp. 1533-1553, vol. 10.

Xie et al., "A nanoluciferase SARS-CoV-2 for rapid neutralization testing and screening of anti-infective drugs for COVID-19," Nature Communications, Oct. 15, 2020, 11(1): 1-1.

Yamanaka, et al., Metabolic Studies on BMS-200475, a New Antiviral Compound Active against Hepatitis B Virus, Antimicrobial Agents and Chemotherapy, 1999, p. 190, vol. 43, No. 1.

Yates et al., "The evolution of antiviral nucleoside analogues: A review for chemists and non-chemists. PartII: Complex modifications to the nucleoside scaffold", Antiviral Research, Dec. 8, 2018, 162:5-21.

Yoshimura, et al., Synthesis and Biological Evaluation of 1'-C-Cyano-Pyrimidine Nucleosides, Nucleosides & Nucleotides, 1996, pp. 305-324, vol. 15, No. 1-3.

Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.

Zhu et al., "A novel coronavirus from patients with pneumonia in China, 2019," New England Journal of Medicine, Jan. 24, 2020, 14 pages.

ARIPO Patent Office, Form 21 and Substantive Examination Report (in English) for AP Application No. AP/P/2010/005439, dated Mar. 18, 2014.

ARIPO Patent Office, Form 21 for AP Patent Application No. AP/P/2011/005818, dated Sep. 19, 2013.

ARIPO Patent Office, Search and Exam Report for AP Application No. AP/P/2012/006189, dated Jun. 26, 2014.

ARIPO Patent Office, Search Report for AP Patent Application No. AP/P/2011/005818, dated Sep. 19, 2013.

Australia Patent Office, First Examination Report for AU Patent Application No. 2009240630, dated Jun. 14, 2012.

Australia Patent Office, Patent Examination Report No. 1 for AU Application No. 2011306066, dated Nov. 21, 2013.

Australia Patent Office, Patent Examination Report No. 1 for AU Patent Application No. 2010213873, dated Jun. 4, 2014.

Chile Patent Office, First Office Actionfor CL Patent Application No. 1906-2011, received May 7, 2013.

Chile Patent Office, Opposition for CL Patent Application No. 727-2013, dated Oct. 15, 2013.

Chile Patent Office, Second Office Action for CL Patent Application No. 1906-2011, dated Oct. 16, 2013.

Chinese Patent Office, First Examination Report for CN Patent Application No. 200980120218.8, dated Nov. 13, 2012.

Chinese Patent Office, First Office Action for CN Patent Application No. 201080011690.0, dated Jun. 8, 2013.

Chinese Patent Office, Notification of Reexamination for CN Patent Application No. 200980120218.8, dated Sep. 1, 2014,.

Chinese Patent Office, Notification of the Second Office Action & Search Report for CN Patent Application No. 201080011690.0, dated Jan. 8, 2014.

Chinese Patent Office, Notification of the Third Office Action for CN Patent Application No. 2010800116900.0, dated Jul. 29, 2014.

(56) References Cited

OTHER PUBLICATIONS

Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Columbia Patent Office, First Examination Report (in English) for CO Patent Application No. 10-131479, dated Oct. 23, 2012.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-131479, dated Sep. 27, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Ecuador Patent Office, Opposition for EC Patent Application No. SP-2012-11817, dated May 27, 2013.
El Salvador Patent Office, Official Action for SV National Phase Entry of International Application No. PCT/US2010/049471, dated Nov. 6, 2013.
Eurasian Patent Office, First Examination Report for EA Patent Application No. 201071128, dated Apr. 25, 2012.
Eurasian Patent Office, First Office Action for EA Patent Application No. 201190110/28, dated Apr. 26, 2012.
Eurasian Patent Office, First Office Action for EA Patent Application No. 201390141/28, with English translation, received Aug. 14, 2014.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Office Actionfor EA Application No. 201190110/28, dated Oct. 18, 2013.
European Patent Office, Communication pursuant to Article 94(3) EPC for EP Patent Application No. 10763083.2, dated May 2, 2014.
European Patent Office, Communication pursuant to Article 94(3) EPC for EP Patent Application No. 11715792.5, dated Feb. 14, 2014.
European Patent Office, Communication under 161/162 for EP Patent Application No. 10704068.5, dated Sep. 6, 2011.
European Patent Office, Communication under 161/162 for EP Patent Application No. 10763083.2, dated May 11, 2012.
European Patent Office, Communication under 161/162 for EP Patent Application No. 11715792.5, dated Apr. 26, 2013.
European Patent Office, First Office Action for EP Patent Application No. 10704068.5, dated Jun. 18, 2012.
Indonesia Patent Office, First Examination Report for ID Patent Application No. W00 2010 03957, dated Apr. 25, 2013.
Indonesia Patent Office, Substantive Examination Report Stage 1 for ID Application No. W-00201103126, dated Jun. 10, 2014.
Israel Patent Office, First Examination Report for IL Patent Application No. 208701, dated Jan. 13, 2013.
Israel Patent Office, First Office Action for IL Patent Application No. 214396, dated Jul. 8, 2013.
Israel Patent Office, Notification of Defects for IL Patent Application No. 214396, dated Nov. 11, 2013.
Israel Patent Office, Notification of Defects for IL Patent Application No. 218599, dated Aug. 25, 2014.
Israel Patent Office, Notification of Defects for IL Patent Application No. 208701, dated Aug. 25, 2014.
Israel Patent Office, Notification Prior to Examination for IL Patent Application No. 218599, dated Nov. 13, 2012.
Japanese Patent Office, First Examination Report for JP Patent Application No. 2011-506429, dated Aug. 22, 2013.
Japanese Patent Office, Notice of Reasons for Rejection for Japanese Patent Appln. No. JP 2017-520934, dated Mar. 30, 2018.
Japanese Patent Office, Notification of Reasons for Rejection for JP Application No. 2011-549324, dated Jul. 28, 2014.
Japanese Patent Office, Notification of Reasons for Rejection for JP Application No. 2011-549324, dated Mar. 26, 2014.
Japanese Patent Office, Notification of Reasons for Rejection for JP Patent Application No. 2012-529958, dated Aug. 5, 2014.
Mexico Patent Office, English translation of Office Action for MX Application No. MX/a/2013/003179, dated Feb. 25, 2014.
Mexico Patent Office, First Examination Report (in English) for MX Patent Application No. MX/a/2010/011661, dated Oct. 26, 2011.
Mexico Patent Office, Office Action for MX Application No. MX/a/2011/008409, dated Mar. 25, 2014.
New Zealand Patent Office, First Examination Report for NZ Patent Application No. 588670, dated Apr. 8, 2011.
New Zealand Patent Office, First Examination Report for NZ Patent Application No. 608070, dated Nov. 7, 2013.
New Zealand Patent Office, Further Examination Report for NZ Application No. 594370, dated Oct. 8, 2013.
PCT International Preliminary Report on Patentability and Written Opinion for PCT International Application No. PCT/US2009/041432, dated Oct. 26, 2010, 7 pages.
PCT International Preliminary Report on Patentability and Written Opinion for PCT International Application No. PCT/US2010/049471, dated Mar. 27, 2012, 7 pages.
PCT International Preliminary Report on Patentability and Written Opinion for PCT International Application No. PCT/US2011/038253, dated Dec. 4, 2012, 6 pages.
PCT International Preliminary Report on Patentability for PCT International Application No. PCT/US2010/023586, dated Aug. 16, 2011, 6 pages.
PCT International Preliminary Report on Patentability for PCT International Application No. PCT/US2011/028897, dated Mar. 26, 2013, 7 pages.
PCT International Preliminary Report on Patentability for PCT International Application No. PCT/US2011/029441, dated Mar. 26, 2013, 7 pages.
PCT International Preliminary Report on Patentability for PCT International Application No. PCT/US2015/057934, dated May 11, 2017, 14 pages.
PCT International Search Report and Written Opinion for PCT International Application No. PCT/US2009/041432, dated Aug. 11, 2009, 11 pages.
PCT International Search Report and Written Opinion for PCT International Application No. PCT/US2011/028897, dated Aug. 1, 2011, 6 pages.
PCT International Search Report and Written Opinion for PCT International Application No. PCT/US2011/029441, dated Aug. 1, 2011, 5 pages.
PCT International Search Report and Written Opinion for PCT International Application No. PCT/US2011/038253, dated Jul. 29, 2011, 4 pages.
PCT International Search Report and Written Opinion for PCT International Application No. PCT/US2017/028251, dated Oct. 16, 2017, 22 pages.
PCT International Search Report and Written Opinion for PCT International Application No. PCT/US2017/028251, dated Sep. 13, 2017, 22 pages.
PCT International Search Report and Written Opinion for PCT International Application No. PCT/US2010/023586, dated Aug. 4, 2010, 4 pages.
PCT International Search Report and Written Opinion for PCT International Application No. PCT/US2010/049471, dated Nov. 18, 2010, 11 pages.
Peru Patent Office, Office Action in PE Application No. 1464, dated Sep. 12, 2013.
Resolution No. 48031 for CO Patent Application No. 10-121.513, rec'd Oct. 7, 2014 (8 pages) (English translation).
Ukraine Patent Office, First Examination Report for UA Patent Application No. 2010 13030, dated Mar. 2, 2013.

(56) References Cited

OTHER PUBLICATIONS

Ukraine Patent Office, First Office Action for UA Application No. a 2011 10568, received Apr. 7, 2014.
Ukraine Patent Office, Second Office Action for UA Patent Application No. 2011 10568, dated Aug. 11, 2014.
Vietnam Patent Office, First Examination Report for VN Patent Application No. 1-2010-02939, dated Apr. 19, 2012.
Vietnam Patent Office, Second Examination Report for VN Patent Application No. 1-2010-02939, dated Jul. 26, 2012.
fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.
Khan et al., "Coronaviruses disease 2019 (COVID-19): Causative agent, mental health concerns, and potential management options," Journal of Infection and Public Health, Dec. 2020, 13(12):1840-1844.
Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.
Liu et al., "Hydroxychloroquine, a less toxic derivative of chloroquine, is effective in inhibiting SARS-CoV-2 infection in vitro," Cell Discovery, Mar. 18, 2020, 6:16, 4 pages.
Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5):121-133.
Pizzomo et al., "In vitro evaluation of antiviral activity of single and combined repurposable drugs against SARS-CoV-2," Antiviral Research, Sep. 2020, 181:104878.
Rebeaud et al., "SARS-CoV-2 and the Use of Chloroquine as an Antiviral Treatment," Frontiers in Medicine, Apr. 24, 2020, 7:184, 6 pages.
Wang et al., "Remdesivir in adults with severe COVID-19: a randomised, double-blind, placebo-controlled, multicentre trial," Lancet, Apr. 29, 2020, 395:1569-1578.
Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.
Jones et al., "Di- and Triester Prodrags of the Varicella-Zoster Antiviral Agent 6-Methoxypurine Arabinoside," Journal of Medicinal Chemistry, Jan. 1992, 35(1):56-63.
Kim et al., "Synthesis and Evaluation of 2-Amino-6-fluoro-9-(4-hydroxy-3-hydroxymethylbut-1-yl) purine Mono-and Diesters as Potential Prodrags of Penciclovir." Bioorganic & Medicinal Chemistry, Mar. 1999, 7(3):565-70.
Kim et al., "Synthesis and Evaluation of 2-Amino-9-(1,3-dihydroxy-2-propoxvmethyl)-6-fluoropurine Mono-and Diesters as Potential Prodrugs of Ganciclovir," Journal of Medicinal Chemistry, Jan. 1999, 42(2):324-28.
Klumpp et al., "Chapter 20: Discovery and Clinical Evaluation of the Nucleoside Analog Balapiravir (R1626) for the Treatment of HCV Infection," Antiviral Drugs: From Basic Discovery through Clinical Trials, Jun. 20, 2011, pp. 287-304.
Moorman et al., "5'-ester prodrugs of the varicella-zoster antiviral agent, 6-methoxypurine arabinoside," Antiviral Chemistry & Chemotherapy, Jun. 1992, 3(3):141-46.
Nilsson et al., "Discovery of 4'-azido-2'-deoxy-2'-C-methyl cytidine and prodrugs thereof: A potent inhibitor of Hepatitis C virus replication," Bioorganic & Medicinal Chemistry Letters, May 2012, 22(9):3265-68.
Vieira et al., "Development of a Large-Scale Cyanation Process Using Continuous Flow Chemistry En Route to tire Synthesis of Remdesivir," Organic Process Research & Development, May 2020, 24(10):2113-2121.
Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/umversity-of-alabama-multi-center-collaboration-help-develop-remdesivir-with-gilead-thanks-to-37-5m-from-nih>, Mar. 1, 2020, 5 pages.
Beigel et al., "Remdesivir for the Treatment of Covid-19—Final Report," New England Journal of Medicine, Nov. 5, 2020, 383(19): 1813-1826.
Douafer et al., "Scope and limitations on aerosol drug delivery for the treatment of infectious respiratory diseases," Journal of Controlled Release, Sep. 2020, 325: 276-292.
Humeniuk et al., "Pharmacokinetic, Pharmacodynamic, and Drug-Interaction Profile of Remdesivir, a SARS-CoV-2 Replication Inhibitor," Clinical pharmacokinetics, May 2021, 60(2021): 569-583.
Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus, Mar. 16, 2020, 11 pages.
Koplon [online], "$37.5 million giant will address research of high-priority infections," UAB News, retrieved on Mar. 13, 2023, URL <https://www.uab.edu/news/health/item/10307-37-5-million-grant-will-address-research-of-high-priority-infections, Mar. 20, 2019, 1 page.
Pilcer et al., "Formulation strategy and use of excipients in pulmonary drag delivery," International Journal of Pharmaceutics, Jun. 2010, 392(1-2): 1-19.
Remington's Pharmaceutical Science, 17th ed., Gennaro (ed)., 1985, Chapter 68, 58 pages.
Spiner et al., "Effect of Remdesivir vs Standard Care on Clinical Status at 11 Days in Patients With Moderate COVID-19: A Randomized Clinical Trial," Jama, Sep. 2020, 324(11): 1048-1057.
Taylor, "Aulton's Pharmaceuties: The Design and Manufacture of Medicines; Chapter 37: Pulmonary Drug Delivery," 5th ed., Aulton et al. (ed), 2018: 653-670.
Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.
Yan et al., "Advantages of the Parent Nucleoside GS-441524 over Remdesivir for Covid-19 Treatment," ACS Medicinal Chemistry Letters, Jun. 30, 2020, 11(7):1361-1366.
Yan et al., "Gilead should ditch remdesivir and focus on its simpler and safer ancestor," STAT Health Care News, May 14, 2020, 6 pages.
Xie et al., "Engineering SARS-CoV-2 using a reverse genetic system," Nature protocols, Jan. 29, 2021, 16(3): 1761-1784.
U.S. Appl. No. 13/189,373, filed Jul. 22, 2011, Richard L. Mackman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.
U.S. Appl. No. 18/128,850, filed Mar. 30, 2023, Tomas Cihlar.
U.S. Appl. No. 17/222,125, filed Apr. 5, 2021, Scott Ellis.
U.S. Appl. No. 17/158,391, filed Jan. 26, 2021, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.

(56) References Cited

OTHER PUBLICATIONS

U.S. Appl. No. 17/578,682, filed Jan. 19, 2022, Michel Joseph Perron.
U.S. Appl. No. 17/895,123, filed Aug. 25, 2022, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.
U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/879,380, filed Aug. 29, 2022, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 17/458,023, filed Aug. 26, 2021, Byoung-Kwon Chun.
U.S. Appl. No. 18/098,950, filed Jan. 19, 2023, Byoung-Kwon Chun.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 17/355,813, filed Jun. 23, 2021, Daniel H. Byun.

* cited by examiner

| VIAL NO. | FORMULATION VEHICLE |
|---|---|
| 1 | PBS / 0.1% HPMC |
| 2 | 150 mM NaCl / 0.5% POLOXAMER 237 |
| 3 | 150 mM NaCl / 0.1% HPMC / 0.5% POLOXAMER 237 |
| 4 | 75 mM NaCl / 0.1% HPMC / 0.5% POLOXAMER 237 |
| 5 | 0.1% HPMC / 0.5% POLOXAMER 237 |
| 6 | 0.5% POLOXAMER 237 |
| 7 | 75mM NaCl / 0.1% HPMC / 0.02% TWEEN 80 |
| 8 | 0.1% HPMC / 0.02% TWEEN 80 |
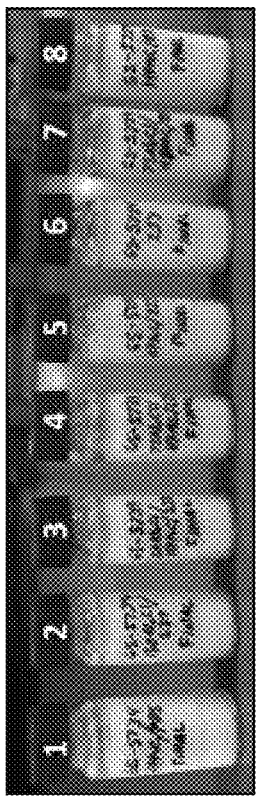
1 HOUR STANDING
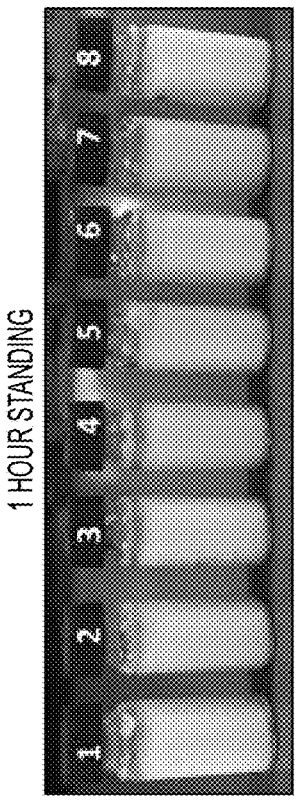
1 HOUR STANDING
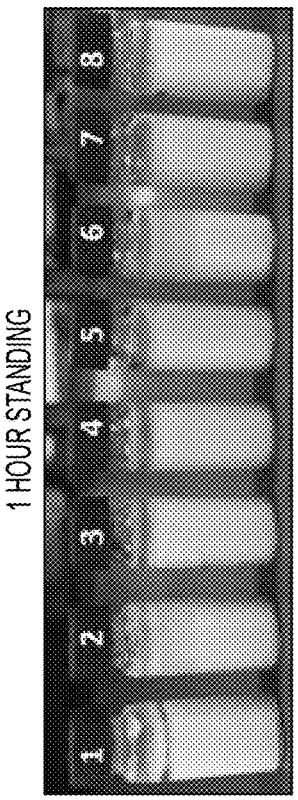
2 HOURS STANDING
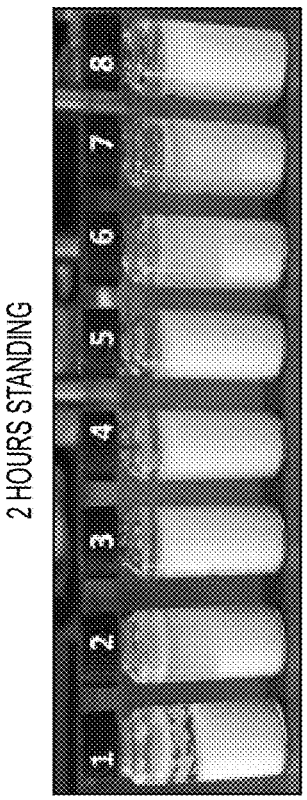
4 HOURS STANDING
FIG. 1

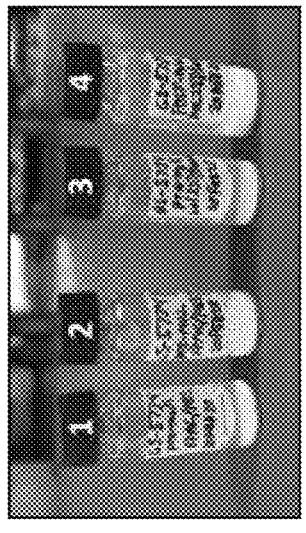
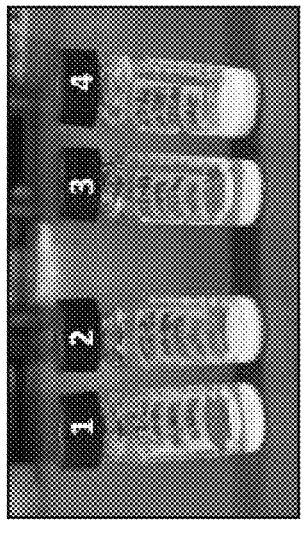
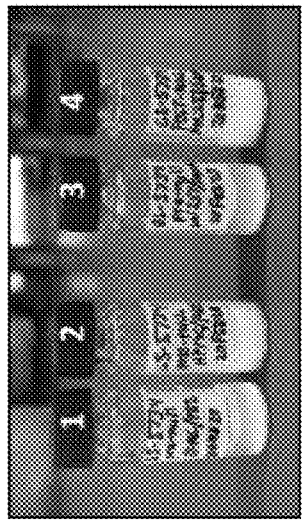
FRONT VIEW, 1 hr STANDING
FRONT VIEW, 24 hr STANDING
BACK VIEW, 1 hr STANDING
BACK VIEW, 24 hr STANDING
| VIAL NO. | FORMULATION VEHICLE |
|---|---|
| 1 | PBS / 0.1% HPMC; PRE-MILL |
| 2 | 150 mM NaCl / 0.1% HPMC / 0.5% POLOXAMER 237; PRE-MILL |
| 3 | PBS / 0.1% HPMC; POST-MILL |
| 4 | 150 mM NaCl / 0.1% HPMC / 0.5% POLOXAMER 237; POST-MILL |
*FIG. 2*

CONCENTRATION-TIME PROFILES OF FORMULA Ia AND ITS METABOLITES IN PLASMA FOLLOWING 0.536 mg/kg INHALED DEPOSITED DOSE OF FORMULA Ia TO AFRICAN GREEN MONKEYS (MEAN ± SD, N=4)

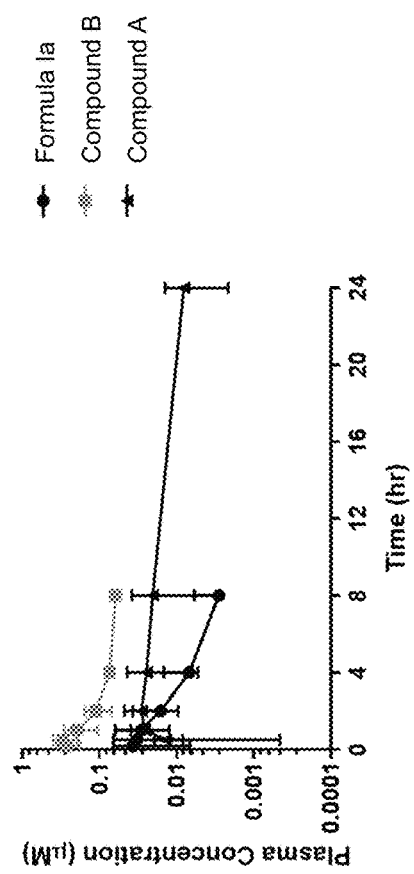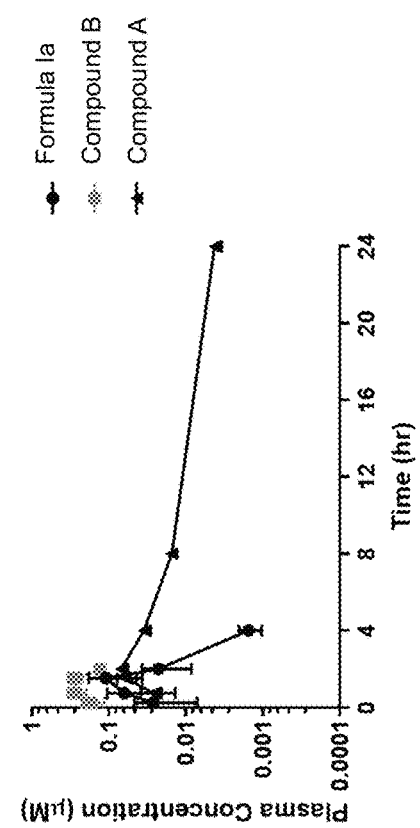
FIG. 20

INHALATION FORMULATIONS OF 1'-CYANO SUBSTITUTED CARBA-NUCLEOSIDE ANALOGS

CROSS REFERENCE TO RELATED APPLICATIONS

This application claims priority to U.S. Provisional Patent Application No. 63/005,724 filed Apr. 6, 2020; U.S. Provisional Patent Application No. 63/022,290 filed May 8, 2020; U.S. Provisional Patent Application No. 63/033,679 filed Jun. 2, 2020; and U.S. Provisional Patent Application No. 63/160,622 filed Mar. 12, 2021. The entire contents of these applications are incorporated herein by reference in their entirety.

FIELD

Provided are inhalable pharmaceutical formulations suitable for treating viral infections such as Arenaviridae, Coronaviridae, Filoviridae, Flaviviridae, Orthomyxoviridae, Pneumoviridae, or Paramyxoviridae viral infections. In particular, provided herein are inhalation formulation comprising the compound of Formula I, Formula Ia, or Formula Ib as described herein, or a pharmaceutically acceptable salt thereof, and an aqueous vehicle.

BACKGROUND

Preventing or treating some Arenaviridae, Coronaviridae, Filoviridae, Flaviviridae, Orthomyxovirus, Pneumoviridae, and Paramyxoviridae viral infections present challenges due to a lack of vaccine or post-exposure treatment modality for preventing or managing infections caused by viruses from these families. In some cases, patients only receive supportive therapy such as electrolyte and fluid balancing, oxygen, blood pressure maintenance, or treatment for secondary infections.

The compound (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate, referred to herein as the compound of Formula Ia, is known to exhibit antiviral properties against several viral families, including Arenaviridae, Coronaviridae, Filoviridae, Paramyxoviridae, and Flaviviridae viruses (see e.g., Warren, T. et al., Nature (2016) 531:381-385; Lo M K, et al. Sci. Reports 2017; 7:43395; Sheahan T P, et al. Sci. Transl. Med. 2017; 9:eaa13653; Agostini M L, et al. MBio 2018; 9(2):e00221-18; Cell Research (2020) 30:269-271, and WO 2017/184668). There is a need to develop a inhalable pharmaceutical composition comprising the compound of Formula Ia, or a pharmaceutically acceptable salt thereof. Such pharmaceutical formulations can be useful, especially in treatment of respiratory infections.

Delivery of therapeutic agents directly to affected respiratory tracts has several advantages. By targeting the delivery to the respiratory tracts, the drug reaches the target tissue without first entering the systemic circulation where the drug molecules are subjected to dilution, metabolism, distribution and excretion. A high local concentration of drug can be reached in the lungs while the systemic concentration is kept below that likely to cause adverse side effects. Inhalation therapy may also be used for drugs to be delivered to the bloodstream and finally to the desired site of action.

SUMMARY

Provided herein are pharmaceutical compositions comprising:
i. a compound of Formula I, Formula Ia, or Formula Ib:

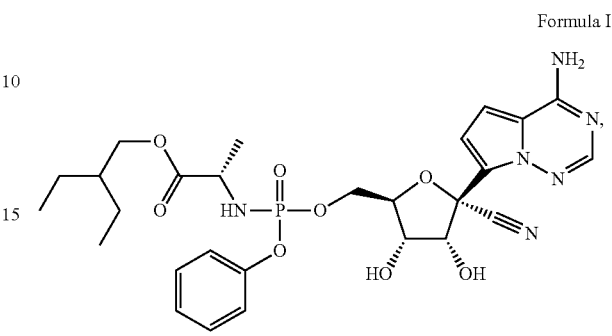

Formula I

Formula Ia

Formula Ib or a pharmaceutically acceptable salt thereof; and
ii. an aqueous vehicle;
wherein the pharmaceutical formulation is suitable for administration via inhalation.

In some embodiments, the disclosure provides pharmaceutical formulations comprising:
i. a compound of Formula I:

Formula I or a pharmaceutically acceptable salt thereof; and ii. an aqueous vehicle;
wherein the pharmaceutical formulation is suitable for administration via inhalation.

In some embodiments, the disclosure provides pharmaceutical formulations comprising:
i. a compound of Formula Ia:

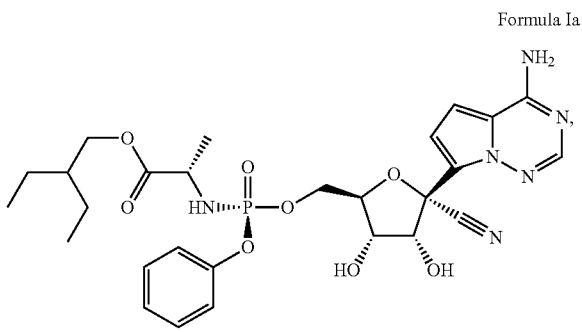 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Formula Ia or a pharmaceutically acceptable salt thereof; and
ii. an aqueous vehicle;
wherein the pharmaceutical formulation is suitable for administration via inhalation.

In some embodiments, the present disclosure provides a pharmaceutical formulation comprising:
i. a compound of Formula Ib:

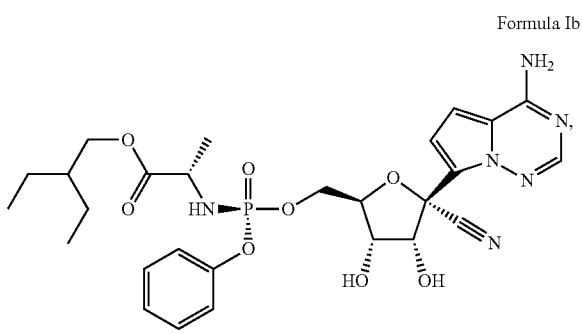 [SMILES: CCC(CC)COC(=O)[C@H](C)N[P@@](=O)(OC[C@H]1O[C@@](C#N)(c2ccc3c(N)ncnn23)[C@H](O)[C@@H]1O)Oc1ccccc1]

Formula Ib or a pharmaceutically acceptable salt thereof; and
ii. an aqueous vehicle;
wherein the pharmaceutical formulation is suitable for administration via inhalation.

Also provided herein are methods of treating or preventing a viral infection in a human in need thereof, wherein the methods comprise administering to the human a pharmaceutical formulation of the disclosure, wherein the administration is by inhalation.

BRIEF DESCRIPTION OF THE DRAWINGS

FIG. 1. Shows suspension stability of exemplary pharmaceutical formulations of the disclosure.

FIG. 2. Shows the impact of the particle size on suspension stabilities of exemplary pharmaceutical formulations of the disclosure.

The inhalation route also resulted in lower liver and kidney concentrations relative to IV dosing.

Figure 19:
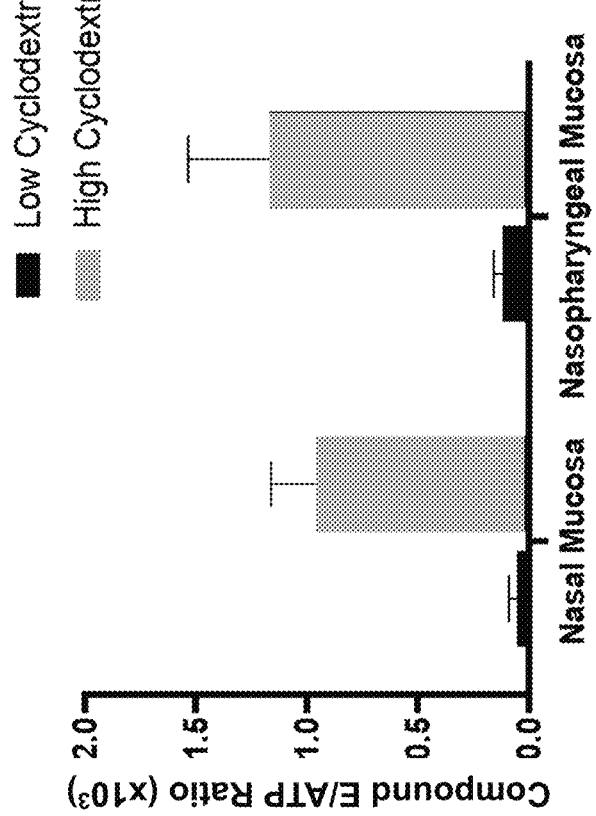
Figure 21:
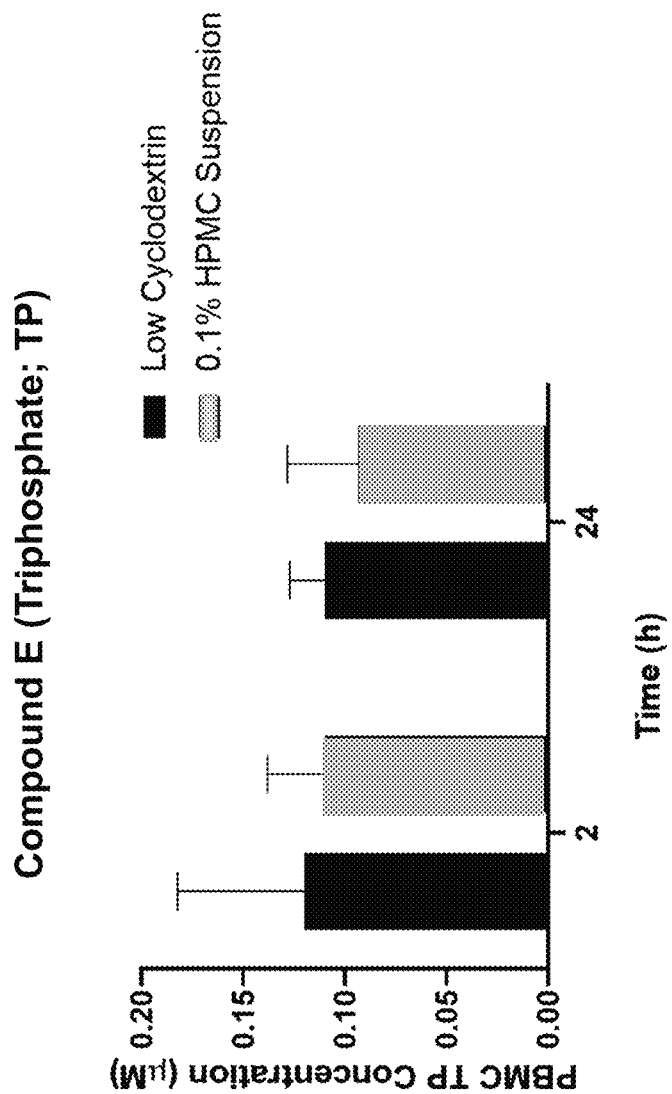
Figure 22:
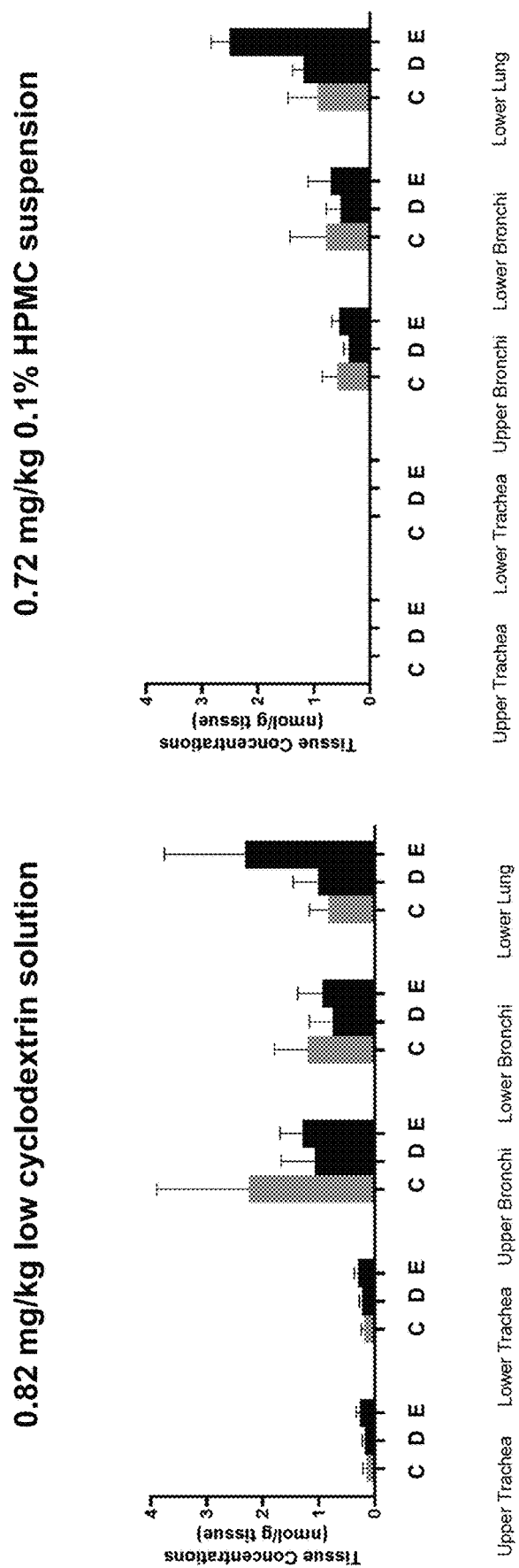
Figure 23:
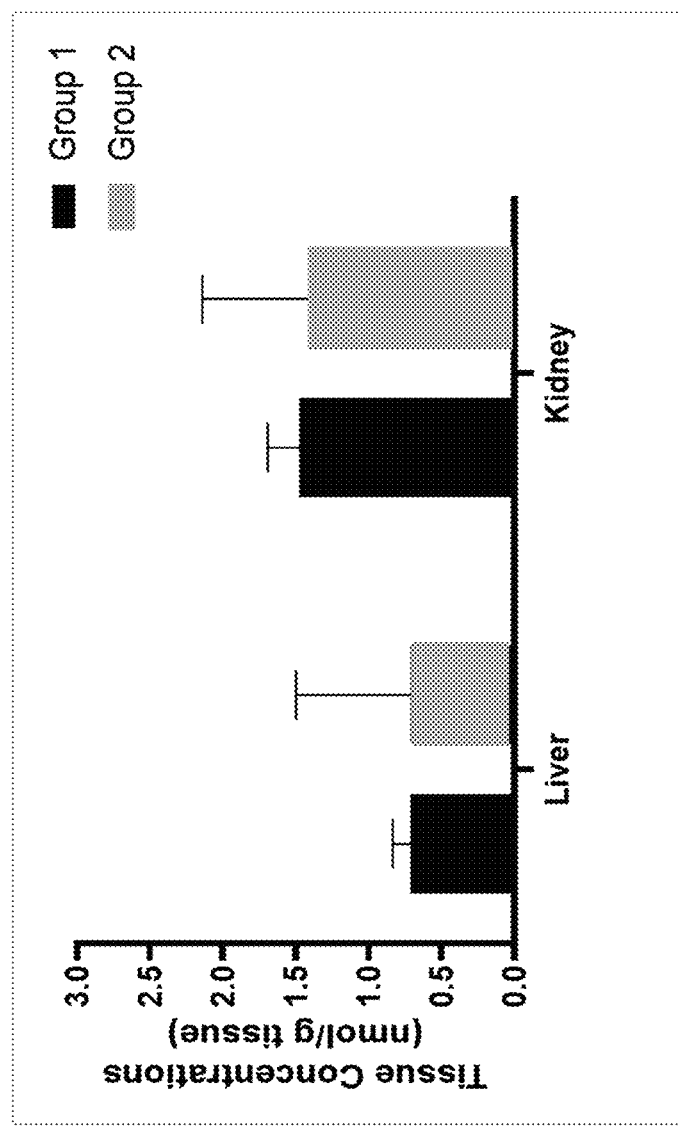
Figure 24:
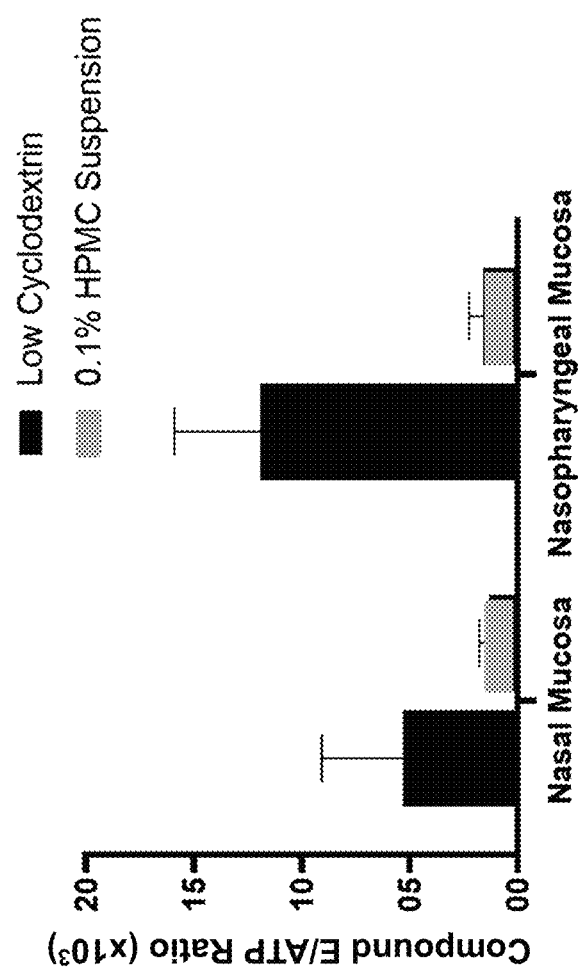

FIG. 19. Shows mucosa Compound E/ATP Ratio for two exemplary cyclodextrin formulations (low cyclodextrin formulation: 75 mg/mL cyclodextrin and high cyclodextrin formulation: 150 mg/mL) in AGM monkeys following inhalation administration. Compound E was detected in mucosa samples in low cyclodextrin group but the TP/ATP ratios were lower possibly due to blood contamination in the samples FIG. 20. Shows the plasma PK profile of two exemplary formulations (a cyclodextrin solution formulation and a 0.1% HPMC suspension formulation) in AGM monkeys following inhalation administration. As seen, the suspension and the suspension formulations showed similar AUCs but the suspension formulation showed prolonged exposure to the compound of Formula Ia and Compound B relative to the solution formulation.

FIG. 21. Shows PBMC triphosphate levels for two exemplary cyclodextrin formulations (75 mg/mL cyclodextrin solution formulation and 0.1% HPMC suspension formulation) in AGM monkeys following inhalation administration. As seen, the two formulations showed similar PBMC triphosphate levels.

FIG. 22. Respiratory tissues metabolite levels for compounds C, D, and E, for two exemplary cyclodextrin formulations (75 mg/mL cyclodextrin solution formulation and 0.1% HPMC suspension formulation) in AGM monkeys following inhalation administration. Tissue samples were collected 24 h post-dose. As seen, while the lung levels were similar, the levels in other tissues were somewhat lower with the suspension formulation.

FIG. 23. Shows total nucleotides levels in liver and kidney at 24 hours following inhalation administration of two exemplary formulations (75 mg/mL cyclodextrin solution formulation and 0.1% HPMC suspension formulation) to AGM monkeys. As seen the nucleotide levels were comparable for two formulations. The inhalation route also resulted in lower liver and kidney concentrations relative to IV dosing.

FIG. 24. Shows mucosa Compound E/ATP Ratio for two exemplary formulations (75 mg/mL cyclodextrin solution formulation and 0.1% HPMC suspension formulation) in AGM monkeys following inhalation administration. Triphosphate (Compound E) was detected in both groups but the TP/ATP ratios were lower for the suspension formulation. Blood contamination noted in the mucosa samples affects bioanalysis.

DETAILED DESCRIPTION

I. General

The present invention includes a pharmaceutical formulation comprising the compound of Formula I, Formula Ia, or Formula Ib and an aqueous vehicle, wherein the pharmaceutical formulation is for administration via inhalation.

II. Definitions

"The compound of Formula I" refers to the following compound:

Formula I

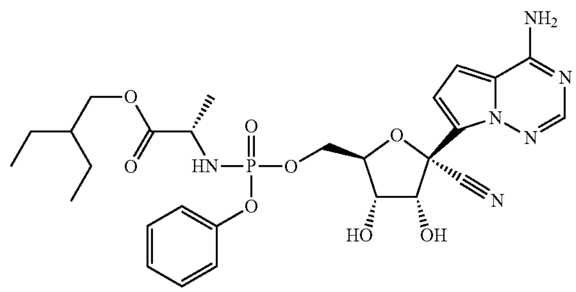

The compound of Formula I was disclosed in WO2012/012776. The IUPAC name for the compound of Formula I is 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate.

"The compound of Formula Ia" refers to the following compound:

Formula Ia

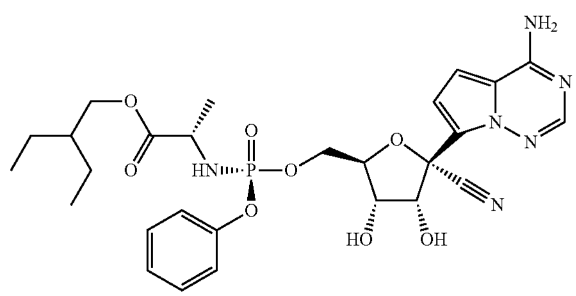

The compound of Formula Ia is disclosed in WO2016/069826. The IUPAC name for the compound of Formula Ia is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino) propanoate, and the CAS Registry Number is 1809249-37-3. The compound of Formula Ia is also referred to as remdesivir and GS-5734.

The "compound of Formula Ib" refers to the following compound:

Formula Ib

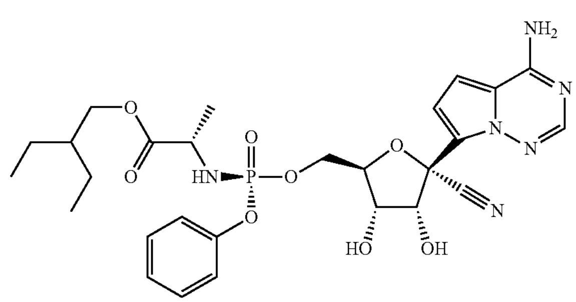

The compound of Formula Ib is disclosed in WO2016/069826. The IUPAC name for the compound of Formula Ib is (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino) propanoate.

The compounds of the disclosure, exemplified by Formula I, Formula Ia and Formula Ib have chiral centers, e.g., chiral carbon or phosphorus atoms. The compounds of the disclosure thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including compounds of Formula I, Formula Ia, or Formula Ib, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, Formula Ia, and Formula Ib in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, Formula Ia, and Formula Ib when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, Formula Ia, and Formula Ib.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

The terms "polyethylene glycol" or "PEG" as used herein refer to polymers of the general chemical formula $H(OCH_2CH_2)_n$ OH, also known as (α-Hydro-ω-hydroxy-poly-(oxy-1,2-ethanediyl), where "n" is greater than or equal to 4. Any PEG, substituted or unsubstituted, is encompassed by this term. PEGs are commercially available from a number of vendors (e.g., Carbowax™ (Dow Chemical, Midland, Mich.) and Poly-G® (Arch Chemicals, Norwalk, Conn.)).

"Prevention" or "preventing" means any treatment of a disease or condition that causes the clinical symptoms of the disease or condition not to develop. Compositions may, in some embodiments, be administered to a subject (including a human) who is at risk or has a family history of the disease or condition.

"DI water" (also be referred as deionized water, DIW, de-ionized water, demineralized water, or DM water) is water that has had essentially all of its mineral ions removed, such as cations including sodium, calcium, iron, and copper, and anions such as chloride and sulfate.

"Volume mean diameter" or VMD as used herein refers to the diameter of a hypothetical particle having the same average volume as that of the given sample.

The term "hypertonic saline" means a water solution containing greater than 0.9% (w/v) NaCl. For example, 3% hypertonic saline would contain 3% (w/v) NaCl.

III. Pharmaceutical Formulations

All pharmaceutical formulations described here comprise the compound of Formula I Formula Ia, or Formula Ib, or a pharmaceutically acceptable salt thereof, and an aqueous vehicle. In some embodiments, the pharmaceutical formulations provided herein comprise the compound of Formula I, or a pharmaceutically acceptable salt thereof and an aqueous vehicle. In some embodiments, the pharmaceutical formulations provided herein comprise the compound of Formula Ia, or a pharmaceutically acceptable salt thereof and an aqueous vehicle. In some embodiments, the pharmaceutical formulations provided herein comprise the compound of Formula Ib, or a pharmaceutically acceptable salt thereof and an aqueous vehicle. The aqueous vehicle comprises water and optionally one or more components selected from a co-solvent, a surfactant, a suspending agent, a tonicity agent, a buffer, a cyclodextrin, and an antimicrobial agent or preservative. The pharmaceutical formulations disclosed herein are for administration to a subject (for e.g., a human) by inhalation, for example the pharmaceutical formulations are for administration by inhalation in a nebulized or aerosol form.

1. The Compound of Formula I, Formula Ia, or Formula Ib

The compound of Formula I, Formula Ia, or Formula Ib can be used in any suitable amount to achieve the desired concentration in the pharmaceutical formulation. For example, the compound of Formula I, Formula Ia, or Formula Ib can be present in an amount of 0.1 mg to 1000 mg per one mL of the pharmaceutical formulation, or 0.1 mg to 800 mg, 0.1 mg to 600 mg, 0.1 mg to 400 mg, 0.1 mg to 200 mg, 0.1 mg to 100 mg, 0.1 mg to 50 mg, 0.1 mg to 30 mg, 0.5 mg to 1000 mg, 0.5 mg to 800 mg, 0.5 mg to 600 mg, 0.5 mg to 500 mg, 0.5 mg to 400 mg, 0.5 mg to 200 mg, 0.5 mg to 100 mg, 0.5 mg to 50 mg, 0.5 mg to 30 mg, 1 mg to 800 mg, 1 mg to 600 mg, 1 mg to 400 mg, 1 mg to 200 mg, 1 mg to 100 mg, 1 mg to 50 mg, 1 mg to 30 mg, 10 mg to 1000 mg, 10 mg to 800 mg, 10 mg to 600 mg, 10 mg to 500 mg, 10 mg to 400 mg, 10 mg to 200 mg, 10 mg to 100 mg, 10 mg to 50 mg, 10 mg to 30 mg, 50 mg to 1000 mg, 50 mg to 800 mg, 50 mg to 600 mg, 50 mg to 400 mg, 50 mg to 200 mg, 50 mg to 100 mg, 100 mg to 1000 mg, 100 mg to 800 mg, 100 mg to 600 mg, 100 mg to 400 mg, 100 mg to 200 mg, 200 mg to 1000 mg, 200 mg to 800 mg, 200 mg to 600 mg, 200 mg to 400 mg, 300 mg to 1000 mg, 300 mg to 800 mg, 300 mg to 600 mg, 300 mg to 400 mg, 400 mg to 1000 mg, 400 mg to 800 mg, 400 mg to 600 mg, 400 mg to 500 mg, 500 mg to 1000 mg, 500 mg to 800 mg, 500 mg to 600 mg, 600 mg to 1000 mg, 600 mg to 900 mg, 600 mg to 800 mg, 600 mg to 700 mg, 700 mg to 1000 mg, 700 mg to 900 mg, 700 mg to 800 mg, 800 mg to 1000 mg, 800 mg to 900 mg, 900 mg to 100 mg per one mL of the pharmaceutical formulation. In some embodiments, the compound of Formula I, Formula Ia, or Formula Ib is present in an amount of about 10 to about 500 mg per one mL of the pharmaceutical formulation, for example from about 10 to about 400 mg or about 10 to about 200 mg per one mL of the pharmaceutical formulation. In some embodiments, the compound of Formula I, Formula Ia, or Formula Ib is present in an amount of about 10 to about 40 mg per one mL of the pharmaceutical formulation.

In some embodiments, the compound of Formula I, Formula Ia, or Formula Ib is present in an amount of about 10 mg to about 50 mg, about 10 mg to about 40 mg, about 10 mg to about 30 mg, about 10 mg to about 20 mg, about 5 mg to about 50 mg, about 5 mg to about 40 mg, about 5 mg to about 30 mg, about 5 mg to about 20 mg, or about 5 mg to about 10 mg per one mL of the pharmaceutical formulation. In some embodiments, the compound of Formula I, Formula Ia, or Formula Ib is present in an amount of about 1 mg, about 5 mg, about 10 mg, about 15 mg, about 20, about 30, about 40, about 50, about 60, about 70, about 80, about 90, or about 100 mg per one mL of the pharmaceutical formulation. In some embodiments, the pharmaceutical formulation comprises about 15 mg of the compound of Formula I, Formula Ia, or Formula Ib per one mL of the pharmaceutical formulation.

The compound of Formula I, Formula Ia, or Formula Ib can be used in any suitable form. For example, the compound of Formula I, Formula Ia, or Formula Ib can be amorphous or crystalline. In some embodiments, the compound of Formula I, Formula Ia, or Formula Ib is amorphous. In some embodiments, the compound of Formula I, Formula Ia, or Formula Ib is crystalline.

Crystalline forms of the compound of Formula Ia useful in the methods and compositions of the present invention are described in U.S. Patent Application Publication No. 20180346504. For example, the compound of Formula Ia can be crystalline Form I, Form II, Form III, Form IV as described in U.S. Patent Application Publication No. 20180346504, or a combination thereof. In some embodiments, the compound of Formula Ia is crystalline.

In some embodiments, the compound of Formula Ia is crystalline Form II. In some embodiments, crystalline compound of Formula Ia is characterized by an X-ray powder diffraction (XRPD) pattern having at least three peaks selected from the group consisting of 22.3°, 16.2°, 22.5°, 13.8°, 12.7°, 16.9°, 10.6°, 14.5°, 24.3, 24.0°, 17.6°, 23.4°, 8.1°, 11.0°, 26.8°, 28.9°, 19.6°, 27.8°, 26.4°, 28.7°, 29.8°, 33.0°, 18.8°, 18.3°, 32.1°, 25.3°, 32.6°, 8.6°, 342°, 35.9°, 27.2°, 28.1°, 38.9°, 34.6°, 17.1°, 35.2°, 21.4°, 30.6°, 25.6°, 18.5°, 31.7°, 36.5°, and 37.1°±0.2° 2-0.

In some embodiments, crystalline Form II of the compound of Formula Ia has an XRPD pattern comprising degree 2θ-reflections (+/−0.2 degrees 2θ) at 22.3°, 16.9°, and 16.2°. In some embodiments, crystalline Form II of the compound of Formula Ia has an XRPD pattern comprising degree 2θ-reflections (+/−0.2 degrees 2θ) at 22.3°, 16.9°, and 16.2° and one or more of the degree 2θ-reflections (+/−0.2 degrees 2θ) at 13.8° and 12.7°. In some embodiments, crystalline Form II of the compound of Formula Ia has an XRPD pattern comprising degree 2θ-reflections (+/−0.2 degrees 2θ) at 22.3°, 16.9°, and 16.2° and one of the degree 2θ-reflections (+/−0.2 degrees 2θ) at 13.8° and 12.7°. In some embodiments, crystalline Form II of the compound of Formula Ia has an XRPD pattern comprising degree 2θ-reflections (+/−0.2 degrees 2θ) at 22.3°, 16.9°, and 16.2° and two of the degree 2θ-reflections (+/−0.2 degrees 2θ) at 13.8° and 12.7°. In some embodiments, crystalline Form II the compound of Formula Ia has an XRPD pattern comprising degree 2θ-reflections (+/−0.2 degrees 2θ) at 22.3°, 16.9°, 16.2°, 13.8° and 12.7°. In some embodiments, crystalline Form II the compound of Formula Ia has an XRPD pattern comprising any three degree 2θ-reflections (+/−0.2 degrees 2θ) selected from the group consisting of 22.3°, 16.9°, 16.2°, 13.8°, and 12.7°.

In some embodiments, crystalline Form II of the compound of Formula Ia has an XRPD pattern further comprising degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and one or more of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and one of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and two of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8°, 12.7°, 22.5°, 10.6° and 14.5°. In some embodiments, crystalline Form II of the compound of Formula Ia has an XRPD pattern comprising any three degree 2θ-reflections (+/−0.2 degrees 2θ) selected from the group consisting of 22.3°, 16.9°, 16.2°, 13.8°, 12.7°, 22.5°, 10.6° and 14.5°.

In some embodiments, the compound of Formula Ia is mixture of crystalline Form II and crystalline Form IV. In some embodiments, the compound of Formula Ia is Mixture I, Mixture II, or Mixture III as described in in U.S. Patent Application Publication No. 20180346504.

In some embodiments, the compound of Formula Ia is Mixture I having an XRPD pattern comprising degree 2θ-reflections (+/−0.2 degrees 2θ) at 15.9°, 22.6°, and 14.1°. In some embodiments, Mixture I has an XRPD pattern comprising degree 2θ-reflections (+/−0.2 degrees 2θ) at 15.9°, 22.6°, and 14.1° and the degree 2θ-reflection (+/−0.2 degrees 2θ) at 12.5°. In some embodiments, Mixture I has an XRPD pattern comprising degree 2θ-reflections (+/−0.2 degrees 2θ) at 15.9°, 22.6°, 14.1°, and 12.5°. In some embodiments, Mixture I has an XRPD pattern comprising any three degree 2θ-reflections (+/−0.2 degrees 2θ) selected from the group consisting of 15.9°, 22.6°, 14.1°, and 12.5°.

In some embodiments, the compound of Formula Ia is Mixture II having an XRPD pattern comprising degree 2θ-reflections (+/−0.2 degrees 2θ) at 16.1°, 22.4°, and 12.7°. In some embodiments, Mixture II has an XRPD pattern comprising degree 2θ-reflections (+/−0.2 degrees 2θ) at 16.1°, 22.4°, and 12.7° and one or more of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and one of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and two of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and three of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, 12.7°, 24.2°, 16.8°, and 8.1°. In some embodiments, Mixture II has an XRPD pattern comprising any three degree 2θ-reflections (+/−0.2 degrees 2θ) selected from the group consisting of 16.1°, 22.4°, 12.7°, 24.2°, 16.8°, 8.1°, 13.9°, 17.5°, 11.1°, 10.7°, 14.7°, and 19.8°.

In some embodiments, the compound of Formula Ia is Mixture III having an XRPD pattern comprising degree 2θ-reflections (+/−0.2 degrees 2θ) at 16.7°, 12.6°, and 17.2°. In some embodiments, Mixture III has an XRPD pattern comprising degree 2θ-reflections (+/−0.2 degrees 2θ) at 16.7°, 12.6°, and 17.2° and one or more of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and one of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and two of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, 17.2°, 19.6° and 14.1°. In some embodiments, Mixture III has an XRPD pattern comprising any three degree 2θ-reflections (+/−0.2 degrees 2θ) selected from the group consisting of 16.7°, 12.6°, 17.2°, 19.6° and 14.1°.

The compound of Formula I, Formula Ia, or Formula Ib can have any suitable purity. For example, the compound of Formula I, Formula Ia, or Formula Ib can have a purity of at least about 90%, or at least about 91%, about 92%, about 93%, about 94%, about 95%, about 96%, about 97%, about 98%, about 99%, or at least about 99.1%, about 99.2%, about 99.3%, about 99.4%, about 99.5%, about 99.6%, about 99.7%, about 99.8% or at least about 99.9%. In some embodiments, the compound of Formula I, Formula Ia, or Formula Ib has a purity of at least about 99.1%. In some embodiments, the compound of Formula I, Formula Ia, or Formula Ib has a purity of at least about 99.3%. In some embodiments, the compound of Formula I, Formula Ia, or Formula Ib has a purity of at least about 99.5%. In some embodiments, the compound of Formula I, Formula Ia, or Formula Ib has a purity of at least about 99.7%.

The impurities present in the compound of Formula I, Formula Ia, or Formula Ib can include unreacted starting material, undesirable side-products, and other materials. Representative impurities include Impurity A:

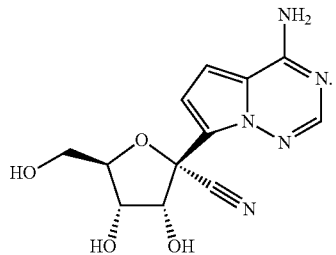 [SMILES: N#C[C@@]1(c2ccc3c(N)ncnn23)O[C@H](CO)[C@@H](O)[C@H]1O]

Impurity A can be present in an amount less than about 0.5%, or less than about 0.45%, about 0.40%, about 0.35%, about 0.30%, about 0.25%, about 0.20%, about 0.15%, about 0.10%, about 0.09%, about 0.08%, about 0.07%, about 0.06%, about 0.05%, about 0.04%, about 0.03%, about 0.02%, or less than about 0.01%. The amount of Impurity A can be measured in %AN (% area normalization) as measured by HPLC, or can be based on weight (w/w). In some embodiments, the compound of Formula I, Formula Ia, or Formula Ib includes less than about 0.10% Impurity A. In some embodiments, the compound of Formula I, Formula Ia, or Formula Ib includes less than about 0.05% Impurity A.

In some embodiments, the compound of Formula I, Formula Ia, or Formula Ib can have a purity of at least about 99.1%, and include less than about 0.10% Impurity A. In some embodiments, the compound of Formula I, Formula Ia, or Formula Ib can have a purity of at least about 99.1%, and include less than about 0.05% Impurity A. In some embodiments, the compound of Formula I, Formula Ia, or Formula Ib can have a purity of at least about 99.1%, and include less than about 0.04% Impurity A. In some embodiments, the compound of Formula I, Formula Ia, or Formula Ib can have a purity of at least about 99.5%, and include less than about 0.04% Impurity A. In some embodiments, the compound of Formula I, Formula Ia, or Formula Ib can have a purity of at least about 99.5%, and include less than about 0.04% Impurity A.

In some embodiments, the compound of Formula I, Formula Ia, or Formula Ib is a micronized form. In some embodiments, the micronized form has a $d_{90}$ of less than 50 μm. For example, the micronized form has a $d_{90}$ of less than 45 μm, 40 μm, 35 μm, 30 μm, 25 μm, 20 μm, 15 μm, 10 μm, 9 μm, 8 μm, 7 μm, 6 μm, 5 μm, 4 μm, 3 μm, 2 μm, or 1 μm. In some embodiments, the micronized form has a $d_{90}$ of about 0.1 μm-50 μm, for example, about 0.1 μm-45 μm, 0.1 μm-40 μm, 0.1 μm-35 μm, 0.1 μm-30 μm, 0.1 μm-25 μm, 0.1 μm-20 μm, 0.1 μm-15 μm, 0.1 μm-10 μm, 0.1 μm-9 μm, 0.1 μm-8 μm, 0.1 μm-7 μm, 0.1 μm-6 μm, 0.1 μm-5 μm, 0.1 μm-4 μm, 0.1 μm-3 μm, 0.1 μm-2 μm, about 0.5 μm-50 μm, about 0.5 μm-45 μm, 0.5 μm-40 μm, 0.5 μm-35 μm, 0.5 μm-30 μm, 0.5 μm-25 μm, 0.5 μm-20 μm, 0.5 μm-15 μm, 0.5 μm-10 μm, 0.5 μm-9 μm, 0.5 μm-8 μm, 0.5 μm-7 μm, 0.5 μm-6 μm, 0.5 μm-5 μm, 0.5 μm-4 μm, 0.5 μm-3 μm, 0.5 μm-2 μm, about 1 μm-50 μm, about 1 μm-45 μm, 1 μm-40 μm, 1 μm-35 μm, 1 μm-30 μm, 1 μm-25 μm, 1 μm-20 μm, 1 μm-15 μm, 1 μm-10 μm, 1 μm-9 μm, 1 μm-8 μm, 1 μm-7 μm, 1 μm-6 μm, 1 μm-5 μm, 1 μm-4 μm, 1 μm-3 μm, or 1 μm-2 μm. In some embodiments, the micronized form has a $d_{90}$ of ≤about 10 μm, for example ≤about 5 μm. In some embodiments, the micronized form has a $d_{90}$ of about 1 μm-10 μm, for example about 0.1 μm-5 μm. In some embodiments, the micronized form has a $d_{90}$ of about 0.1 μm-5 μm. In some embodiments, the micronized form has a $d_{90}$ of about 4 μm-5 μm.

In some embodiments, the micronized form has a $d_{50}$ of less than 30 μm. For example, the micronized form has a $d_{50}$ of less than 25 μm, 20 μm, 15 μm, 10 μm, 9 μm, 8 μm, 7 μm, 6 μm, 5 μm, 4 μm, 3 μm, 2 μm, or 1 μm. In some embodiments, the micronized form has a $d_{50}$ of about 0.1 μm-30 μm, for example, about 0.1 μm-25 μm, 0.1 μm-20 μm, 0.1 μm-15 μm, 0.1 μm-10 μm, 0.1 μm-9 μm, 0.1 μm-8 μm, 0.1 μm-7 μm, 0.1 μm-6 μm, 0.1 μm-5 μm, 0.1 μm-4 μm, 0.1 μm-3 μm, 0.1 μm-2 μm, 0.1 μm-1 μm, 0.5 μm-30 μm, about 0.5 μm-25 μm, 0.5 μm-20 μm, 0.5 μm-15 μm, 0.5 μm-10 μm, 0.5 μm-9 μm, 0.5 μm-8 μm, 0.5 μm-7 μm, 0.5 μm-6 μm, 0.5 μm-5 μm, 0.5 μm-4 μm, 0.5 μm-3 μm, 0.5 μm-2 μm, 0.5 μm-1 μm, 1 μm-30 μm, 1 μm-25 μm, 1 μm-20 μm, 1 μm-15 μm, 1 μm-10 μm, 1 μm-9 μm, 1 μm-8 μm, 1 μm-7 μm, 1 μm-6 μm, 1 μm-5 μm, 1 μm-4 μm, 1 μm-3 μm, or 1 μm-2 μm. In some embodiments, the micronized form has a $d_{50}$ of about 1 μm-10 μm. In some embodiments, the micronized form has a $d_{50}$ of about 1 μm-5 μm. In some embodiments, the micronized form has a $d_{50}$ of about 4 μm, 3 μm, 2 μm, or 1 μm. In some embodiments, the micronized form has a $d_{50}$ of about 3 μm-4 μm.

In some embodiments, the micronized form has a $d_{10}$ of less than 20 μm. For example, the micronized form has a $d_{10}$ of less than 15 μm, 10 μm, 9 μm, 8 μm, 7 μm, 6 μm, 5 μm, 4 μm, 3 μm, 2 μm, 1 μm, 0.5 μm, 0.4 μm, 0.3 μm, 0.2 μm, or 0.1 μm. In some embodiments, the micronized form has a $d_{10}$ of about 0.1 μm-20 μm, for example, about 1 μm-20 μm, 1 μm-15 μm, 1 μm-10 μm, 1 μm-9 μm, 1 μm-8 μm, 1 μm-7 μm, 1 μm-6 μm, 1 μm-5 μm, 1 μm-4 μm, 1 μm-3 μm, 1 μm-2 μm, 0.1 μm-15 μm, 0.1 μm-10 μm, 0.1 μm-9 μm, 0.1 μm-8 μm, 0.1 μm-7 μm, 0.1 μm-6 μm, 0.1 μm-5 μm, 0.1 μm-4 μm, 0.1 μm-3 μm, 0.1 μm-2 μm, or 0.1 μm-1 μm. In some embodiments, the micronized form has a $d_{10}$ of about 0.1 μm-10 μm. In some embodiments, the micronized form has a $d_{10}$ of about 0.1 μm-5 μm. In some embodiments, the micronized form has a $d_{10}$ of about 0.5 μm-5 μm. In some embodiments, the micronized form has a $d_{10}$ of about 4 μm, 3 μm, 2 μm, 1 μm, 0.9 μm, 0.8 μm, 0.7 μm, 0.6 μm, 0.5 μm, 0.4 μm, 0.3 μm, 0.2 μm, or 0.1 μm. In some embodiments, the micronized form has a $d_{10}$ of about 1 μm-3 μm.

In some embodiments, the compound of Formula I, Formula Ia, or Formula Ib is not micronized (also referred to as non-micronized or unmicronized).

2. Solvents and Co-Solvents

The pharmaceutical formulations described herein comprise the compound of Formula I, Formula Ia, or Formula Ib in an aqueous vehicle. The water in the aqueous vehicle can be any suitable water, such as DI water, distilled water, or sterile water. In some embodiments, the water is DI water.

In some embodiments, the aqueous vehicle further comprises a co-solvent. Exemplary co-solvents include but are not limited to ethanol, glycerin, propylene glycol, or PEG (polyethylene glycol, for example PEG 100), N-methyl-2-pyrrolidone and dimethyl sulfoxide. In some embodiments, the co-solvent is ethanol, glycerin, propylene glycol, PEG (for example PEG 100), or a combination thereof. In some embodiments, the co-solvent is ethanol, glycerin, propylene glycol, N-methyl-2-pyrrolidone, dimethyl sulfoxide or a combination thereof. In some embodiments, the co-solvent is ethanol, glycerin, propylene glycol, or a combination thereof.

The compound of Formula I, Formula Ia, or Formula Ib can be present in the pharmaceutical formulation in any form. For example, the compound of Formula I, Formula Ia, or Formula Ib can be present as a solution, suspension, or an emulsion in the aqueous vehicle. In some embodiments, the compound of Formula I, Formula Ia, or Formula Ib is present as a solution in the aqueous vehicle. In some embodiments, the compound of Formula I, Formula Ia, or Formula Ib is present as a suspension in the aqueous vehicle. In some embodiments, the compound of Formula I, Formula Ia, or Formula Ib is present as an emulsion in the aqueous vehicle.

3. Surfactant

The pharmaceutical formulations described herein further comprise a surfactant. Surfactants which can be used to form the pharmaceutical formulations described include, but are not limited to, hydrophilic surfactants, lipophilic surfactants, and mixtures thereof. That is, a hydrophilic surfactant or a mixture of two or more hydrophilic surfactants can be employed, a lipophilic surfactant or a mixture of two or more lipophilic surfactants can be employed, or a mixture of at least one hydrophilic surfactant and at least one lipophilic surfactant can be employed.

Some useful surfactants that can be used in the pharmaceutical formulations disclosed herein include, but are not limited to, oleic acid available under the trade names Mednique 6322 and Emersol 6321 (from Cognis Corp., Cincinnati, Ohio); cetylpyridinium chloride (from Arrow Chemical, Inc. Westwood, N.J.); soya lecithin available under the trade name Epikuron 200 (from Lucas Meyer Decatur, Ill.); polyoxyethylene(20) sorbitan monolaurate available under the tradename Tween 20 (from ICI Specialty Chemicals, Wilmington, Del.); polyoxyethylene(20) sorbitan monostearate available under the tradename Tween 60 (from ICI); polyoxyethylene(20) sorbitan monooleate available under the tradename Tween 80 (from ICI); polyoxyethylene (10) stearyl ether available under the tradename Brij 76 (from ICI); polyoxyethylene (2) oleyl ether available under the tradename Brij 92 (frown ICI); Polyoxyethylene-polyoxypropylene-ethylenediamine block copolymer available under the tradename Tetronic 150 R1 (from BASF); polyoxypropylene-polyoxyethylene block copolymers available under the trade names Pluronic L-92, Pluronic L-121 end Pluronic F68 (from BASF); castor oil ethoxylate available under the tradename Alkasurf CO-40 (from Rhone-Poulenc Mississauga Ontario, Canada); and mixtures thereof.

An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, some ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

In some embodiments, the pharmaceutical formulations provided herein comprise a non-ionic surfactant. In some embodiments, the surfactant is a polysorbate or a poloxamer. For example, the surfactant is polysorbate 20 (Tween 20), polysorbate 40 (Tween 40), polysorbate 60 (Tween 60), polysorbate 65 (Tween 65), polysorbate 80 (Tween 80), polysorbate 85 (Tween 85), poloxamer 124, poloxamer 188, poloxamer 237, poloxamer 338, or poloxamer 407. In some embodiments, the surfactant is a polysorbate, for example the surfactant is polysorbate 20 (Tween 20), polysorbate 40 (Tween 40), polysorbate 60 (Tween 60), polysorbate 65 (Tween 65), polysorbate 80 (Tween 80), or polysorbate 85 (Tween 85). In some embodiments, the surfactant is polysorbate 80 (Tween 80).

In some embodiments, the surfactant is a poloxamer. For example, the surfactant is poloxamer 124, poloxamer 188, poloxamer 237, poloxamer 338, or poloxamer 407. In some embodiments, the surfactant is poloxamer 237.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, some lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Any desired amount of surfactant can be used in the pharmaceutical formulations described herein. Typically, the surfactant is present in an amount of about 0.01% to about 2.0% weight/volume relative to the volume of the pharmaceutical formulation. For example, the surfactant is present in an amount of about 0.01% to about 1.5% or about 0.01% to about 1.0% weight/volume relative to the volume of the pharmaceutical formulation. In some embodiments, the surfactant is present in an amount of about 0.5% relative to the volume of the pharmaceutical formulation.

In some examples, the surfactant is present in an amount of about 0.01% to about 1.0% weight/volume relative to the volume of the pharmaceutical formulation. In some examples, the surfactant is present in an amount of about 0.01% to about 0.05% relative to the volume of the pharmaceutical formulation. For example, the surfactant is present in an amount of about 0.02% weight/volume relative to the volume of the pharmaceutical formulation.

In some embodiments, the surfactant is a poloxamer and it is present in an amount of about 0.01% to about 2.0% weight/volume relative to the volume of the pharmaceutical formulation. For example, the surfactant is a poloxamer and it is present in an amount of about 0.01% to about 1.5% or about 0.01% to about 1.0% weight/volume relative to the volume of the pharmaceutical formulation. In some embodiments, the surfactant is a poloxamer and it is present in an amount of about 0.5% weight/volume relative to the volume of the pharmaceutical formulation.

In some embodiments, the surfactant is poloxamer 124, poloxamer 188, poloxamer 237, poloxamer 338, or poloxamer 407, and it is present in an amount of about 0.01% to about 2.0% weight/volume relative to the volume of the pharmaceutical formulation. For example, the surfactant is poloxamer 124, poloxamer 188, poloxamer 237, poloxamer 338, or poloxamer 407, and it is present in an amount of about 0.01% to about 1.5% or about 0.01% to about 1.0% weight/volume relative to the volume of the pharmaceutical formulation. In some embodiments, the surfactant is poloxamer 124, poloxamer 188, poloxamer 237, poloxamer 338, or poloxamer 407, and it is present in an amount of about 0.5% weight/volume relative to the volume of the pharmaceutical formulation.

In some embodiments, the surfactant is poloxamer 237, and it is present in an amount of about 0.01% to about 2.0% weight/volume relative to the volume of the pharmaceutical formulation. For example, the surfactant is poloxamer 237, and it is present in an amount of about 0.01% to about 1.5% or about 0.01% to about 1.0% weight/volume relative to the volume of the pharmaceutical formulation. In some embodiments, the surfactant is poloxamer 237, and it is present in an amount of about 0.5% weight/volume relative to the volume of the pharmaceutical formulation.

In some examples, the surfactant is a polysorbate and it is present in an amount of about of about 0.01% to about 1.0% weight/volume relative to the volume of the pharmaceutical formulation. For example, the surfactant is polysorbate and it is present in an amount of about 0.01% to about 0.05% relative to the volume of the pharmaceutical formulation. In some embodiments, the surfactant is a polysorbate and it is present an amount of about 0.02% weight/volume relative to the volume of the pharmaceutical formulation.

In some examples, the surfactant is polysorbate 20 (Tween 20), polysorbate 40 (Tween 40), polysorbate 60 (Tween 60), polysorbate 65 (Tween 65), polysorbate 80 (Tween 80), or polysorbate 85 (Tween 85), and it is present in an amount of about of about 0.01% to about 1.0% weight/volume relative to the volume of the pharmaceutical formulation. For example, the surfactant is polysorbate 20 (Tween 20), polysorbate 40 (Tween 40), polysorbate 60 (Tween 60), polysorbate 65 (Tween 65), polysorbate 80 (Tween 80), or polysorbate 85 (Tween 85) and it is present in an amount of about 0.01% to about 0.05% relative to the volume of the pharmaceutical formulation. In some embodiments, the surfactant is polysorbate 20 (Tween 20), polysorbate 40 (Tween 40), polysorbate 60 (Tween 60), polysorbate 65 (Tween 65), polysorbate 80 (Tween 80), or polysorbate 85 (Tween 85), and it is present an amount of about 0.02% weight/volume relative to the volume of the pharmaceutical formulation.

In some examples, the surfactant is polysorbate 80 (Tween 80) and it is present in an amount of about of about 0.01% to about 1.0% weight/volume relative to the volume of the pharmaceutical formulation. For example, the surfactant is polysorbate 80 (Tween 80) and it is present in an amount of about 0.01% to about 0.05% relative to the volume of the pharmaceutical formulation. In some embodiments, the surfactant is polysorbate 80 (Tween 80) and it is present an amount of about 0.02% weight/volume relative to the volume of the pharmaceutical formulation.

In some embodiments, the pharmaceutical formulation described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises polysorbate 80 (Tween 80) in an amount of about 0.01% to about 1.0% (e.g., about 0.01% to about 0.05%, e.g., about 0.02%) weight/volume relative to the volume of the pharmaceutical formulation.

In some embodiments, the pharmaceutical formulation described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises poloxamer 237 in an amount of about 0.01% to about 1.5% (e.g., or about 0.01% to about 1.0%, e.g., about 0.5%) weight/volume relative to the volume of the pharmaceutical formulation.

4. Suspending Agent

In some embodiments, the pharmaceutical formulations described herein further comprise a suspending agent. In some examples, the suspending agent is a polymer, for e.g., a cellulose based polymer.

In some embodiment, the suspending agent is selected from the group consisting of hydroxypropyl cellulose (HPC), hydroxymethyl cellulose, hydroxypropyl methyl cellulose (HPMC), methyl cellulose polymer, hydroxyethyl cellulose, sodium carboxymethyl cellulose (Na-CMC), microcrystalline cellulose, carboxy methyl cellulose, and cellulose. In some embodiments, the suspending agent is selected from methyl cellulose, carboxy methyl cellulose, hydroxypropyl methylcellulose, and povidone (e.g., povidone K12, povidone K17, povidone K25, Povidone K30, or Povidone K90). In some embodiments, the suspending agent is selected from the group consisting of carboxy methyl cellulose, hydroxypropyl methylcellulose, and hydroxypropyl methylcellulose. In some embodiments, the suspending agent is carboxy methyl cellulose. In some embodiments, the suspending agent is hydroxypropyl methyl cellulose.

Any amount of suspending agent may be used. In some embodiments, the amount of suspending agent is from about 0.01% to about 5.0% weight/volume relative to the volume of the pharmaceutical formulation. For example, the amount of suspending agent is about 0.01%-4.5%, 0.01%-4.0%, 0.01%-3.5%, 0.01%-3.0%, 0.01%-2.5%, 0.01%-2.0%, 0.01%-1.5%, 0.01%-1.0%, 0.01%-0.5%, 0.05%-5.0%, 0.05%-4.5%, 0.5%-4.0%, 0.05%-3.5%, 0.05%-3.0%, 0.05%-2.05%, 0.05%-2.0%, 0.05%-1.5%, 0.05%-1.0%, 0.05%-0.5% weight/volume relative to the volume of the pharmaceutical formulation. In some embodiments, the amount of the suspending agent is from about 0.01% to about 1.0% weight/volume relative to the volume of the pharmaceutical formulation, for example from about 0.05% to about 1.5% weight/volume relative to the volume of the pharmaceutical formulation. In some embodiments, the amount of suspending agent is about 0.1% weight/volume relative to the volume of the pharmaceutical formulation.

In some embodiments, the suspending agent is hydroxypropyl cellulose and it is present in the amount of about 0.01% to about 1.0% weight/volume relative to the volume of the pharmaceutical formulation, for example from about 0.05% to about 1.5% weight/volume relative to the volume of the pharmaceutical formulation. In some embodiments, the suspending agent is hydroxypropyl cellulose and it is present in the amount of about 0.1% weight/volume relative to the volume of the pharmaceutical formulation.

In some embodiments, the pharmaceutical formulation described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises (i) poloxamer 237 in an amount of about 0.01% to about 1.5% (e.g., or about 0.01% to about 1.0%, e.g., about 0.5%) weight/volume relative to the volume of the pharmaceutical formulation and (ii) hydroxypropyl cellulose in an amount of about 0.01% to about 1.0% (e.g., about 0.05% to about 1.5%, e.g., about 0.1%) weight/volume relative to the volume of the pharmaceutical formulation.

In some embodiments, the pharmaceutical formulation described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises (i) polysorbate 80 (Tween 80) in an amount of about 0.01% to about 1.0% (e.g., about 0.01% to about 0.05%, e.g., about 0.02%) weight/volume relative to the volume of the pharmaceutical formulation and (ii) hydroxypropyl cellulose in an amount of about 0.01% to about 1.0% (e.g., about 0.05% to about 1.5%, e.g., about 0.1%) weight/volume relative to the volume of the pharmaceutical formulation.

5. Tonicity Agent

In some embodiments, the pharmaceutical formulations disclosed herein further comprise a tonicity agent. In some embodiments, the tonicity agents may enhance the overall comfort to the patient. In some embodiments, the tonicity adjusting agents are used to adjust the osmolality of the pharmaceutical composition to about 150 to about 1200 mOsm/Kg. In some embodiments, the tonicity agent is used to adjust the osmolarity of the pharmaceutical composition to about 200 mOsm/Kg to about 800 mOsm/Kg, for example to about 200 mOsm/Kg to about 600 mOsm/Kg, about 250 mOsm/Kg to about 500 mOsm/Kg, about 250 mOsm/Kg to about 350 mOsm/Kg, about 275 mOsm/Kg to about 325 mOsm/Kg. In some embodiments, the tonicity agent is used to adjust the osmolarity of the pharmaceutical composition to about 300 mOsm/Kg.

Tonicity-adjusting agents that can be used in the pharmaceutical formulations disclosed herein include, but are not limited to, sodium chloride, sodium sulfate, dextrose, lactose, sodium phosphate, sorbitol, mannitol and sucrose or combination thereof. In some embodiments, the tonicity adjusting agent is sodium chloride or sodium sulfate. In some embodiments, the tonicity adjusting agent is sodium chloride. In some embodiments, the tonicity adjusting agent is sodium sulfate.

In some embodiments, sodium chloride or sodium sulfate is used to adjust the osmolality of the pharmaceutical composition to about 150 to about 1200 mOsm/Kg, for example to about 200 mOsm/Kg to about 800 mOsm/Kg. In some embodiments, sodium chloride or sodium sulfate is used to adjust the osmolarity of the pharmaceutical composition to about 300 mOsm/Kg.

In some embodiments, sodium chloride is used to adjust the osmolality of the pharmaceutical composition to about 150 to about 1200 mOsm/Kg, for example to about 200 mOsm/Kg to about 800 mOsm/Kg. In some embodiments, sodium chloride is used to adjust the osmolarity of the pharmaceutical composition to about 300 mOsm/Kg.

In some embodiments, sodium sulfate is used to adjust the osmolality of the pharmaceutical composition to about 150 to about 1200 mOsm/Kg, for example to about 200 mOsm/Kg to about 800 mOsm/Kg. In some embodiments, sodium sulfate is used to adjust the osmolarity of the pharmaceutical composition to about 300 mOsm/Kg.

In some embodiments, the pharmaceutical formulations described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises (i) poloxamer 237 in an amount of about 0.01% to about 1.5% (e.g., or about 0.01% to about 1.0%, e.g., 0.5%) weight/volume relative to the volume of the pharmaceutical formulation, (ii) hydroxypropyl cellulose in an amount of about 0.01% to about 1.0% (e.g., about 0.05% to about 1.5%, e.g., about 0.1%) weight/volume relative to the volume of the pharmaceutical formulation, and (iii) sodium chloride in amount such that the pharmaceutical composition has an osmolarity of about 150 mOsm/Kg to about 1200 mOsm/Kg (e.g., about 200 mOsm/Kg to about 800 mOsm/Kg, e.g., 300 mOsm/Kg).

In some embodiments, the pharmaceutical formulations described herein comprise the compound of Formula I, Formula Ia, or Formula Ib (e.g., Formula Ia) in an amount of about 10 to about 40 mg (e.g., about 15 mg) per one mL of the pharmaceutical formulation and an aqueous vehicle, wherein the aqueous vehicle comprises (i) polysorbate 80 (Tween 80) in an amount of about 0.01% to about 1.0% (e.g., about 0.01% to about 0.05%, e.g., about 0.02%) weight/volume relative to the volume of the pharmaceutical formulation, (ii) hydroxypropyl cellulose in an amount of about 0.01% to about 1.0% (e.g., about 0.05% to about 1.5%, e.g., about 0.1%) weight/volume relative to the volume of the pharmaceutical formulation, and (iii) sodium chloride in amount such that the pharmaceutical composition has an osmolarity of about 150 mOsm/Kg to about 1200 mOsm/Kg (e.g., about 200 mOsm/Kg to about 800 mOsm/Kg, e.g., 300 mOsm/Kg).

6. Buffering Agent

In some embodiments, the pharmaceutical formulations described herein may also comprise a pH adjusting agent (or a buffering agent). The buffering agent are used to adjust or maintain the pH of pharmaceutical composition to a desired range for one or more of the following reasons: (1) to provide an environment for a better product stability, (2) to provide better comfort for the patient at administration (extreme pH may create irritation and/or discomfort to the site of administration), and (3) to provide a pH range for better anti-microbial preservative activity.

The pharmaceutical formulations of the disclosure may be formulated with one or more pharmaceutically acceptable buffering agents so that, the pH of the pharmaceutical composition is between about 3 to about 8, for example between 3 to about 7, between 3 to about 6.5, between 3 to about 6.0, between 3 to about 5.5, between 3 to about 5, between 4 to about 5. Examples of the buffering agents that may be used include, but are not limited to, hydrochloric acid, sulfuric acid, nitric acid, acetic acid, phosphoric acid, fumaric acid, citric acid, tartaric acid, maleic acid, succinic acid, ammonia solution, ammonium carbonate, sodium borate, sodium carbonate, triethanolamine, trolamine and sodium hydroxide.

In some embodiments, the buffering agent is a citrate buffer, which may also act as a taste masking agent or a flavoring agent. In some embodiments, the pharmaceutical composition has a pH of about 3 to about 6.5 and the buffering agent is a citrate buffer. Any pharmaceutically acceptable citrate buffer may be used in the pharmaceutical formulations disclosed herein. In some embodiments, the citrate buffer comprises sodium citrate, potassium citrate, citric acid or a combination thereof. It some examples the citrate buffer comprises sodium citrate. In some embodiments, the citrate buffer be generated from a mixture of sodium citrate and citric acid. It some examples the citrate buffer comprises potassium citrate. In some embodiments, the citrate buffer be generated from a mixture of potassium citrate and citric acid.

In some embodiments, the buffering agent is a phosphate buffer. In some embodiments, the pharmaceutical composition has a pH of about 6 to about 8 and the buffering agent is a phosphate buffer. Any pharmaceutically acceptable phosphate buffer may be used in the pharmaceutical formulations disclosed herein. In some embodiments, the phosphate buffer comprises sodium phosphate monobasic, potassium phosphate monobasic, sodium phosphate dibasic, potassium phosphate dibasic, phosphoric acid or a combination thereof.

7. Cyclodextrin

In some embodiments, the pharmaceutical formulations described herein further comprise a cyclodextrin. Cyclodextrin is a chemical family of cyclic compound typically having 6, 7, or 8 sugar units. In some embodiments, the cyclodextrin comprises 6 sugar units (an alpha-cyclodextrin (α-cyclodextrin)). In some embodiments, the cyclodextrin comprises 7 sugar units (beta-cyclodextrin (β-cyclodextrin)). In some embodiments, the cyclodextrin comprises a 8 sugar units (gamma-cyclodextrin (γ-cyclodextrin)).

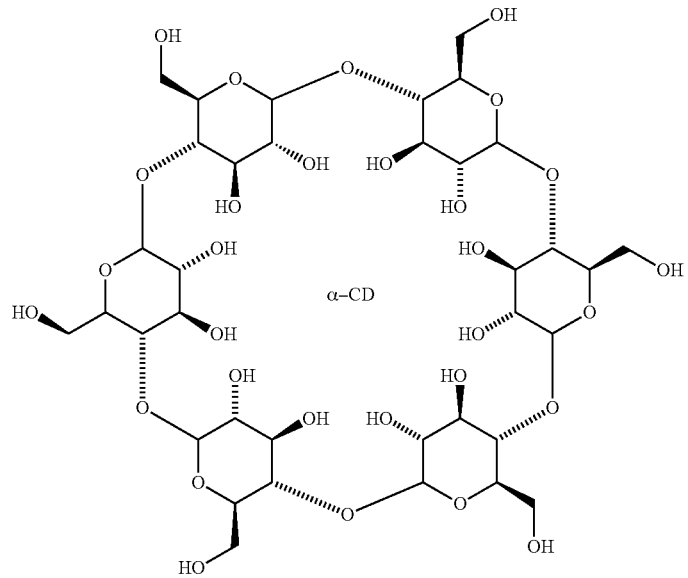

-continued

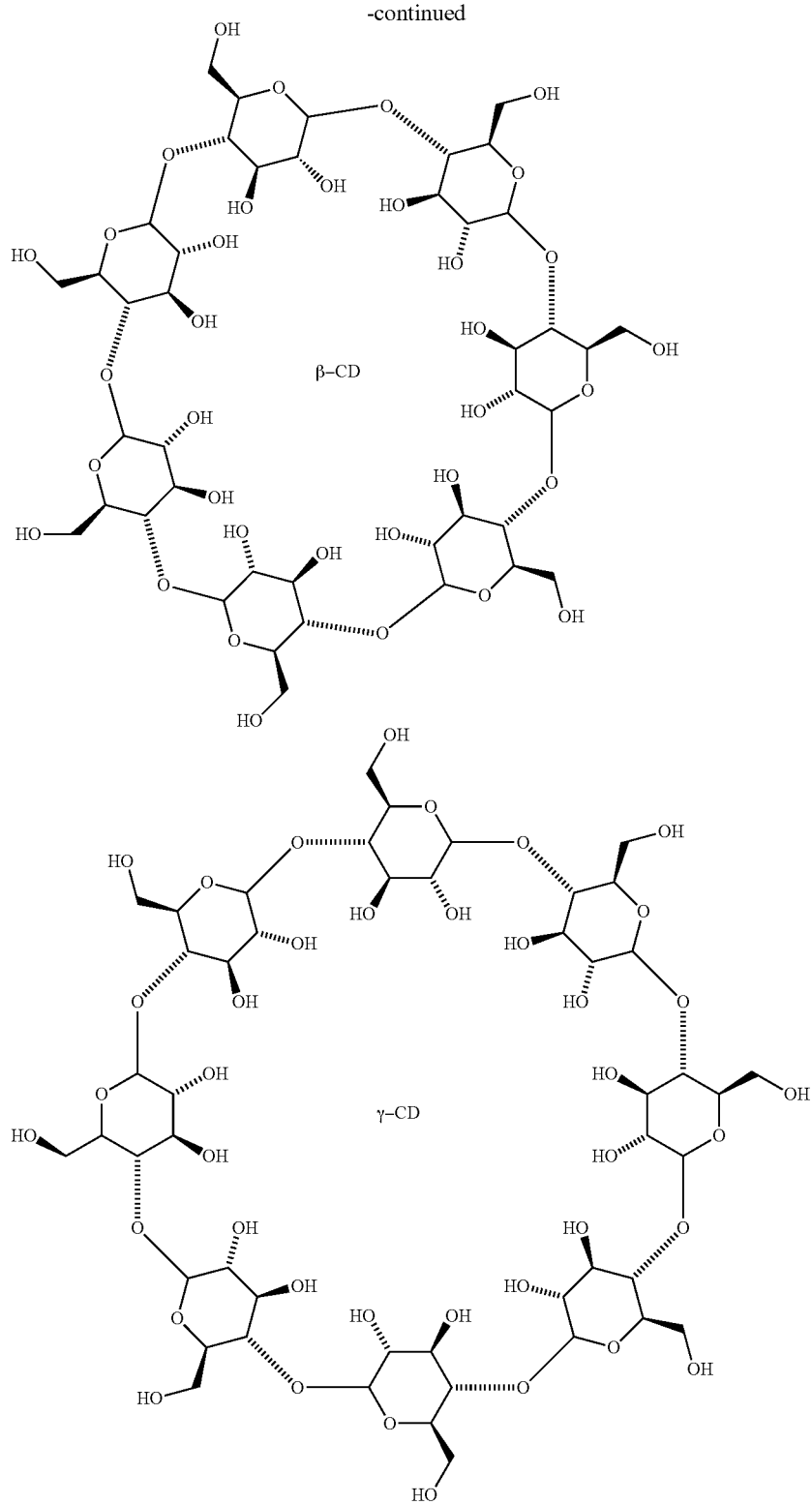

β-CD

γ-CD

In some embodiments, the pharmaceutical formulations described herein comprise a cyclodextrin derivative. Cyclodextrin derivatives are cyclodextrins where one or more of the —OH groups are modified to —OR groups. Non-limiting examples of cyclodextrin derivatives include, but are not limited to, cyclodextrins where —OH groups are modified to —OR wherein each R is independently alkyl, hydroxyalkyl, glucosyl or maltosyl groups, or —(CH$_2$)$_4$SO$_3^-$Na$^+$.

Non-limiting examples of commercial cyclodextrin derivatives that me be used in the pharmaceutical formulations described herein include, but are not limited to, CAPTISOL®, CAVITRON®, DEXOLVE-7®, and KLEP- TOSE®. CAPTISOL® (herein referred to as Captisol) is a registered trademark of Ligand Corporation. Captisol refers to sulfobutylalkylether-beta-cyclodextrin (sodium sulfonate salt) sold by or licensed by Ligand Pharmaceuticals. CAVITRON® (herein referred to as Cavitron) is a registered trademark of Wacker Chemie AG. Cavitron is an excipient obtained by the substitution of hydroxyl groups on native cyclodextrins to make hydroxypropyl-beta-cyclodextrins (HPBCD), a process that significantly enhance their solubility and makes them more suitable for drug solubilization. DEXOLVE-7® (herein referred to as Dexolve-7) is a registered trademark of CycloLabs Limited. Dexolve-7 is sulfobutylalkylether-beta-cyclodextrin sodium salt, an excipient used in pharmaceutical formulations to improve solubility. KLEPTOSE® (herein referred to as Kleptose) is a registered trademark of Roquette Pharmaceuticals, Geneva, Ill., USA. Kleptose is a brand of hydroxypropyl-beta-cyclodextrin.

In some embodiments, the cyclodextrin used in the pharmaceutical formulations described herein is a beta-cyclodextrin derivative selected from the group consisting of sulfobutylalkylether-beta-cyclodextrin, betadex-sulfobutylether sodium, and hydroxypropyl-beta-cyclodextrin. In some embodiments, the cyclodextrin is sulfobutylalkylether-beta-cyclodextrin. In some embodiments, cyclodextrin is betadex-sulfobutylether sodium. In some embodiments, cyclodextrin is hydroxypropyl-beta-cyclodextrin. In some embodiments, cyclodextrin has a formula:

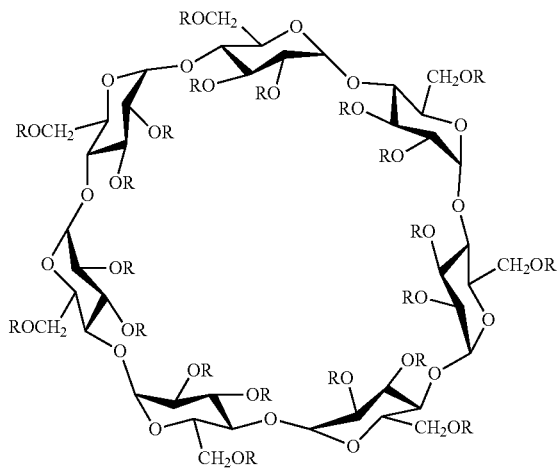

wherein R is —H or $CH_2CH_2CH_2CH_2SO_3^-Na^+$.

In some embodiments, the pharmaceutical formulations described herein comprise the compound of Formula I, Formula Ia or Formula Ib, or a pharmaceutically acceptable salt thereof, water, cyclodextrin, and, optionally, pH adjusting agents. In some embodiments, the pharmaceutical formulations described herein comprise the compound of Formula Ia, or a pharmaceutically acceptable salt thereof, water, cyclodextrin, and, optionally, pH adjusting agents.

In some embodiments, the pharmaceutical compositions described herein comprise the compound of Formula I, Formula Ia, or Formula Ib, or a pharmaceutically acceptable salt thereof, water, beta-cyclodextrin, and, optionally, pH adjusting agents. In some embodiments, the pharmaceutical compositions described herein comprise the compound of Formula Ia, or a pharmaceutically acceptable salt thereof, water, beta-cyclodextrin, and, optionally, pH adjusting agents.

In some embodiments, the pharmaceutical compositions described herein comprise the compound of Formula I, Formula Ia, or Formula Ib, or a pharmaceutically acceptable salt thereof, water, beta-cyclodextrin, and, optionally, pH adjusting agents, wherein the beta-cyclodextrin is sulfobutylalkylether-beta-cyclodextrin, betadex-sulfobutylether sodium, or hydroxypropyl-beta-cyclodextrin. In some embodiments, the pharmaceutical compositions described herein comprise the compound of Formula Ia, or a pharmaceutically acceptable salt thereof, water, and beta-cyclodextrin, and, optionally, pH adjusting agents, wherein the beta-cyclodextrin is sulfobutylalkylether-beta-cyclodextrin, betadex-sulfobutylether sodium, or hydroxypropyl-beta-cyclodextrin.

In some embodiments, the pharmaceutical compositions described herein comprise the compound of Formula I, Formula Ia, or Formula Ib, or a pharmaceutically acceptable salt thereof, water, and beta-cyclodextrin, and, optionally, pH adjusting agents, wherein the beta-cyclodextrin is betadex-sulfobutylether sodium. In some embodiments, the pharmaceutical compositions described herein comprise the compound of Formula Ia, or a pharmaceutically acceptable salt thereof, water, and beta-cyclodextrin, and, optionally, pH adjusting agents, wherein the beta-cyclodextrin is betadex-sulfobutylether sodium.

In some embodiments, the pharmaceutical compositions described herein comprise a compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise a compound of Formula Ia, or a pharmaceutically acceptable salt thereof, water, and beta-cyclodextrin, and, optionally, pH adjusting agents, wherein the pH adjusting agents are NaOH and HCl.

In some embodiments, the pharmaceutical compositions described herein comprise a compound of Formula I, Formula Ia or Formula Ib, or a pharmaceutically acceptable salt thereof, water, beta-cyclodextrin, and at least one pH adjusting agent. In some embodiments, the pharmaceutical formulations described herein comprise a compound of Formula I, Formula Ia or Formula Ib, or a pharmaceutically acceptable salt thereof, water, beta-cyclodextrin, and at least two pH adjusting agent. In some embodiments, the pharmaceutical formulations described herein comprise a compound of Formula I, Formula Ia or Formula Ib, or a pharmaceutically acceptable salt thereof, water, beta-cyclodextrin, and the pH adjusting agents HCl and NaOH.

In some embodiments, the pharmaceutical compositions described herein comprise a compound of Formula Ia, or a pharmaceutically acceptable salt thereof, water, beta-cyclodextrin, and at least one pH adjusting agent. In some embodiments, the pharmaceutical formulations described herein comprise a compound of Formula Ia, or a pharmaceutically acceptable salt thereof, water, beta-cyclodextrin, and at least two pH adjusting agent. In some embodiments, the pharmaceutical formulations described herein comprise a compound of Formula Ia, or a pharmaceutically acceptable salt thereof, water, beta-cyclodextrin, and the pH adjusting agents HCl and NaOH.

In some embodiments, the pharmaceutical compositions described herein comprise 90 mg to 175 mg of the compound of Formula I, Formula Ia, or Formula Ib, or a pharmaceutically acceptable salt thereof, water, and beta-cyclodextrin, and, optionally, pH adjusting agents. In some embodiments, the pharmaceutical compositions described herein 90 mg to 110 mg of Formula I, Formula Ia, or Formula Ib, or a pharmaceutically acceptable salt thereof, water, and beta-cyclodextrin, and, optionally, pH adjusting agents. In some embodiments, the pharmaceutical compositions described herein comprise 145 mg to 165 mg of the compound of Formula I, Formula Ia, or Formula Ib, or a pharmaceutically acceptable salt thereof, water, and beta-cyclodextrin, and, optionally, pH adjusting agents. In some embodiments, a composition comprising 100 mg of the compound of Formula I, Formula Ia, or Formula Ib, or a pharmaceutically acceptable salt thereof, water, and beta-cyclodextrin, and, optionally, pH adjusting agents. In some embodiments, the pharmaceutical compositions described herein comprise 150 mg of the compound of Formula I, Formula Ia, or Formula Ib, or a pharmaceutically acceptable salt thereof, water, and beta-cyclodextrin, and, optionally, pH adjusting agents.

In some embodiments, the pharmaceutical compositions described herein comprise 90 mg to 175 mg of the compound of Formula Ia, or a pharmaceutically acceptable salt thereof, water, and beta-cyclodextrin, and, optionally, pH adjusting agents. In some embodiments, the pharmaceutical compositions described herein 90 mg to 110 mg of Formula Ia, or a pharmaceutically acceptable salt thereof, water, and beta-cyclodextrin, and, optionally, pH adjusting agents. In some embodiments, the pharmaceutical compositions described herein comprise 145 mg to 165 mg of the compound of Formula Ia, or a pharmaceutically acceptable salt thereof, water, and beta-cyclodextrin, and, optionally, pH adjusting agents. In some embodiments, a composition comprising 100 mg of the compound of Formula Ia, or a pharmaceutically acceptable salt thereof, water, and beta-cyclodextrin, and, optionally, pH adjusting agents. In some embodiments, the pharmaceutical compositions described herein comprise 150 mg of the compound of Formula Ia, or a pharmaceutically acceptable salt thereof, water, and beta-cyclodextrin, and, optionally, pH adjusting agents.

In some embodiments, the pharmaceutical compositions described herein comprise 90 mg to 175 mg of the compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 90 mg to 110 mg of the compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 145 mg to 165 mg of the compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl. In some embodiments, the pharmaceutical compositions comprise 100 mg of the compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 150 mg of the compound of Formula I, Formula Ia, or Formula Ib, or a pharmaceutically acceptable salt thereof, water, and beta-cyclodextrin, and, optionally, pH adjusting agents, wherein the pH adjusting agents are NaOH and HCl.

In some embodiments, the pharmaceutical compositions described herein comprise 90 mg to 175 mg of the compound of Formula Ia, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 90 mg to 110 mg of the compound of Formula Ia, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 145 mg to 165 mg of the compound of Formula Ia, or a pharmaceutically acceptable salt thereof, water, and beta-cyclodextrin, and, optionally, pH adjusting agents, wherein the pH adjusting agents are NaOH and HCl. In some embodiments, the pharmaceutical compositions comprise 100 mg of the compound of Formula Ia, or a pharmaceutically acceptable salt thereof, water, and beta-cyclodextrin, and, optionally, pH adjusting agents, wherein the pH adjusting agents are NaOH and HCl. In some embodiments, the pharmaceutical compositions described herein comprise 150 mg of the compound of Formula Ia, or a pharmaceutically acceptable salt thereof, water, and beta-cyclodextrin, and, optionally, pH adjusting agents, wherein the pH adjusting agents are NaOH and HCl.

In some embodiments of the pharmaceutical formulations described herein, the cyclodextrin is present in an amount of about 5% to 30% w/v with respect to the volume of the pharmaceutical composition. In some embodiments, the cyclodextrin is present in an amount of about 10% to 25% w/v relative to the volume of the pharmaceutical composition. In some embodiments, the cyclodextrin is present in an amount of about 14% to 21% w/v relative to the volume of the pharmaceutical composition. In some embodiments, the cyclodextrin is present in an amount of about 15% w/v relative to the volume of the pharmaceutical composition. In some embodiments, the cyclodextrin is present in an amount of about 20% w/v relative to the volume of the pharmaceutical composition. In some embodiments, the cyclodextrin is present in an amount of 15% w/v relative to the volume of the pharmaceutical composition. In some embodiments, the cyclodextrin is present in an amount of 20% w/v relative to the volume of the pharmaceutical composition. In some embodiments, the cyclodextrin is present in an amount of about 5% to 15% w/v relative to the volume of the pharmaceutical composition. In some embodiments, the cyclodextrin is present in an amount of 8% to 12% w/v relative to the volume of the pharmaceutical composition. In some embodiments, the cyclodextrin is present in an amount of 10% w/v relative to the volume of the pharmaceutical composition.

In some embodiments of the pharmaceutical formulations described herein, the beta-cyclodextrin is present in an amount of about 5% to 30% w/v relative to the volume of the pharmaceutical composition. In some embodiments, the beta-cyclodextrin is present in an amount of about 10% to 25% w/v relative to the volume of the pharmaceutical composition. In some embodiments, the beta-cyclodextrin is present in an amount of about 14% to 21% w/v relative to the volume of the pharmaceutical composition. In some embodiments, the beta-cyclodextrin is present in an amount of about 15% w/v relative to the volume of the pharmaceutical composition. In some embodiments, the beta-cyclodextrin is present in an amount of about 20% w/v relative to the volume of the pharmaceutical composition. In some embodiments, the beta-cyclodextrin is present in an amount of 15% w/v relative to the volume of the pharmaceutical composition. In some embodiments, the beta-cyclodextrin is present in an amount of 20% w/v relative to the volume of the pharmaceutical composition. In some embodiments, the beta-cyclodextrin is present in an amount of about 5% to 15% w/v relative to the volume of the pharmaceutical composition. In some embodiments, the beta-cyclodextrin is present in an amount of 8% to 12% w/v relative to the volume of the pharmaceutical composition. In some embodiments, the beta-cyclodextrin is present in an amount of 10% w/v relative to the volume of the pharmaceutical composition.

In some embodiments of the pharmaceutical formulations provided herein, the compound of Formula I, Formula Ia, or Formula Ib is present in an amount of about 1.0 to 10.0 mg/mL. In some embodiments, the compound of Formula I, Formula Ia, or Formula Ib is present in an amount of about 4.0 to 8.0 mg/mL. In some embodiments, the compound of Formula I, Formula Ia, or Formula Ib is present in an amount of about 5.0 to 7.0 mg/mL. In some embodiments, the compound of Formula I, Formula Ia, or Formula Ib is present in an amount of about 5.0 mg/mL. In some embodiments, the compound of Formula I, Formula Ia, or Formula Ib is present in an amount of about 6.7 mg/mL. In some embodiments, the compound of Formula I, Formula Ia, or Formula Ib is present an amount of 5.0 mg/mL. In some embodiments, the compound of Formula I, Formula Ib, or Formula Ib is present an amount of 6.7 mg/mL.

In some embodiments of the pharmaceutical formulations provided herein, the compound of Formula Ia is present in an amount of about 1.0 to 10.0 mg/mL. In some embodiments, the compound of Formula Ia is present in an amount of about 4.0 to 8.0 mg/mL. In some embodiments, the compound of Formula Ia is present in an amount of about 5.0 to 7.0 mg/mL. In some embodiments, the compound of Formula Ia is present in an amount of about 5.0 mg/mL. In some embodiments, the compound of Formula Ia is present in an amount of about 6.7 mg/mL. In some embodiments, the compound of Formula Ia is present an amount of 5.0 mg/mL. In some embodiments, the compound of Formula Ia is present an amount of 6.7 mg/mL.

In some embodiments, the pharmaceutical compositions described herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib, or the pharmaceutically acceptable salt thereof, is present in an amount of about 4.0 to 8.0 mg/mL and the beta-cyclodextrin is present in an amount of about 5% to 30% w/v. In some embodiments, the pharmaceutical compositions described herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia or Formula Ib, or the pharmaceutically acceptable salt thereof is present in an amount of about 4.0 to 8.0 mg/mL and the beta-cyclodextrin is present in an amount of about 10% to 25% w/v. In some embodiments, the pharmaceutical composition described herein comprise the compound of Formula I, Formula Ia or Formula Ib, or a pharmaceutically acceptable salt thereof, water, and beta-cyclodextrin, and, optionally, pH adjusting agents, wherein the compound of Formula I, Formula Ia, or Formula Ib, or the pharmaceutically acceptable salt thereof, is present in an amount of about 4.0 to 8.0 mg/mL and the beta-cyclodextrin is present in an amount of about 14% to 21% w/v. In some embodiments, the pharmaceutical composition described herein comprise the compound of Formula I, Formula Ia or Formula Ib, or a pharmaceutically acceptable salt thereof, water, and beta-cyclodextrin, and, optionally, pH adjusting agents, wherein the compound of Formula I, Formula Ia, or Formula Ib, or the pharmaceutically acceptable salt thereof, is present in an amount of about 4.0 to 8.0 mg/mL and the beta-cyclodextrin is present in an amount of about 5% to 15% w/v. In some embodiments, the compound of Formula I, Formula Ia, or Formula Ib, or the pharmaceutically acceptable salt thereof, is present in an amount of about 4.0 to 8.0 mg/mL and the beta-cyclodextrin is present in an amount of about 8% to 12% w/v. In some embodiments, the compound of Formula I, Formula Ia, or Formula Ib, or the pharmaceutically acceptable salt thereof, is present in an amount of about 5.0 to 7.0 mg/mL and the beta-cyclodextrin is present in an amount of about 5% to 15% w/v. In some embodiments, the compound of Formula I, Formula Ia, or Formula Ib, or the pharmaceutically acceptable salt thereof, is present in an amount of about 5.0 to 7.0 mg/mL and the beta-cyclodextrin is present in an amount of about 8% to 12% w/v. In some embodiments, the compound of Formula I, Formula Ia, or Formula Ib, or the pharmaceutically acceptable salt thereof, is present in an amount of about 6.0 to 7.0 mg/mL and the beta-cyclodextrin is present in an amount of about 10% w/v.

In some embodiments, the pharmaceutical composition described herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 4.0 to 8.0 mg/mL and the beta-cyclodextrin is present in an amount of about 5% to 15% w/v. In some embodiments, the compound of Formula Ia, or the pharmaceutically acceptable salt thereof, is present in an amount of about 4.0 to 8.0 mg/mL and the beta-cyclodextrin is present in an amount of about 8% to 12% w/v. In some embodiments, the compound of Formula Ia, or the pharmaceutically acceptable salt thereof, is present in an amount of about 5.0 to 7.0 mg/mL and the beta-cyclodextrin is present in an amount of about 5% to 15% w/v. In some embodiments, the compound of Formula Ia, or the pharmaceutically acceptable salt thereof, is present in an amount of about 5.0 to 7.0 mg/mL and the beta-cyclodextrin is present in an amount of about 8% to 12% w/v. In some embodiments, the compound of Formula Ia, or the pharmaceutically acceptable salt thereof, is present in an amount of about 6.0 to 7.0 mg/mL and the beta-cyclodextrin is present in an amount of about 10% w/v.

In some embodiments, the pharmaceutical compositions described herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 4.0 to 8.0 mg/mL and the beta-cyclodextrin is present in an amount of about 5% to 30% w/v. In some embodiments, the pharmaceutical compositions described herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof is present in an amount of about 4.0 to 8.0 mg/mL and the beta-cyclodextrin is present in an amount of about 10% to 25% w/v. In some embodiments, the pharmaceutical composition described herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 4.0 to 8.0 mg/mL and the beta-cyclodextrin is present in an amount of about 14% to 21% w/v.

In some embodiments, the pharmaceutical compositions provided herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib is present in an amount of about 5.0 to 7.0 mg/mL and the beta-cyclodextrin is present in an amount of about 5% to 30% w/v relative to the volume of the pharmaceutical composition. In some embodiments, the pharmaceutical compositions disclosed herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib is present in an amount of about 5.0 to 7.0 mg/mL and the beta-cyclodextrin is present in an amount of about 10% to 25% w/v relative to the volume of the pharmaceutical composition. In some embodiments, the pharmaceutical compositions disclosed herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib is present in an amount of about 5.0 to 7.0 mg/mL and the beta-cyclodextrin is present in an amount of about 14% to 21% w/v relative to the volume of the pharmaceutical composition.

In some embodiments, the pharmaceutical compositions provided herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 5.0 to 7.0 mg/mL and the beta-cyclodextrin is present in an amount of about 5% to 30% w/v relative to the volume of the pharmaceutical composition. In some embodiments, the pharmaceutical compositions disclosed herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 5.0 to 7.0 mg/mL and the beta-cyclodextrin is present in an amount of about 10% to 25% w/v relative to the volume of the pharmaceutical composition. In some embodiments, the pharmaceutical compositions disclosed herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 5.0 to 7.0 mg/mL and the beta-cyclodextrin is present in an amount of about 14% to 21% w/v relative to the volume of the pharmaceutical composition.

In some embodiments, the pharmaceutical compositions disclosed herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib, or the pharmaceutically acceptable salt thereof, is present in an amount of about 5.0 mg/mL and the beta-cyclodextrin is present in an amount of about 15% w/v relative to the volume of the pharmaceutical composition. In some embodiments, the pharmaceutical compositions disclosed herein comprise the compound of Formula I, Formula Ia, or Formula Ib, or a pharmaceutically acceptable salt thereof, water, and beta-cyclodextrin, and, optionally, pH adjusting agents, wherein the compound of Formula I, Formula Ia, or Formula Ib, or the pharmaceutically acceptable salt thereof, is present in an amount of about 6.7 mg/mL and the beta-cyclodextrin is present in an amount of about 20% w/v relative to the volume of the pharmaceutical composition.

In some embodiments, the pharmaceutical compositions disclosed herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 5.0 mg/mL and the beta-cyclodextrin is present in an amount of about 15% w/v relative to the volume of the pharmaceutical composition. In some embodiments, the pharmaceutical compositions disclosed herein comprise the compound of Formula Ia, or a pharmaceutically acceptable salt thereof, water, and beta-cyclodextrin, and, optionally, pH adjusting agents, wherein the compound of Formula Ia, or the pharmaceutically acceptable salt thereof, is present in an amount of about 6.7 mg/mL and the beta-cyclodextrin is present in an amount of about 20% w/v relative to the volume of the pharmaceutical composition.

In some embodiments, the pharmaceutical formulations for inhalation, disclosed herein are obtained by reconstitution of a solid or a powdered formulation. In some examples, the pharmaceutical formulations, for inhalation disclosed herein are obtained by reconstitution of lyophilized formulations, for example by reconstitution of the lyophilized formulations disclosed WO2019/014247.

Lyophilized Formulations

In some embodiments, the pharmaceutical formulations, for inhalation, disclosed herein are obtained by reconstitution of a lyophilized or dehydrated composition comprising the compound of Formula I, Formula Ia, or Formula Ib, or a pharmaceutically acceptable salt thereof, and cyclodextrin. In some embodiments, the pharmaceutical formulations, for inhalation, disclosed herein are obtained by reconstitution of a lyophilized composition comprising the compound of Formula Ia, or a pharmaceutically acceptable salt thereof, and cyclodextrin. The lyophilized composition can be in any suitable solid form, such as a powder.

The compound of Formula I, Formula Ia, or Formula Ib can be present in the lyophilized composition in an amount from 1% to 10% w/w, for example from 1 to 5%, or from 2 to 4%, or from 3 to 4%, or from 3 to 3.5% w/w. In some embodiments, the lyophilized composition comprises the compound of Formula I, Formula Ia, or Formula Ib in an amount from 1% to 10% w/w. In some embodiments, the lyophilized composition comprises the compound of Formula I, Formula Ia, or Formula Ib in an amount from 1% to 5% w/w. In some embodiments, the lyophilized composition comprises the compound of Formula I, Formula Ia, or Formula Ib in an amount from 2% to 4% w/w. In some embodiments, the lyophilized composition comprises the compound of Formula I, Formula Ia, or Formula Ib in an amount from 3% to 3.5% w/w.

In some embodiments, the lyophilized composition comprises the compound of Formula Ia, or a pharmaceutically acceptable salt thereof, in an amount of 1% to 10% w/w, for example 1 to 5%, 2 to 4%, 3 to 4%, or 3 to 3.5% w/w. In some embodiments, the lyophilized composition comprises the compound of Formula Ia, or a pharmaceutically acceptable salt thereof, in an amount of 1% to 10% w/w. In some embodiments, the lyophilized composition comprise the compound of Formula Ia, or a pharmaceutically acceptable salt thereof, in an amount of 1% to 5% w/w. In some embodiments, the lyophilized composition comprises the compound of Formula Ia, or a pharmaceutically acceptable salt thereof, in an amount of 2% to 4% w/w. In some embodiments, the lyophilized composition comprises the compound of Formula Ia, or a pharmaceutically acceptable salt thereof, in an amount of 3% to 3.5% w/w.

In some embodiments, the lyophilized formulations comprise the compound of Formula I, Formula Ia, or Formula Ib in an amount of about 1% to 10% w/w relative to the weight of the pharmaceutical formulation, for example about 1 to 5% w/w, about 2 to 4% w/w, about 3 to 4%, w/w or about 3 to 3.5% w/w. In some embodiments, the lyophilized composition comprise the compound of Formula I, Formula Ia, or Formula Ib in an amount of about 1% to 10% w/w relative to the weight of the pharmaceutical formulation. In some embodiments, the lyophilized composition comprises the compound of Formula I, Formula Ia, or Formula Ib in an amount of about 1% to 5% w/w. In some embodiments, the lyophilized composition comprises the compound of Formula I, Formula Ia, or Formula Ib in an amount of about 2% to 4% w/w. In some embodiments, the lyophilized composition comprises the compound of Formula I, Formula Ia, or Formula Ib in an amount of about 3% to 3.5% w/w.

In some embodiments, the lyophilized formulations comprise the compound of Formula Ia in an amount of about 1% to 10% w/w relative to the weight of the pharmaceutical formulation, for example about 1 to 5% w/w, about 2 to 4% w/w, about 3 to 4%, w/w or about 3 to 3.5% w/w. In some embodiments, the lyophilized composition comprise the compound of Formula Ia in an amount of about 1% to 10% w/w relative to the weight of the pharmaceutical formulation. In some embodiments, the lyophilized composition comprises the compound of Formula Ia in an amount of about 1% to 5% w/w. In some embodiments, the lyophilized composition comprises the compound of Formula Ia in an amount of about 2% to 4% w/w. In some embodiments, the lyophilized composition comprises the compound of Formula Ia in an amount of about 3% to 3.5% w/w.

In some embodiments, the lyophilized compositions comprise the compound of Formula I, Formula Ia, or Formula Ib, or a pharmaceutically acceptable salt thereof, in an amount of about 1% w/w, 1.5% w/w, 2% w/w, 2.1% w/w, 2.2% w/w, 2.3% w/w, 2.4% w/w, 2.5% w/w, 2.6% w/w, 2.7% w/w, 2.8% w/w, 3.9% w/w, 3% w/w, 3.1% w/w, 3.2% w/w, 3.3% w/w, 3.4% w/w, 3.5% w/w, 3.6% w/w, 3.7% w/w, 3.8% w/w, 3.9% w/w, 4% w/w, 4.5% w/w, 5% w/w, 6% w/w, 7% w/w, 8% w/w, 9% w/w, or about 10% w/w. In some embodiments, the lyophilized composition comprise the Formula I, Formula Ia, or Formula Ib in an amount of about 3.2% w/w.

In some embodiments, the lyophilized compositions comprise the compound of Formula Ia in an amount of about 1% w/w, 1.5% w/w, 2% w/w, 2.1% w/w, 2.2% w/w, 2.3% w/w, 2.4% w/w, 2.5% w/w, 2.6% w/w, 2.7% w/w, 2.8% w/w, 3.9% w/w, 3% w/w, 3.1% w/w, 3.2% w/w, 3.3% w/w, 3.4% w/w, 3.5% w/w, 3.6% w/w, 3.7% w/w, 3.8% w/w, 3.9% w/w, 4% w/w, 4.5% w/w, 5% w/w, 6% w/w, 7% w/w, 8% w/w, 9% w/w, or about 10% w/w. In some embodiments, the lyophilized composition comprise the Formula Ia in an amount of about 3.2% w/w.

In some embodiments, cyclodextrin is present in the lyophilized composition in an amount of about 90% to 99% w/w, for example about 95 to 99% w/w, about 96 to 98% w/w, or about 96.5 to 97% w/w. In some embodiments, the lyophilized composition comprises cyclodextrin in an amount of about 90% to 99% w/w. In some embodiments, the lyophilized composition comprises cyclodextrin in an amount of about 95 to 99% w/w. In some embodiments, the lyophilized composition comprises cyclodextrin in an amount of about 96 to 98% w/w. In some embodiments, the lyophilized composition comprises cyclodextrin in an amount of about 96.5 to 97% w/w.

In some embodiments, the lyophilized composition comprises cyclodextrin in an amount of about 90% w/w, about 91% w/w, about 92% w/w, about 93% w/w, about 94% w/w, about 95% w/w, about 95.1% w/w, about 95.2% w/w, about 95.3% w/w, about 95.4% w/w, about 95.5% w/w, about 95.6% w/w, about 95.7% w/w, about 95.8% w/w, about 95.9% w/w, about 96% w/w, about 96.1% w/w, about 96.2% w/w, about 96.3% w/w, about 96.4% w/w, about 96.5% w/w, about 96.6% w/w, about 96.7% w/w, about 96.8% w/w, about 96.9% w/w, about 97% w/w, about 97.1% w/w, about 97.2% w/w, about 97.3% w/w, about 97.4% w/w, about 97.5% w/w, about 97.6% w/w, about 97.7% w/w, about 97.8% w/w, about 97.9% w/w, about 98% w/w, or about 99% w/w. In some embodiments, the lyophilized composition comprises cyclodextrin in an amount of about 96.8% w/w. In some embodiments, the lyophilized composition comprises betadex-sulfobutylether sodium in an amount of about 96.8% w/w.

In some embodiments, the lyophilized composition comprises the compound of Formula I, Formula Ia, or Formula Ib in an amount of about 3.2% w/w, and cyclodextrin in an amount of about 96.8% w/w. In some embodiments, the lyophilized composition comprises the compound of Formula I, Formula Ia, or Formula Ib in an amount of about 3.2% w/w, and betadex-sulfobutylether sodium in an amount of about 96.8% w/w.

In some embodiments, the lyophilized composition comprises the compound of Formula Ia, in an amount of about 3.2% w/w, and cyclodextrin in an amount of about 96.8% w/w. In some embodiments, the lyophilized composition comprises the compound of Formula Ia, in an amount of about 3.2% w/w, and betadex-sulfobutylether sodium in an amount of about 96.8% w/w.

In some embodiments, the lyophilized composition comprises the compound of Formula I, Formula Ia, or Formula Ib in an amount from 1% to 10% w/w, for example from 1 to 5%, or from 2 to 4%, or from 3 to 4%, or from 3 to 3.5%, and cyclodextrin in an amount from 90% to 99% w/w, for example from 95 to 99%, or from 96 to 98%, or from 96.5 to 97% w/w. In some embodiments, the lyophilized composition comprises the compound of Formula I, Formula Ia, or Formula Ib in an amount of 1% to 10% w/w, and cyclodextrin in an amount of 90% to 99% w/w. In some embodiments, the lyophilized composition include the compound of Formula I, Formula Ia, or Formula Ib in an amount of 1% to 5% w/w, and cyclodextrin in an amount of 95 to 99% w/w. In some embodiments, the lyophilized composition comprises the compound of Formula I, Formula Ia, or Formula Ib in an amount of about 2% to 4% w/w, and cyclodextrin in an amount from 96 to 98% w/w. In some embodiments, the lyophilized composition comprises the compound of Formula I, Formula Ia, or Formula Ib in an amount of 3% to 3.5% w/w, and cyclodextrin in an amount of 96.5 to 97% w/w.

In some embodiments, the lyophilized composition comprises the compound of Formula Ia in an amount from 1% to 10% w/w, for example from 1 to 5%, or from 2 to 4%, or from 3 to 4%, or from 3 to 3.5%, and cyclodextrin in an amount from 90% to 99% w/w, for example from 95 to 99%, or from 96 to 98%, or from 96.5 to 97% w/w. In some embodiments, the lyophilized composition comprises the compound of Formula Ia in an amount of 1% to 10% w/w, and cyclodextrin in an amount of 90% to 99% w/w. In some embodiments, the lyophilized composition comprises the compound of Formula Ia in an amount of 1% to 5% w/w, and cyclodextrin in an amount of 95 to 99% w/w. In some embodiments, the lyophilized composition comprises the compound of Formula Ia in an amount of about 2% to 4% w/w, and cyclodextrin in an amount from 96 to 98% w/w. In some embodiments, the lyophilized composition comprises the compound of Formula Ia in an amount of 3% to 3.5% w/w, and cyclodextrin in an amount of 96.5 to 97% w/w.

In some embodiments, the lyophilized composition comprises the compound of Formula I, Formula Ia, or Formula Ib in an amount of about 3.2% w/w and cyclodextrin in an amount of about 96.8% w/w. In some embodiments, the lyophilized composition comprises the compound of Formula I, Formula Ia, or Formula Ib at 3.2% w/w and cyclodextrin in an amount of 96.8% w/w. In some embodiments, the lyophilized composition consists essentially of the compound of Formula I, Formula Ia, or Formula Ib in an amount of about 3.2% w/w and cyclodextrin in an amount of about 96.8% w/w. In some embodiments, the lyophilized composition consists essentially of the compound of Formula I, Formula Ia, or Formula Ib at 3.2% w/w and cyclodextrin in an amount of 96.8% w/w.

In some embodiments, the lyophilized composition comprises the compound of Formula Ia in an amount of about 3.2% w/w and cyclodextrin in an amount of about 96.8% w/w. In some embodiments, the lyophilized composition comprises the compound of Formula Ia in an amount of 3.2% w/w and cyclodextrin in an amount of 96.8% w/w. In some embodiments, the lyophilized composition consists essentially of the compound of Formula Ia in an amount of about 3.2% w/w and cyclodextrin in an amount of about 96.8% w/w. In some embodiments, the lyophilized composition consists essentially of the compound of Formula Ia at 3.2% w/w and cyclodextrin in an amount of 96.8% w/w.

In some embodiments, the lyophilized composition comprises the compound of Formula I, Formula Ia, or Formula Ib in an amount of about 3.2% w/w and betadex-sulfobutylether sodium in an amount of about 96.8% w/w. In some embodiments, the lyophilized composition comprises the compound of Formula I, Formula Ia, or Formula Ib in an amount of 3.2% w/w and betadex-sulfobutylether sodium in an amount of 96.8% w/w. In some embodiments, the lyophilized composition consists essentially of the compound of Formula I, Formula Ia, or Formula Ib in an amount of about 3.2% w/w and betadex-sulfobutylether sodium in an amount of about 96.8% w/w. In some embodiments, the lyophilized composition consists essentially of the compound of Formula I, Formula Ia, or Formula Ib in an amount of 3.2% w/w and betadex-sulfobutylether sodium in an amount of 96.8% w/w.

In some embodiments, the lyophilized composition comprises the compound of Formula Ia in an amount of about 3.2% w/w and betadex-sulfobutylether sodium in an amount of about 96.8% w/w. In some embodiments, the lyophilized composition comprises the compound of Formula Ia in an amount of 3.2% w/w and betadex-sulfobutylether sodium in an amount of 96.8% w/w. In some embodiments, the lyophilized composition consists essentially of the compound of Formula Ia in an amount of about 3.2% w/w and betadex-sulfobutylether sodium in an amount of about 96.8% w/w. In some embodiments, the lyophilized composition consists essentially of the compound of Formula Ia in an amount of 3.2% w/w and betadex-sulfobutylether sodium in an amount of 96.8% w/w.

The cyclodextrin of the lyophilized composition can include any suitable cyclodextrin as described above. For example, the cyclodextrin can be a beta-cyclodextrin, such as sulfobutylalkylether-beta-cyclodextrin, betadex-sulfobutylether sodium, or hydroxypropyl-beta-cyclodextrin. In some embodiments, the lyophilized composition comprises a beta-cyclodextrin. In some embodiments, the lyophilized composition comprises sulfobutylalkylether-beta-cyclodextrin, betadex-sulfobutylether sodium, or hydroxypropyl-beta-cyclodextrin. In some embodiments, the lyophilized composition comprises betadex-sulfobutylether sodium.

In some embodiments, the lyophilized composition comprises the compound of Formula I, Formula Ia, or Formula Ib, or a pharmaceutically acceptable salt thereof, and beta-cyclodextrin, and, optionally, pH adjusting agents, wherein the amount of compound of Formula I, Formula Ia, or Formula Ib is 3%±1% w/w and the amount of beta-cyclodextrin is 97%±1% w/w. In some embodiments, the lyophilized composition comprises the compound of Formula I, Formula Ia, or Formula Ib, or a pharmaceutically acceptable salt thereof, and beta-cyclodextrin, and, optionally, pH adjusting agents, wherein the compound of Formula I, Formula Ia, or Formula Ib is present in an amount of about 3%±0.5% w/w and beta-cyclodextrin is present in an amount of about 97%±0.5% w/w. In some embodiments, the lyophilized composition comprises the compound of Formula I, Formula Ia, or Formula Ib, or a pharmaceutically acceptable salt thereof, and beta-cyclodextrin, and, optionally, pH adjusting agents, wherein the compound of Formula I, Formula Ia, or Formula Ib is present in an amount of about 3.2% w/w and beta-cyclodextrin is present in an amount of about 96.8% w/w.

In some embodiments, the lyophilized composition comprises the compound of Formula Ia, or a pharmaceutically acceptable salt thereof, and beta-cyclodextrin, and, optionally, pH adjusting agents, wherein the amount of compound of Formula Ia is present in an amount of about 3%±1% w/w and the amount of beta-cyclodextrin is present in an amount of 97%±1% w/w. In some embodiments, the lyophilized composition comprises the compound of Formula Ia, or a pharmaceutically acceptable salt thereof, and beta-cyclodextrin, and, optionally, pH adjusting agents, wherein the compound of Formula Ia is present in an amount of about 3%±0.5% w/w and beta-cyclodextrin is present in an amount of about 97%±0.5% w/w. In some embodiments, the lyophilized composition comprises the compound of Formula Ia, or a pharmaceutically acceptable salt thereof, and beta-cyclodextrin, and, optionally, pH adjusting agents, wherein the compound of Formula Ia is present in an amount of about 3.2% w/w and beta-cyclodextrin is present in an amount of about 96.8% w/w.

In some embodiments, the lyophilized composition comprises the compound of Formula I, Formula Ia, or Formula Ib, or a pharmaceutically acceptable salt thereof, in an amount of 5% to 10% w/w. In some embodiments, the compound of Formula I, Formula Ia, or Formula Ib, or a pharmaceutically acceptable salt thereof, is present in an amount of 5% to 7% w/w. In some embodiments, the compound of Formula I, Formula Ia, or Formula Ib, or a pharmaceutically acceptable salt thereof, is present in an amount of 6% to 7% w/w. In some embodiments, the compound of Formula I, Formula Ia, or Formula Ib, or a pharmaceutically acceptable salt thereof, is present in an amount of 6.0% to 6.5% w/w. In some embodiments, the compound of Formula I, Formula Ia, or Formula Ib, or a pharmaceutically acceptable salt thereof, is present in an amount of about 6.3% w/w.

In some embodiments, the lyophilized composition comprises the compound of Formula Ia, or a pharmaceutically acceptable salt thereof, in an amount of 5% to 10% w/w. In some embodiments, the lyophilized composition comprises the compound of Formula Ia, or a pharmaceutically acceptable salt thereof, in an amount of 5% to 7% w/w. In some embodiments, the lyophilized composition comprises the compound of Formula Ia, or a pharmaceutically acceptable salt thereof, in an amount of 6% to 7% w/w. In some embodiments, the lyophilized composition comprises the compound of Formula Ia, or a pharmaceutically acceptable salt thereof, in an amount of 6.0% to 6.5% w/w. In some embodiments, the lyophilized composition comprises the compound of Formula Ia, or a pharmaceutically acceptable salt thereof, in an amount of about 6.3% w/w.

In some embodiments, the lyophilized composition comprises the compound of Formula Ia in an amount of 5% to 10% w/w. In some embodiments, the lyophilized composition comprises the compound of Formula Ia in an amount of 5% to 7% w/w. In some embodiments, the lyophilized composition comprises the compound of Formula Ia in an amount of 6% to 7% w/w. In some embodiments, the lyophilized composition comprises the compound of Formula I in an amount of 6.0% to 6.5% w/w. In some embodiments, the lyophilized composition comprise the Formula I in an amount of about 6.3% w/w.

In some embodiments, the lyophilized composition comprises cyclodextrin in an amount of about 90 to 95% w/w. In some embodiments, the lyophilized composition comprises cyclodextrin in an amount of about 93 to 95% w/w. In some embodiments, the lyophilized composition comprises cyclodextrin in an amount of about 93 to 94% w/w. In some embodiments, the lyophilized composition comprises cyclodextrin in an amount of about 93.7% w/w. In some embodiments, the lyophilized composition comprises betadex-sulfobutylether sodium in an amount of about 93.7% w/w.

In some embodiments, the lyophilized composition comprises the compound of Formula I, Formula Ia, or Formula Ib, or a pharmaceutically acceptable salt thereof, in an amount of about 5-7% w/w, and cyclodextrin in an amount of about 93-95% w/w. In some embodiments, the lyophilized composition comprises the compound of Formula I, Formula Ia, or Formula Ib, or a pharmaceutically acceptable salt thereof, in an amount of about 5-7% w/w, and betadex-sulfobutylether sodium in an amount of about 93-95% w/w.

In some embodiments, the lyophilized composition comprises the compound of Formula I, Formula Ia, or Formula Ib in an amount of about 5-7% w/w, and cyclodextrin in an amount of about 93-95% w/w. In some embodiments, the lyophilized composition comprises the compound of Formula I, Formula Ia, or Formula Ib in an amount of about 5-7% w/w, and betadex-sulfobutylether sodium in an amount of about 93-95% w/w.

In some embodiments, the lyophilized composition comprises the compound of Formula Ia, or a pharmaceutically acceptable salt thereof, in an amount of about 5-7% w/w, and cyclodextrin in an amount of about 93-95% w/w. In some embodiments, the lyophilized composition comprises the compound of Formula Ia, or a pharmaceutically acceptable salt thereof, in an amount of about 5-7% w/w, and betadex-sulfobutylether sodium in an amount of about 93-95% w/w.

In some embodiments, the lyophilized composition comprises the compound of Formula Ia in an amount of 5-7% w/w, and cyclodextrin in an amount of about 93-95% w/w. In some embodiments, the lyophilized composition comprises the compound of Formula Ia in an amount of about 5-7% w/w, and betadex-sulfobutylether sodium in an amount of about 93-95% w/w.

In some embodiments, the lyophilized composition comprises the compound of Formula I, Formula Ia, or Formula Ib, or a pharmaceutically acceptable salt thereof, in an amount of about 6.3% w/w, and cyclodextrin in an amount of about 93.7% w/w. In some embodiments, the lyophilized composition comprises the compound of Formula I, Formula Ia, or Formula Ib, or a pharmaceutically acceptable salt thereof, in an amount of about 6.3% w/w, and betadex-sulfobutylether sodium in an amount of about 93.7% w/w.

In some embodiments, the lyophilized composition comprises the compound of Formula I, Formula Ia, or Formula Ib in an amount of about 6.3% w/w, and cyclodextrin in an amount of about 93.7% w/w. In some embodiments, the lyophilized composition comprises the compound of Formula I, Formula Ia, or Formula Ib in an amount of about 6.3% w/w, and betadex-sulfobutylether sodium in an amount of about 93.7% w/w.

In some embodiments, the lyophilized composition comprises the compound of Formula Ia, or a pharmaceutically acceptable salt thereof, in an amount of about 6.3% w/w, and cyclodextrin in an amount of about 93.7% w/w. In some embodiments, the lyophilized composition comprises the compound of Formula Ia, or a pharmaceutically acceptable salt thereof, in an amount of about 6.3% w/w, and betadex-sulfobutylether sodium in an amount of about 93.7% w/w.

In some embodiments, the lyophilized composition comprises the compound of Formula Ia in an amount of about 6.3% w/w, and cyclodextrin in an amount of about 93.7% w/w. In some embodiments, the lyophilized composition comprises the compound of Formula Ia in an amount of about 6.3% w/w, and betadex-sulfobutylether sodium in an amount of about 93.7% w/w.

The lyophilized composition can include various forms of the compound of Formula I, Formula Ia, or Formula Ib. For example, the compound of Formula I, Formula Ia, or Formula Ib can be amorphous or crystalline, or a mixture thereof. In some embodiments, the lyophilized composition comprises amorphous compound of Formula I, Formula Ia, or Formula Ib.

Reconstituted Lyophilized Formulations for Inhalation

In some embodiments, the present disclosure provides pharmaceutical compositions, wherein the pharmaceutical compositions are obtained by reconstitution of the lyophilized formulations as described above.

In some embodiments, the present disclosure provides pharmaceutical compositions for administration by inhalation, wherein the pharmaceutical compositions are obtained by reconstitution of the lyophilized formulations as described above.

The reconstituted compositions for administration by inhalation comprise the lyophilized composition described above, and water. In some embodiments, the present invention provides pharmaceutical compositions for administration by inhalation, comprising (i) the compound of Formula I, Formula Ia, or Formula I, or a pharmaceutically acceptable salt thereof, in an amount from 0.1% to 10% w/v relative to the volume of the pharmaceutical composition, (ii) cyclodextrin in an amount from 10% to 50% w/v relative to the volume of the pharmaceutical composition; and (iii) water. In some embodiments, the present invention provides pharmaceutical compositions for administration by inhalation, comprising (i) the compound of Formula Ia, or a pharmaceutically acceptable salt thereof, in an amount from 0.1% to 10% w/v relative to the volume of the pharmaceutical composition, (ii) cyclodextrin in an amount from 10% to 50% w/v relative to the volume of the pharmaceutical composition; and (iii) water.

The cyclodextrin of the reconstituted lyophilized compositions for inhalation can include any suitable cyclodextrin as described above. For example, the cyclodextrin can be a beta-cyclodextrin, such as sulfobutylalkylether-beta-cyclodextrin, betadex-sulfobutylether sodium, or hydroxypropyl-beta-cyclodextrin. In some embodiments, the reconstituted lyophilized compositions for inhalation include a beta-cyclodextrin. In some embodiments, the reconstituted lyophilized compositions for inhalation include sulfobutylalkylether-beta-cyclodextrin, betadex-sulfobutylether sodium, or hydroxypropyl-beta-cyclodextrin. In some embodiments, the reconstituted lyophilized compositions for inhalation include betadex-sulfobutylether sodium.

The water in the reconstituted lyophilized compositions for inhalation can be any suitable type of water. In some embodiments, the water in the reconstituted lyophilized compositions for inhalation is DI water, distilled water, or sterile water.

The reconstituted lyophilized compositions for inhalation comprise any suitable amount of the compound of Formula I, Formula Ia, or Formula Ib, for example from 0.1% to 10% w/v. In some embodiments, the compound of Formula I, Formula Ia, or Formula Ib is present in an amount of about 0.1% to 5% w/v, about 0.1 to 4 w/v, about 0.1 to 3 w/v, about 0.1 to 2 w/v, about 0.1 to 1 w/v, about 0.2 to 0.8 w/v, about 0.3 to 0.7 w/v, or about 0.4% to 0.6% w/v. In some embodiments, the amount of the compound of Formula I, Formula Ia, or Formula Ib in the reconstituted lyophilized compositions for inhalation is about 0.1% w/v, about 0.2 w/v, about 0.3 w/v, about 0.4 w/v, about 0.5 w/v, about 0.6 w/v, about 0.7 w/v, about 0.8 w/v, about 0.9 w/v, or about 1% w/v. In some embodiments, the amount of the compound of Formula I, Formula Ia, or Formula Ib in the reconstituted lyophilized compositions for inhalation is about 0.1% to 10% w/v. In some embodiments, the amount of the compound of Formula I, Formula Ia, or Formula Ib in the reconstituted lyophilized compositions for inhalation is about 0.1% to 1% w/v. In some embodiments, the amount of the compound of Formula I, Formula Ia, or Ib in the reconstituted lyophilized compositions for inhalation is about 0.5% w/v.

The reconstituted lyophilized compositions for inhalation comprise any suitable amount of the compound of Formula Ia, for example from 0.1% to 10% w/v. In some embodiments, the compound of Formula Ia, is present in an amount of about 0.1% to 5% w/v, about 0.1 to 4 w/v, about 0.1 to 3 w/v, about 0.1 to 2 w/v, about 0.1 to 1 w/v, about 0.2 to 0.8 w/v, about 0.3 to 0.7 w/v, or about 0.4% to 0.6% w/v. In some embodiments, the amount of the compound of Formula Ia in the reconstituted lyophilized compositions for inhalation is about 0.1% w/v, about 0.2 w/v, about 0.3 w/v, about 0.4 w/v, about 0.5 w/v, about 0.6 w/v, about 0.7 w/v, about 0.8 w/v, about 0.9 w/v, or about 1% w/v. In some embodiments, the amount of the compound of Formula Ia in the reconstituted lyophilized compositions for inhalation is about 0.1% to 10% w/v. In some embodiments, the amount of the compound of Formula Ia in the reconstituted lyophilized compositions for inhalation is about 0.1% to 1% w/v. In some embodiments, the amount of the compound of Formula Ia in the reconstituted lyophilized compositions for inhalation is about 0.5% w/v.

The reconstituted lyophilized compositions for inhalation include any suitable amount of the compound of Formula I, Formula Ia, or Formula Ib, for example about 0.1 to 100 mg/mL. In some embodiments, the compound of Formula I, Formula Ia, or Formula Ib can be present in the reconstituted lyophilized compositions for inhalation in an amount from 0.1 to 100 mg/mL, for example 0.1 to 50 mg/mL, 0.5 to 10 mg/mL, 1 to 10 mg/mL, 2 to 8 mg/mL, 3 to 7 mg/mL, 4 to 6 mg/mL, or 4.5 to 5.5 mg/mL. In some embodiments, the amount of the compound of Formula I, Formula Ia, or Formula Ib in the reconstituted lyophilized compositions for inhalation is about 0.1 mg/mL, about 0.5 mg/mL, about 1 mg/mL, about 2 mg/mL, about 2.5 mg/mL, about 3 mg/mL, about 3.5 mg/mL, about 4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 15 mg/mL, about 20 mg/mL or about 25 mg/mL. In some embodiments, the amount of compound of Formula I, Formula Ia, or Formula Ib in the reconstituted lyophilized compositions for inhalation is about 1 to 10 mg/mL. In some embodiments, the amount of the compound of Formula I, Formula Ia, or Formula Ib in the reconstituted lyophilized compositions for inhalation is about 4 to 6 mg/mL. In some embodiments, the amount of the compound of Formula I, Formula Ia, or Formula Ib in the reconstituted lyophilized compositions for inhalation is about 5 mg/mL.

The reconstituted lyophilized compositions for inhalation include any suitable amount of the compound of Formula Ia, for example about 0.1 to 100 mg/mL. In some embodiments, the compound of Formula Ia can be present in the reconstituted lyophilized compositions for inhalation in an amount from 0.1 to 100 mg/mL, for example 0.1 to 50 mg/mL, 0.5 to 10 mg/mL, 1 to 10 mg/mL, 2 to 8 mg/mL, 3 to 7 mg/mL, 4 to 6 mg/mL, or 4.5 to 5.5 mg/mL. In some embodiments, the amount of the compound of Formula Ia in the reconstituted lyophilized compositions for inhalation is about 0.1 mg/mL, about 0.5 mg/mL, about 1 mg/mL, about 2 mg/mL, about 2.5 mg/mL, about 3 mg/mL, about 3.5 mg/mL, about 4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 15 mg/mL, about 20 mg/mL or about 25 mg/mL. In some embodiments, the amount of the compound of Formula Ia in the reconstituted lyophilized compositions for inhalation is about 1 to 10 mg/mL. In some embodiments, the amount of the compound of Formula Ia in the reconstituted lyophilized compositions for inhalation is about 4 to 6 mg/mL. In some embodiments, the amount of the compound of Formula Ia in the reconstituted lyophilized compositions for inhalation is about 5 mg/mL.

The reconstituted lyophilized compositions for inhalation also comprises cyclodextrin in any suitable amount, for example about 5% to 50% w/v relative to the volume of the pharmaceutical formulation. In some embodiments, the cyclodextrin is present in an amount of about 5 to 25% w/v or about 10% to 20% w/v. In some embodiments, the cyclodextrin is present in an amount of about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 25% w/v, about 30% w/v, about 35% w/v, about 40% w/v, about 45% w/v, or about 50% w/v. In some embodiments, the cyclodextrin is present in the amount of about 5% to 50% w/v. In some embodiments, the cyclodextrin is present in the amount of about 10% to 20% w/v. In some embodiments, the cyclodextrin is present in the amount of about 15% w/v. In some embodiments, the betadex-sulfobutylether sodium is present in the amount of about 15% w/v.

In some embodiments, the reconstituted lyophilized compositions comprises cyclodextrin amount of about 5% to 10% w/v. In some embodiments, the cyclodextrin is present in the amount of about 6% to 8% w/v. In some embodiments, the cyclodextrin is present in the amount of about 7% to 8% w/v. In some embodiments, the betadex-sulfobutylether sodium is present in the amount of about 7.5% w/v.

In some embodiments, the reconstituted lyophilized compositions for inhalation comprise the compound of Formula I, Formula Ia, or Formula Ib, cyclodextrin, and water in any suitable combination of amounts as described above. For example, the reconstituted lyophilized compositions for inhalation comprise (i) the compound of Formula I, Formula Ia, or Formula Ib in an amount of about 0.1% to 5% w/v, about 0.1 to 4 w/v, about 0.1 to 3 w/v, about 0.1 to 2 w/v, about 0.1 to 1 w/v, about 0.2 to 0.8 w/v, about 0.3 to 0.7 w/v, or about 0.4% to 0.6% w/v relative to the volume of the pharmaceutical formulation, (ii) cyclodextrin in an amount of from about 5% to 50% w/v, about 5 to 25 w/v, about 10% to 20% w/v relative to the volume of the pharmaceutical formulation, and (iii) water. In some embodiments, the reconstituted lyophilized compositions for inhalation comprise (i) the compound of Formula I, Formula Ia, or Formula Ib in an amount of about 0.1% w/v, about 0.2, about 0.3, about 0.4, about 0.5, about 0.6, about 0.7, about 0.8, about 0.9, or about 1% w/v, (ii) cyclodextrin in an amount of about 6, about 7, about 8, about 9, about 10, about 11, about 12, about 13, about 14, about 15, about 16, about 17, about 18, about 19, about 20, about 25, about 30, about 35, about 40, about 45, or about 50% w/v, and (iii) water. In some embodiments, the reconstituted lyophilized compositions for inhalation comprises (i) the compound of Formula I, Formula Ia, or Formula Ib in an amount of 0.1% to 10% w/v, (ii) cyclodextrin in an amount of 5% to 50% w/v., and (iii) water. In some embodiments, the reconstituted lyophilized compositions for inhalation comprise (i) the compound of Formula I, Formula Ia, or Formula Ib in an amount of 0.1% to 1% w/v, (ii) cyclodextrin in an amount of 10% to 20% w/v, and (iii) water. In some embodiments, the reconstituted lyophilized compositions for inhalation comprise (i) the compound of Formula I, Formula Ia, or Formula Ib in an amount of about 0.5% w/v, (ii) cyclodextrin in an amount of about 15% w/v, and (iii) water. In some embodiments, the reconstituted lyophilized compositions for inhalation comprise (i) the compound of Formula I, Formula Ia, or Formula Ib in an amount of about 0.5% w/v, (ii) betadex-sulfobutylether sodium in an amount of about 15% w/v, and (iii) water.

In some embodiments, the reconstituted lyophilized compositions comprise (i) the compound of Formula I, Formula Ia, or Formula Ib, or a pharmaceutically acceptable salt thereof, in an amount of 0.1% to 1% w/v, (ii) cyclodextrin in an amount of 5% to 10% w/v, and (iii) water. In some embodiments, the reconstituted lyophilized compositions comprise (i) the compound of Formula I, Formula Ia, or Formula Ib, or a pharmaceutically acceptable salt thereof, in an amount of about 0.5% w/v, (ii) cyclodextrin in an amount of about 6%-8% w/v, and (iii) water. In some embodiments, the reconstituted lyophilized compositions for inhalation comprise (i) the compound of Formula I, Formula Ia, or Formula Ib, or a pharmaceutically acceptable salt thereof, in an amount of about 0.5% w/v, (ii) betadex-sulfobutylether sodium in an amount of about 7%-8% w/v, and (iii) water. In some embodiments, the reconstituted lyophilized compositions for inhalation comprise (i) the compound of Formula I, Formula Ia, or Formula Ib, or a pharmaceutically acceptable salt thereof, in an amount of about 0.5% w/v, (ii) betadex-sulfobutylether sodium in an amount of about 7.5% w/v, and (iii) water.

In some embodiments, the reconstituted lyophilized compositions for inhalation comprise (i) the compound of Formula Ia, or a pharmaceutically acceptable salt thereof, in an amount of about 0.5% w/v, (ii) betadex-sulfobutylether sodium in an amount of about 7.5% w/v, and (iii) water. In some embodiments, the reconstituted lyophilized compositions for inhalation comprise (i) the compound of Formula Ia in an amount of about 0.5% w/v, (ii) betadex-sulfobutylether sodium in an amount of about 7.5% w/v, and (iii) water.

In some embodiments, the reconstituted lyophilized compositions for inhalation comprise the compound of Formula Ia, cyclodextrin, and water in any suitable combination of amounts as described above. For example, the reconstituted lyophilized compositions for inhalation comprise (i) the compound of Formula Ia, or Formula Ib in an amount of about 0.1% to 5% w/v, about 0.1 to 4 w/v, about 0.1 to 3 w/v, about 0.1 to 2 w/v, about 0.1 to 1 w/v, about 0.2 to 0.8 w/v, about 0.3 to 0.7 w/v, or about 0.4% to 0.6% w/v, (ii) cyclodextrin in an amount of from about 5% to 50% w/v, or about 5 to 25 w/v, or about 10% to 20% w/v, and (iii) water. In some embodiments, the reconstituted lyophilized compositions for inhalation comprise (i) the compound of Formula I, Formula Ia, or Formula Ib in an amount of about 0.1% w/v, or about 0.2, about 0.3, about 0.4, about 0.5, about 0.6, about 0.7, about 0.8, about 0.9, or about 1% w/v, (ii) cyclodextrin in an amount of about 6, about 7, about 8, about 9, about 10, about 11, about 12, about 13, about 14, about 15, about 16, about 17, about 18, about 19, about 20, about 25, about 30, about 35, about 40, about 45, or about 50% w/v, and (iii) water. In some embodiments, the reconstituted lyophilized compositions for inhalation comprises (i) the compound of Formula I, Formula Ia, or Formula Ib in an amount of 0.1% to 10% w/v, (ii) cyclodextrin in an amount of 5% to 50% w/v., and (iii) water. In some embodiments, the reconstituted lyophilized compositions for inhalation comprise (i) the compound of Formula I, Formula Ia, or Formula Ib in an amount of 0.1% to 1% w/v, (ii) cyclodextrin in an amount of 10% to 20% w/v, and (iii) water. In some embodiments, the reconstituted lyophilized compositions for inhalation comprise (i) the compound of Formula I in an amount of about 0.5% w/v, (ii) cyclodextrin in an amount of about 15% w/v, and (iii) water. In some embodiments, the reconstituted lyophilized compositions for inhalation comprise (i) the compound of Formula I, Formula Ia, or Formula Ib in an amount of about 0.5% w/v, (ii) betadex-sulfobutylether sodium in an amount of about 15% w/v, and (iii) water.

In some embodiments, the reconstituted lyophilized compositions for inhalation comprises the compound of Formula I, Formula Ia, or Formula Ib in an amount of 0.1% to 10% w/v relative to the volume of the pharmaceutical formulation, cyclodextrin in an amount from 10% to 20% w/v relative to the volume of the pharmaceutical formulation, and water. In some embodiments, the reconstituted lyophilized compositions for inhalation comprises the compound of Formula I, Formula Ia, or Formula Ib in an amount of about 0.5% w/v relative to the volume of the pharmaceutical formulation, cyclodextrin in an amount of about 15% w/v relative to the volume of the pharmaceutical formulation, and water. In some embodiments, the reconstituted lyophilized compositions for inhalation consists essentially of the compound of Formula I, Formula Ia, or Formula Ib in an amount of about 0.5% w/v relative to the volume of the pharmaceutical formulation, cyclodextrin in an amount of about 15% w/v relative to the volume of the pharmaceutical formulation, and water.

In some embodiments, the reconstituted lyophilized compositions for inhalation comprises the compound of Formula Ia in an amount of 0.1% to 10% w/v relative to the volume of the pharmaceutical formulation, cyclodextrin in an amount from 10% to 20% w/v, relative to the volume of the pharmaceutical formulation and water. In some embodiments, the reconstituted lyophilized compositions for inhalation comprises the compound of Formula Ia in an amount of about 0.5% w/v relative to the volume of the pharmaceutical formulation, cyclodextrin in an amount of about 15% w/v relative to the volume of the pharmaceutical formulation, and water. In some embodiments, the reconstituted lyophilized compositions for inhalation consist essentially of the compound of Formula Ia in an amount of about 0.5% w/v relative to the volume of the pharmaceutical formulation, cyclodextrin in an amount of about 15% w/v relative to the volume of the pharmaceutical formulation, and water.

In some embodiments, the reconstituted lyophilized compositions for inhalation include the compound of Formula I, Formula Ia, or Formula Ib in an amount of 0.1% to 10% w/v relative to the volume of the pharmaceutical formulation, betadex-sulfobutylether sodium in an amount from 10% to 20% w/v relative to the volume of the pharmaceutical formulation, and water. In some embodiments, the reconstituted lyophilized compositions for inhalation comprises the compound of Formula I, Formula Ia, or Formula Ib in an amount of about 0.5% w/v relative to the volume of the pharmaceutical formulation, betadex-sulfobutylether sodium in an amount of about 15% w/v relative to the volume of the pharmaceutical formulation, and water. In some embodiments, the reconstituted lyophilized compositions for inhalation consist essentially of the compound of Formula I, Formula Ia, or Formula Ib in an amount of about 0.5% w/v relative to the volume of the pharmaceutical formulation, betadex-sulfobutylether sodium in an amount of about 15% w/v relative to the volume of the pharmaceutical formulation, and water.

In some embodiments, the reconstituted lyophilized compositions for inhalation include the compound of Formula Ia in an amount of 0.1% to 10% w/v relative to the volume of the pharmaceutical formulation, betadex-sulfobutylether sodium in an amount from 10% to 20% w/v relative to the volume of the pharmaceutical formulation, and water. In some embodiments, the reconstituted lyophilized compositions for inhalation comprises the compound of Formula Ia in an amount of about 0.5% w/v relative to the volume of the pharmaceutical formulation, betadex-sulfobutylether sodium in an amount of about 15% w/v relative to the volume of the pharmaceutical formulation, and water. In some embodiments, the reconstituted lyophilized compositions for inhalation consist essentially of the compound of Formula Ia in an amount of about 0.5% w/v relative to the volume of the pharmaceutical formulation, betadex-sulfobutylether sodium in an amount of about 15% w/v relative to the volume of the pharmaceutical formulation, and water.

The reconstituted lyophilized compositions for inhalation can be contained in any suitable container, such as a sealed vial or a nebulizer. In some embodiments, the present invention provides a sealed vial containing the reconstituted lyophilized compositions for inhalation. In some embodiments, the present invention provides a nebulizer containing the reconstituted lyophilized compositions for inhalation. In some embodiments, the present invention provides a nebulizer containing the injectable composition consisting essentially of the compound of Formula I, Formula Ia, or Formula Ib in an amount of about 0.5% w/v relative to the volume of the pharmaceutical formulation, cyclodextrin in an amount of about 15% w/v relative to the volume of the pharmaceutical formulation, and water.

8. Anti-Microbial Agents or Preservative

The pharmaceutical formulations disclosed herein may additionally comprise anti-microbial agents or preservatives, which may help improve the stability of the pharmaceutical formulations. Examples of the anti-microbial agents or preservatives include, but are not limited to, aminobenzoate esters (e.g., parabens), quaternary ammonium compounds (e.g., benzalkonium chloride (BKC), benzethonium chloride, cetrimide), aryl acids (e.g., benzoic acid), aryl alcohols (e.g., benzyl alcohols), biguanides (e.g., chlorhexidine), chlorocresol, chloroxylenol, formaldehyde donator (e.g., imidurea, bronopol), alkyl acid (e.g., propionic acid and sorbic acid), phenolic compounds (e.g., m-cresol), phenylmercuric salts (e.g., acetate, borate, and nitrate), and phenoxy ethanol, thiomersal.

In some embodiments, the antimicrobial agent or the preservative is methylparaben, propylparaben, chlorobutanol, benzalkonium chloride, cetylpyridinium chloride, thymol, ascorbic acid, sodium bisulfite, sodium metabisulfite, sodium bisulfite, sodium sulfate, sodium bisulfate EDTA, or a combination thereof. In some embodiments, the antimicrobial agent or the preservative is methylparaben, propylparaben, chlorobutanol, benzalkonium chloride, sodium sulfate, or a combination thereof.

9. Taste Masking/Flavoring Agents

The pharmaceutical formulations disclosed herein may further comprise a taste masking agent or a flavoring agent. A wide array of pharmaceutically compatible flavoring agents may be utilized. Such flavoring agents include natural and artificial flavors chosen from synthetic flavor oils and flavoring aromatics, and/or oils, oleo resins and extracts derived from plants, leaves, flowers, fruits and so forth, and combinations thereof. Examples of flavoring agents that could be used include, but are not limited to, citric acid, sodium citrate, ascorbic acid, menthol, or saccharin sodium.

IV. Kits

The present disclosure also provides the use of a kit comprising a pharmaceutical formulation disclosed herein. In some embodiments, the kit further comprises a label and/or instructions for using the pharmaceutical formulation.

In some embodiments, the kit provided herein comprise a pharmaceutical formulation disclosed herein and a syringe. In some embodiments, the kit further comprises a label and/or instructions for using the pharmaceutical formulation.

In some embodiments, the kit provided herein comprise (i) a lyophilized pharmaceutical formulation disclosed herein, (ii) water (e.g., water for injection) for reconstitution of the lyophilized pharmaceutical formulation and (iii) a syringe. In some embodiments, the kit provided herein comprise (i) a first vial comprising a lyophilized pharmaceutical formulation disclosed herein, (ii) a second vial comprising water (e.g., water for injection) for reconstitution of the lyophilized pharmaceutical formulation and (iii) a syringe. In some embodiments, the kit further comprises vial adapters for the first and the second vial. In some embodiments, the kit further comprises a label and/or instructions for using the pharmaceutical formulation.

In some embodiments, the kit provided herein comprise (i) a first vial comprising a lyophilized pharmaceutical formulation comprising 35-45 mg of the compound of Formula Ia, (ii) a second vial comprising 5 mL-15 mL water (e.g., water for injection) for reconstitution of the lyophilized pharmaceutical formulation and (iii) a syringe. In some embodiments, the kit further comprises vial adapters for the first and the second vial. In some embodiments, the kit further comprises a label and/or instructions for using the pharmaceutical formulation.

In some embodiments, the kit provided herein comprise (i) a first vial comprising a lyophilized pharmaceutical formulation comprising 40 mg of the compound of Formula Ia, (ii) a second vial comprising 10 mL water (e.g., water for injection) for reconstitution of the lyophilized pharmaceutical formulation and (iii) a syringe. In some embodiments, the kit further comprises vial adapters for the first and the second vial. In some embodiments, the kit further comprises a label and/or instructions for using the pharmaceutical formulation.

In some embodiments, the kit provided herein comprise (i) a lyophilized pharmaceutical formulation disclosed herein and (ii) a syringe comprising water (e.g., water for injection) for reconstitution of the lyophilized pharmaceutical formulation. In some embodiments, the kit provided herein comprise (i) a vial comprising a lyophilized pharmaceutical formulation disclosed herein and (ii) a syringe comprising water (e.g., water for injection) for reconstitution of the lyophilized pharmaceutical formulation. In some embodiments, the kit further comprises a vial adapter. In some embodiments, the kit further comprises a label and/or instructions for using the pharmaceutical formulation.

In some embodiments, the kit comprises multiple sets, where each set comprises: (i) a lyophilized pharmaceutical formulation disclosed herein and (ii) a syringe comprising water (e.g., water for injection) for reconstitution of the lyophilized pharmaceutical formulation. In some embodiments, the number of sets in the kit is equal to the number of treatment days (i.e., one set to be used on each treatment day). In some embodiments, the kit further comprises a label and/or instructions for using the pharmaceutical formulation.

In some embodiments, the kit comprises multiple sets, wherein each set comprises (i) a vial comprising a lyophilized pharmaceutical formulation disclosed herein and (ii) a syringe comprising water (e.g., water for injection) for reconstitution of the lyophilized pharmaceutical formulation. In some embodiments, each set further comprises a vial adapter. In some embodiments, the number of sets in the kit is equal to the number of treatment days (i.e., one set to be used on each treatment day). In some embodiments, the kit further comprises a label and/or instructions for using the pharmaceutical formulation.

In some embodiments, the kit comprises five sets, wherein each set comprises (i) a vial comprising a lyophilized pharmaceutical formulation disclosed herein and (ii) a syringe comprising water (e.g., water for injection) for reconstitution of the lyophilized pharmaceutical formulation. In some embodiments, each set further comprises a vial adapter. In some embodiments, the five sets are for five treatment days (one for each day). In some embodiments, the kit further comprises a label and/or instructions for using the pharmaceutical formulation.

In some embodiments, the kit comprises five sets, where each set comprises (i) a vial comprising a lyophilized pharmaceutical formulation comprising 30 mg-40 mg of the compound of Formula Ia and (ii) a syringe comprising 5 mL-10 mL water for injection for reconstitution of the lyophilized pharmaceutical formulation. In some embodiments, each set further comprises a vial adapter. In some embodiments, the five sets are for five treatment days (one for each day). In some embodiments, the kit further comprises a label and/or instructions for using the pharmaceutical formulation.

In some embodiments, the kit comprises five sets, where each set comprises (i) a vial comprising a lyophilized pharmaceutical formulation comprising 38 mg of the compound of Formula Ia and (ii) a syringe comprising 7.8 mL water for injection for reconstitution of the lyophilized pharmaceutical formulation. In some embodiments, each set further comprises a vial adapter. In some embodiments, the five sets are for five treatment days (one for each day). In some embodiments, the kit further comprises a label and/or instructions for using the pharmaceutical formulation.

In some embodiments, the kit further comprises an nebulizer. Any suitable nebulizer may be used. In some embodiments, the nebulizer is a glass nebulizer. In some embodiments, the nebulizer is a hand bulb nebulizer. In some embodiments, the nebulizer is a jet nebulizer or a vibrating mesh nebulizer. In some embodiments, the nebulizer is a jet nebulizer (e.g., VixOne™ AeroEclipse®, Pari LC® Plus). In some examples the nebulizer is a vibrating mesh nebulizer (e.g., eFlow® rapid) In some embodiments, the nebulizer is an ultrasonic nebulizer. In some embodiments, the nebulizer is an adaptive aerosol delivery nebulizer. In some embodiments, the nebulizer is a metered dose inhaler (e.g., a metered dose liquid inhaler).

V. Methods of Use

The present disclosure also provides a method of treating or preventing a viral infection in a subject (e.g., human) in need thereof, the method comprising administering to the subject a pharmaceutical formulation described herein, wherein the administration is by inhalation.

In some embodiments, the present disclosure provides a method of treating a viral infection in a subject (e.g., human) in need thereof, the method comprising administering to a subject in need thereof a pharmaceutical formulation described herein, wherein the administration is by inhalation.

In some embodiments, the present disclosure provides for methods of treating or preventing a viral infection in a subject (e.g., human) in need thereof, the method comprising administering to the subject a pharmaceutical formulation disclosed herein by inhalation, and at least one additional active therapeutic agent.

In some embodiments, the present disclosure provides for methods of treating a viral infection in a subject (e.g., human) in need thereof, the method comprising administering to the subject a pharmaceutical formulation disclosed herein by inhalation, and at least one additional active therapeutic agent.

In one embodiment, the present disclosure provides for methods of inhibiting a viral polymerase in a cell, the methods comprising contacting the cell infected a virus with a pharmaceutical formulation disclosed herein, whereby the viral polymerase is inhibited.

In one embodiment, the present disclosure provides for methods of inhibiting a viral polymerase in a cell, the methods comprising contacting the cell infected a virus with a pharmaceutical formulation disclosed herein, and at least one additional active therapeutic agent, whereby the viral polymerase is inhibited.

Also provided here are the uses of the pharmaceutical formulations disclosed herein for use in treating or preventing a viral infection in a subject in need thereof. For example, provided herein are uses of the pharmaceutical formulations disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a human in need thereof, the method comprising administering to the human a pharmaceutical formulation disclosed herein, wherein the administration is by inhalation. Paramyxoviridae viruses include, but are not limited to Nipah virus, Hendra virus, measles, mumps, and parainfluenza virus.

In some embodiments, the viral infection is a pneumoviridae virus infection. As such, in some embodiments, the present disclosure provides a method of treating a pneumoviridae virus infection in a human in need thereof, the method comprising administering to the human a pharmaceutical formulation provided herein, wherein the administration is by inhalation. Pneumoviridae viruses include, but are not limited to, respiratory syncytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a pharmaceutical formulation disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a pharmaceutical formulation provided herein, wherein the administration is by inhalation. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a pharmaceutical formulation disclosed herein, wherein the administration is by inhalation.

In some embodiments, the present disclosure provides a method for reducing the viral load associated with RSV infection, wherein the method comprises administering to a human infected with RSV a pharmaceutical formulation disclosed herein, wherein the administration is by inhalation.

In some embodiments, the viral infection is a picornaviridae virus infection. As such, in some embodiments, the present disclosure provides a method of treating a picornaviridae virus infection in a human in need thereof, the method comprising administering to the human a pharmaceutical formulation of the present disclosure, wherein the administration is by inhalation. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a pharmaceutical formulation, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a pharmaceutical composition described herein, wherein the administration is by inhalation. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese encephalitis virus infection. In some embodiments, the flaviviridae virus infection is a hepatitis C virus infection.

In some embodiments, the present disclosure provides use of a pharmaceutical formulation disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human pharmaceutical formulation disclosed herein, wherein the administration is by inhalation. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a pharmaceutical formulation for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a pharmaceutical formulation provided herein, wherein the administration is by inhalation. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. The pharmaceutical formulations provided herein are useful for treatment of all SARS-CoV-2 infections (COVID-19), for example for the treatment of mild, moderate, or severe SARS-CoV-2 infection. In some embodiments, the pharmaceutical formulations for inhalation provided herein are used for treatment of severe SARS-CoV-2 infection. In some embodiments, the pharmaceutical formulations for inhalation provided herein are used for treatment of moderate SARS-CoV-2 infection. In some embodiments, the pharmaceutical formulations for inhalation provided herein are used for treatment of mild SARS-CoV-2 infection. In some embodiments, the pharmaceutical formulations for inhalation provided herein are used for treatment of early stage SARS-CoV-2 infection when the virus is primarily replicated in the upper respiratory tract of the subject.

In some embodiments, the pharmaceutical formulations for inhalation provided herein are used for treatment of a zoonotic coronavirus infection. In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant), P.1 variant (the Brazil variant), B.1.1.7 with E484K variant, B.1.1.207 variant, B.1.1.317 variant, B.1.1.318 variant, B.1.429 variant, B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a pharmaceutical formulation for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection.

In some embodiments, the viral infection is an arenaviridae virus infection. As such, in some embodiments, the disclosure provides a method of treating an arenaviridae virus infection in a human in need thereof, the method comprising administering to the human a pharmaceutical formulation disclosed herein, wherein the administration is by inhalation. In some embodiments, the arenaviridae virus infection is a Lassa infection or a Junin infection.

In some embodiments, the present disclosure provides a pharmaceutical formulation for use in the treatment of a arenaviridae virus infection in a human in need thereof. In some embodiments, the arenaviridae virus infection is a Lassa infection or a Junin infection.

In some embodiments, the viral infection is an orthomyxovirus infection, for example an influenza virus infection. In some embodiments, the viral infection is an influenza virus A, influenza virus B, or influenza virus C infection.

In some embodiments, the human receives at least one additional dose of the compound of Formula I, Formula Ia, or Formula Ib by intravenous administration. In some embodiments, the human receives at least one additional dose of the compound of Formula Ia by intravenous administration.

In some embodiments, the methods of treating or preventing the viral infection provided herein further comprise administering to the human at least one dose of the compound of Formula I, Formula Ia or Formula Ib via intravenous administration. In some embodiments, the methods of treating or preventing the viral infection provided herein further comprise administering to the human at least one dose of the compound of Formula Ia via intravenous administration. The at least one additional dose may be provided before, during or after the inhalation administration of the pharmaceutical formulations disclosed herein.

The pharmaceutical formulations for inhalation provided herein are also useful for treatment and or prevention of viral infections in humans with compromised renal function. In some examples, the pharmaceutical formulations provided herein are used for treatment and or prevention of a viral infection in humans with an estimated glomerular filtration rate (eGFR) eFGR of less than 90, for examples an eFGR of 60-89, 45-59, 30-44, 15-29, or less than 15. In some examples, the pharmaceutical formulations provided herein are used for treatment and or prevention of a viral infection in humans with an eFGR of less than 30, for example an eFGR of 15-29. In some examples, the pharmaceutical formulations provided herein are used for treatment and or prevention of a viral infection in humans with an eFGR of less than 15.

As described more fully herein, the pharmaceutical formulation described herein can be administered with one or more additional therapeutic agent(s) to an individual (e.g., a human) infected with a viral infection. The additional therapeutic agent(s) can be administered to the infected individual at the same time as the pharmaceutical formulation of the present disclosure or before or after administration of the pharmaceutical formulation of the present disclosure.

VI. Combination Therapy

The compounds described herein can also be used in combination with one or more additional therapeutic agents. As such, also provided herein are methods of treatment of the a viral infection in a subject in need thereof, wherein the methods comprise administering to the subject a pharmaceutical formulation disclosed therein and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine, or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agents is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682 (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some examples, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYIVITUZA® (darunavir, tenofovir alafenamide hemifumarate, emtricitabine, and cobicistat); SYIVIFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUIMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some examples, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some examples, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase- LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some examples, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUIMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir;

lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vaqta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is a PD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASCO9F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5] decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of 2019-nCoV virus antibody.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immonumodulatory medications (e.g., interferon), other small molecule or biologics antiviral agents targeting 2019-nCoV (such as but not limited to lopinavir/ritonavir, EIDD-1931, favipiravir, ribavirine, neutralizing antibodies, etc), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine. In some embodiments, the additional therapeutic agent is EIDD-2801 (MH-4482, Molnupiravir).

In some examples, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimunab, ifliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and *Mycoplasma pneumoniae*), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some examples, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some examples, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some examples, the additional therapeutic agent is carrimycin, suramin, triazavirin, dipyridamole, bevacizumab, meplazumab, GD31 (*rhizobium*), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially. In general, during alternation therapy, an effective dosage of each active ingredient is administered sequentially, i.e., serially, whereas in combination therapy, effective dosages of two or more active ingredients are administered together. A synergistic antiviral effect denotes an antiviral effect which is greater than the predicted purely additive effects of the individual compounds of the combination.

1. Combination Therapy for the Treatment of Pneumoviridae

The pharmaceutical formulations provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The pharmaceutical formulations provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the pharmaceutical formulations provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan–1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The pharmaceutical formulations provided herein may also be combined with mucolytic agents to treat both the infection and symptoms of respiratory infections. A non-limiting example of a mucolytic agent is ambroxol. Similarly, the pharmaceutical formulations may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J. Pediatrics 2007, 266). Thus, the compounds provided herein may also be combined with nebulized hypertonic saline particularly when the virus infection is complicated with bronchiolitis. The combination of the pharmaceutical formulation provided herein with hypertonic saline may also comprise any of the additional agents discussed above. In one embodiment, nebulized about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The pharmaceutical formulations provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick Cl protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The pharmaceutical formulations provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The pharmaceutical formulations provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

VII. Methods of Making the Pharmaceutical Formulations

Also provided herein are methods of making the pharmaceutical formulations described herein. The method of making the pharmaceutical formulations described herein generally comprise combining the compound of Formula I, Formula Ia, or Formula Ib with the aqueous vehicle. In some embodiments, the method further comprises preparing the aqueous formulation by mixing the appropriate amounts of the desired excipients in water, for example in DI Water, distilled water or sterile water. The excipients comprise one or more agents selected from co-solvent, surfactant, cyclodextrin, suspending agent, buffering/pH adjusting agents, tonicity adjusting agents, anti-microbial/preservative agents, and/or taste masking/flavoring agents as detailed herein. The excipients can be mixed in any suitable order. In some embodiments, the excipients are mixed simultaneously. In some embodiments, the excipients are mixed sequentially.

In some embodiments, the methods of making the pharmaceutical formulations disclosed herein further comprise milling to micronize the compound of Formula I, Formula Ia, or Formula Ib. Milling can be before (dry milling) or after (wet milling) adding the compound of Formula I, Formula Ia, or Formula Ib in the aqueous vehicle.

In some embodiments, the methods of making the pharmaceutical formulations disclosed herein comprise (i) preparing a pre-mill formulation by mixing compound of Formula I, Formula Ia, or Formula Ib and the aqueous vehicle and (ii) milling the pre-milled formulation to reduce the particle size of the compound of Formula I, Formula Ia, or Formula Ib to form a post-milled suspension. In some embodiments, the methods further comprise diluting the post-milled suspension to achieve a target concentration of the pharmaceutical formulation.

VIII. Examples

Example 1: General Procedure for Preparation of Solution Formulations

A bulk solution of the intended formulation vehicle is prepared prior to combining the vehicle with the compound of Formula I, Formula Ia, or Formula Ib. The vehicle is prepared by dissolving the appropriate excipients (e.g., co-solvent, surfactant, solubility enhancing polymer such as cyclodextrin, buffering/pH adjusting agents, tonicity adjusting agents, anti-microbial/preservative agents, and/or taste masking/flavoring agents) in DI water to form a solution. Then, the compound of Formula I, Formula Ia, or Formula Ib in appropriate form (e.g., free form, salt, co-crystal, or a solution of the compound of Formula I, Formula Ia, or Formula Ib in a co-solvent) is dissolved in the vehicle to form a solution at the target concentration of the final formulation.

Example 2: General Procedure for Preparation of the Suspension Formulations A bulk solution of the intended formulation vehicle is prepared prior to combining the compound of Formula I, Formula Ia, or Formula Ib with the vehicle. In general, the vehicle is prepared by dissolving the appropriate excipients (e.g., co-solvent, surfactant, cyclodextrin, suspending agent, buffering/pH adjusting agents, tonicity adjusting agents, anti-microbial/preservative agents, and/or taste masking/flavoring agents) in DI water to form a solution of the excipients at the desired concentrations. Then, a pre-milled formulation intermediate of concentrated compound of Formula I, Formula Ia, or Formula Ib is made by mixing solid compound of Formula I, Formula Ia, or Formula Ib and vehicle to form a crude slurry. The slurry is wet milled to reduce the particle size of the compound of Formula I, Formula Ia, or Formula Ib to the target size and form the suspension. The concentration of the compound of Formula I, Formula Ia, or Formula Ib in the suspension is measured, and the suspension is diluted with vehicle to achieve the target concentration of the final formulation.

Example 3: Preparation of Exemplary Aqueous Vehicles of the Disclosure 0.1% w/v HPMC, 0.5% w/v poloxamer 237, and 0.9% w/v sodium chloride in water: A stir bar and 330 mL of DI water and were added to a 1000 mL media bottle and heated to ~90° C. The water was then stirred until a vortex formed, and 1.00 gram of HPMC was added to the vortex. The mixture was stirred for 15 min. The mixture was then removed from the heat and 670 mL of cold DI water was added to the bottle. Then 8.75 g of sodium chloride and 5.00 g of poloxamer 237 were added. Stirring was continued as the solution was allowed to cool to ambient temperature.

0.1% HPMC in PBS: A stir bar and 330 mL of DI water were added to a 1000 mL media bottle and heated to ~90° C. The water was then stirred until a vortex formed, and 1.00 gram of HPMC was slowly added to the vortex. The mixture was stirred 15 min. The mixture was then removed from the heat and add 670 mL of cold DI water was added to the bottle. Then 8.75 g of sodium chloride, 0.850 g of sodium phosphate monobasic monohydrate, and 5.05 g of sodium phosphate dibasic heptahydrate were added and stirring was continued as the solution was allowed to cool to ambient temperature.

0.5% w/v poloxamer 237 and 0.9% w/v sodium chloride in water. A stir bar, 5.00 g of poloxamer 237, 8.75 g of NaCl, and 1000 mL of DI water and were added to a 1000 mL media bottle. The mixture was stirred until a solution was formed.

Example 4: Preparation of Exemplary Pharmaceutical Formulations of the Disclosure The compound of Formula Ia at 15 mg/mL in water with 0.1% w/v HPMC, 0.5% w/v poloxamer 237, and 0.9% sodium chloride: The aqueous vehicle containing the excipients HPMC, poloxamer 237, and sodium chloride was prepared as described above in Example 3. Then 4.00 mL of the vehicle, 98.83 mg of the compound of Formula Ia, and 12 g of 0.5 mm zirconium oxide milling beads were added to a size 7 mL soft tissue homogenizing vial. The vial capped, vortexed briefly, and then placed in a Bertin Instruments Precellys® Evolution blender. The blender was used to wet mill the mixture for 15×30 second cycles, with 120 second rest time between cycles. The blender speed was 7,200 rpm and cooling set was set to high. After milling, the milled suspension was separated from the beads by withdrawing the suspension from the vial using a syringe with a 1.5" 25G needle. The recovered volume of the concentrated suspension was noted as 2.97 mL, and the concentration was measured as 25.8 mg/mL. The suspension was diluted with 2.14 mL of vehicle to obtain the target concentration of 15 mg/mL. The final formulation had a measured osmolarity of 285 mOsm/kg, pH of 6.89, and volume mean diameter particle size of 3.65 μm.

The compound of Formula Ia at 100 mg/mL in water with 0.1% w/v HPMC, 0.5% w/v poloxamer 237, and 0.9% sodium chloride: The suspension vehicle containing the excipients HPMC, poloxamer 237, and sodium chloride was prepared as described above in Example 3. Then the pre-mill formulation intermediate was made by mixing 150 mL of the vehicle with 25.0 g of solid compound of Formula Ia. The particle size of the compound of Formula Ia in the pre-mill formulation intermediate was reduced by wet milling using a Netzsch DeltaVite® 15-300 mill. The mill was configured with a 200 mL reservoir, 50z continuous milling chamber containing 150 g of 0.5 μm zirconium oxide beads, 300 μm screen, and Ultracool™ UC4 process circulation chiller. The chiller set to 30° F., pump set to 100 rpm, and agitator set to 3000 rpm. The pump was primed with 100 mL of vehicle, and the first 80 mL of flowthough from priming was sent to waste. The mill was then set to recirculate as feeding continued with the addition of 150 mL of pre-mill formulation intermediate, followed by 25 mL of vehicle rinse. The formulation was allowed to recirculate though the mill for 1 hr, after which the flow was directed to a collection bottle. After 100 mL of concentrated suspension formulation was collected in the bottle, a vehicle chase was fed into the mill. Collection was stopped when the recovered volume reached 250 mL. The particle size of the compound of Formula Ia in the final formulation was <5 μm by polarized light microscopy, with a measured concentration of 99.9 mg/mL.

Example 5: Suspension Stability of the Pharmaceutical Formulations of the Compound of Formula Ia The following formulations of the compound of Formula Ia were prepared according to the methods described above.

| Vial No. | Formulation vehicle |
|---|---|
| 1 | PBS/0.1% HPMC |
| 2 | 150 mM NaCl/0.5% Poloxamer 237 |
| 3 | 150 mM NaCl/0.1% HPMC/0.5% Poloxamer 237 |
| 4 | 75 mM NaCl/0.1% HPMC/0.5% Poloxamer 237 |
| 5 | 0.1% HPMC/0.5% Poloxamer 237 |
| 6 | 0.5% Poloxamer 237 |
| 7 | 75 mM NaCl/0.1% HPMC/0.02% Tween 80 |
| 8 | 0.1% HPMC/0.02% Tween 80 |

Each formulation was evaluated for sedimentation by visual inspection. The results of these experiments are shown in FIG. 1. As seen in FIG. 1, four hours after standing, the formulations in vials 3, 4, and 5 showed decreased sedimentation as compared to the other formulations evaluated.

Example 6: Impact of Particle Size

Following formulations of the compound of Formula Ia were prepared and evaluated by visual inspection and microscopic analysis.

Figure 3:
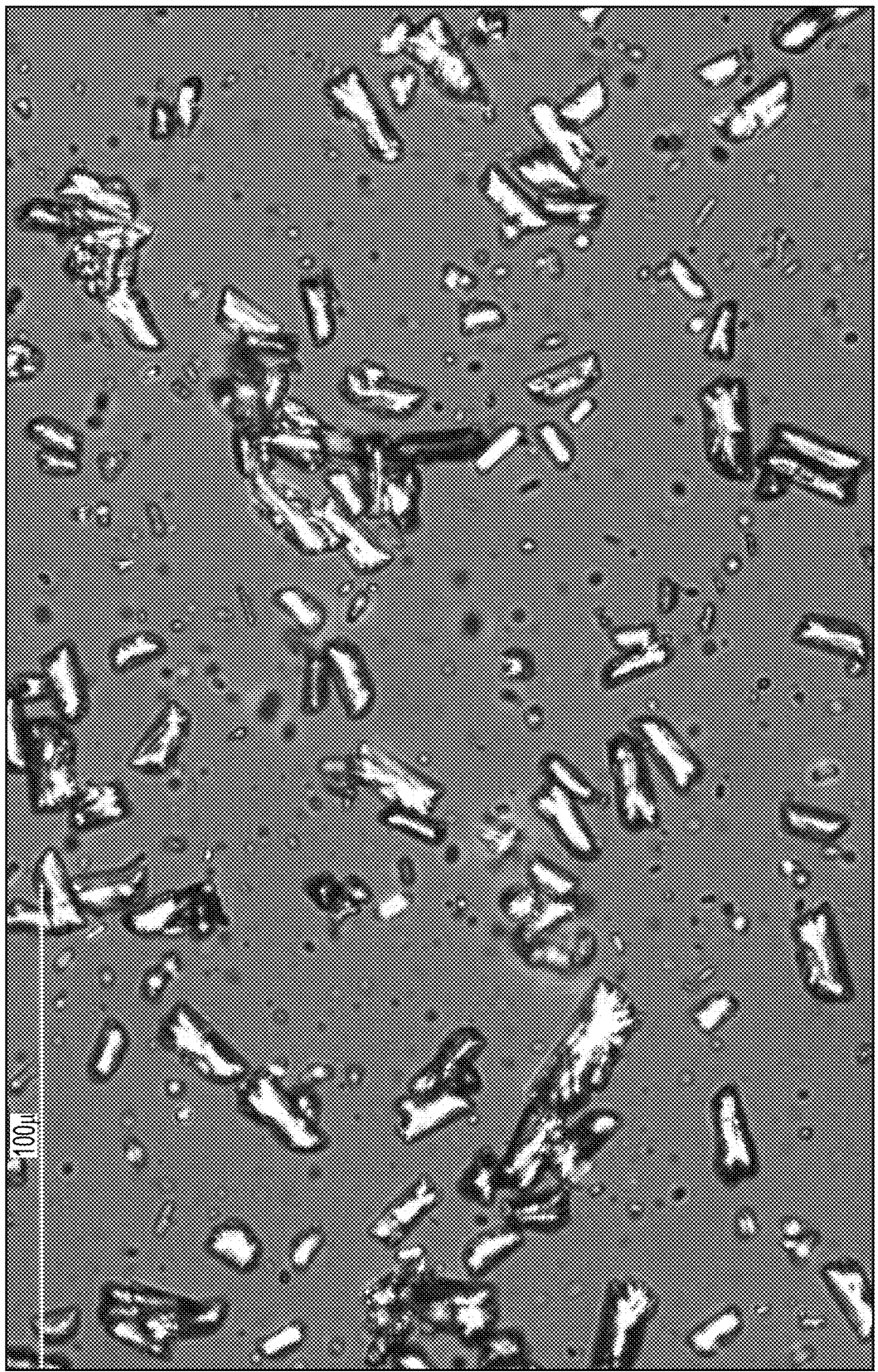
FIG. 3. Shows microscopic images of a pre-milled exemplary pharmace
Figure 4:
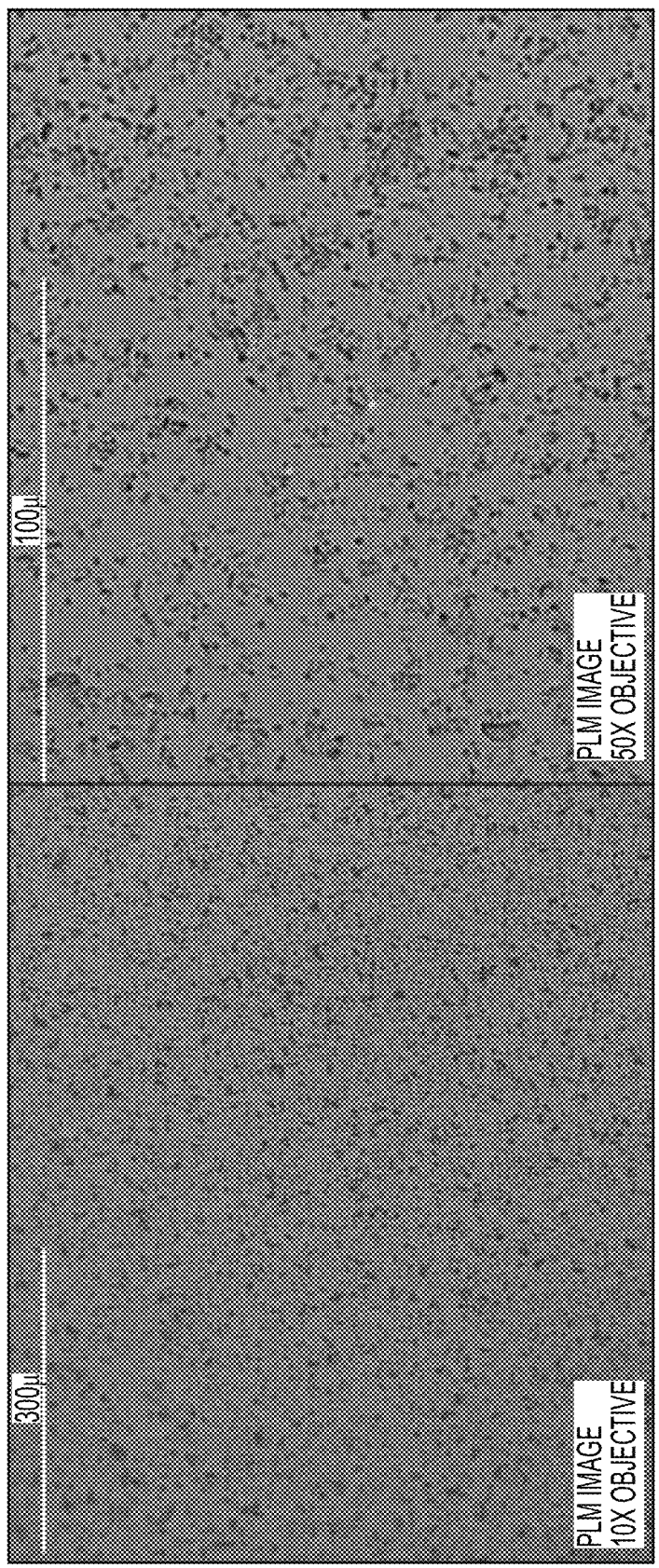
Figure 5:
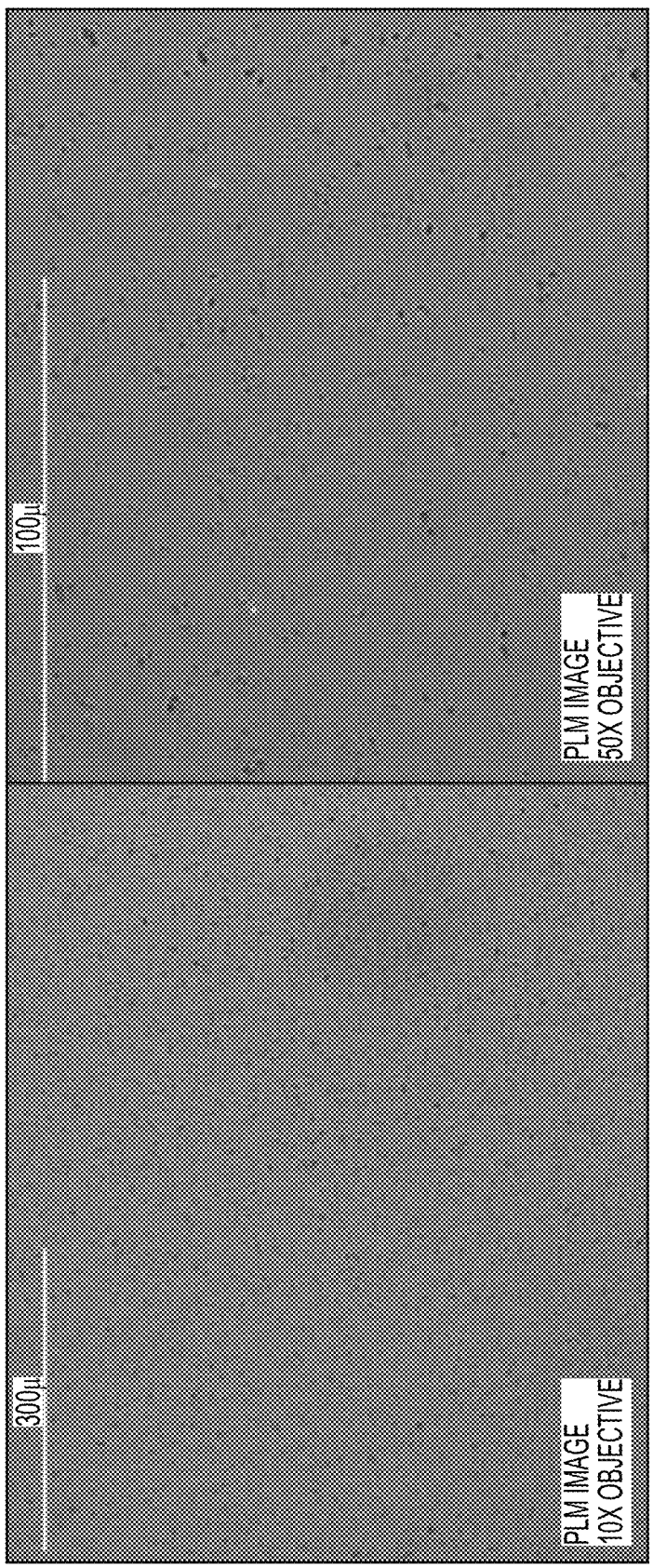
Figure 6:
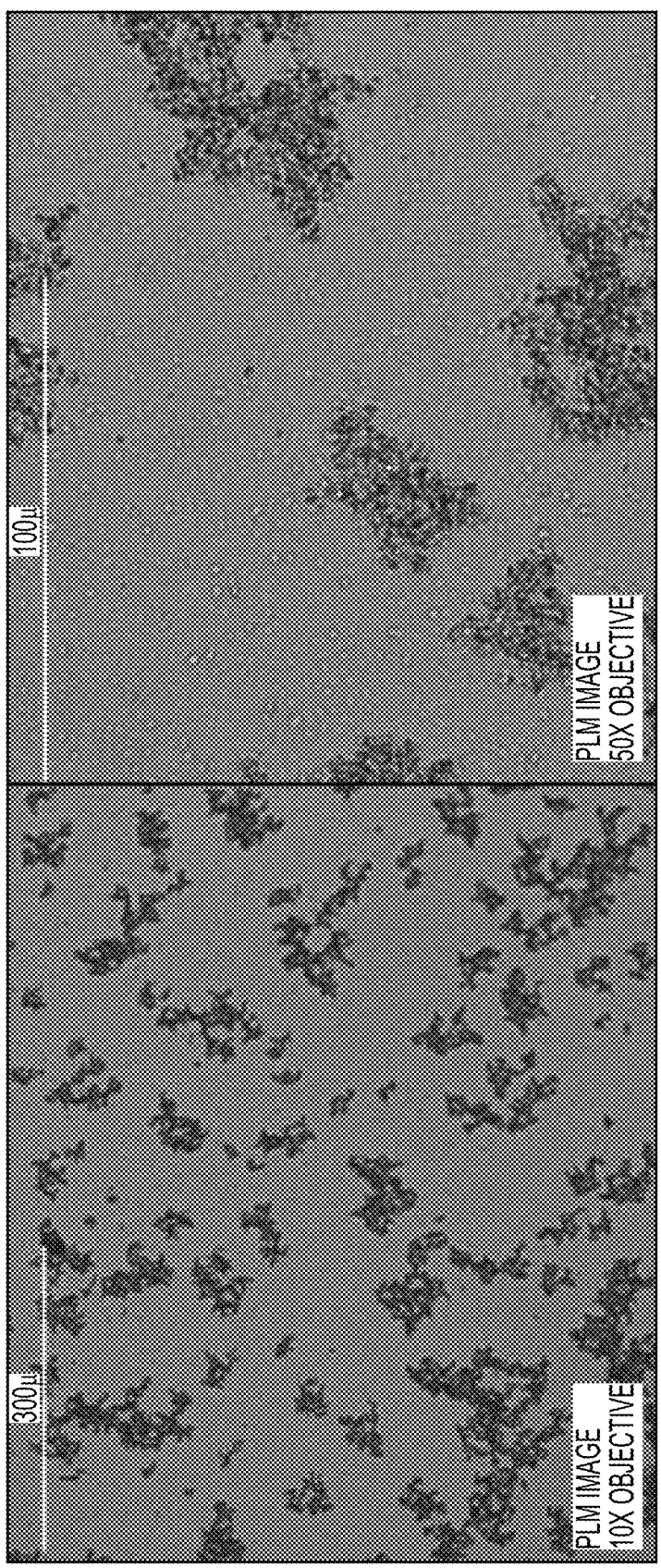

| Formulation vehicle | Particle Size | Results shown in |
|---|---|---|
| PBS/0.1% HPMC | >5 μM | FIG. 3 |
| PBS/0.1% HPMC | <5 μM | FIG. 4 |
| 150 mM NaCl/0.1% HPMC/0.5% Poloxamer 237 | <5 μM | FIG. 5 |
| 150 mM NaCl/0.5% Poloxamer 237 | <5 μM | FIG. 6 |

The results of these experiments are shown in FIG. 2-FIG. 6. As shown in FIG. 2, samples from the pre-milled suspensions readily sedimented ($1^{st}$ and $3^{rd}$ vials in each image) as compared to post milled formulations ($2^{nd}$ and $3^{rd}$ vials; particle size <5 μM). After 24 hr standing, there was complete sedimentation observed in pre-milled samples but only partial sedimentation in post-milled samples (images on right).

Further, as seen in FIGS. 3-6, the pre-milled formulations showed milled formulations (FIG. 3) showed enhanced aggregation as compared to the post-milled formulations (FIGS. 4-6). Of the three post-milled formulations the formulation with 150 mM NaCl and 0.5% Poloxamer 237 (FIG. 6) showed the maximum aggregation.

Example 7: Stability Studies of Exemplary Solution Formulations of the Disclosure (Pre-Lyophilized)

Pre-lyophilized solution formulations of Formula Ia (6.7 mg/mL) were prepared at a range of SBECD (sulfobutyl ether β-cyclodextrin sodium, also called betadex sulfobutyl ether sodium) concentrations and held at ambient and refrigerated conditions, with and without the presence of seeds of crystalline Formula Ia. Samples for freeze-thaw cycling were also prepared and tested. For each condition, the physical stability was measured as % LS (label strength) and compared to % LS at T=0. The results from these experiments are tabulated in Table 1 below. As seen, the 20% and 10% SBECD formulations are physically stable when held at RT and 2-8° C. for 48 hr, with and without seeding. The 20% and 10% SBECD formulations are also physically stable to freeze/thaw cycling (three cycles performed). The 7.5% SBECD formulation is physically stable when held at RT and 2-8° C. for 24 hr, with and without seeding. The 7.5% SBECD formulation is also stable to freeze/thaw cycling (three cycles performed). Precipitation under some conditions was observed at 5% SBECD.

TABLE 1

Stability data for exemplary formulations
6.7 mg/mL Formula Ia, pH 3.5

| | | | % LS After Stress | | | | | |
|---|---|---|---|---|---|---|---|---|
| | | | Hold | | Hold After Seeding** | | Freeze-thaw (3x) | |
| % SBECD w/v | pH | % LS (Initial) | 2-8° C. (48 h) | RT (48 h) | 2-8° C. (48 h) | RT (48 h) | Without seeding | After seeding** |
| 20 | 3.5 | 102 | 101 | 101 | 101 | 101 | 100 | 100 |
| 10 | 3.5 | 101 | 101 | 101 | 99 | 98 | 100 | 98 |
| 7.5 | 3.5 | 101 | 104* | 103* | 103* | 102* | 99 | 97 |
| 5 | 3.5 | 101 | 101 | 101 | 80 | 68 | 101 | 69 |

*24 h timepoint
**seeded with solid crystalline Formula Ia at approximately 10%

Example 8: Stability Studies of Exemplary Solution Formulations (Pre-Lyophilized) Under Stress Conditions Up to pH 3.8

Pre-lyophilized solutions of Formula Ia (6.7 mg/mL) and SBECD (10% w/v SBECD) with pH values 3.8 and 4.0 were set up and analyzed for physical stability. For each conditions, the physical stability was measured as % LS and compared to % LS at T=0. The results of these studies are presented in Tables 2-4 below. As seen, pre-lyophilized solution at pH=3.8 is physically stable for 72 hr when held at RT and 2-8° C., with and without seeding, and is stable for 3× freeze-thaw cycles.

TABLE 2

Stability data of an exemplary formulation at pH 4.0 and 3.8.
6.7 mg/mL Formula Ia; 10% w/v SBECD

| | | % LS After Stress Hold | | | | | | | |
|---|---|---|---|---|---|---|---|---|---|
| pH | % LS T$_0$ | 2-8° C. (24 h) | 2-8° C. (48 h) | 2-8° C. (72 h) | 2-8° C. (1 wk) | RT (24 h) | RT (48h) | RT (72 h) | RT (1 wk) |
| 3.8 | 99 | 100 | 99 | 99 | 99 | 100 | 99 | 99 | 99 |
| 4.0 | 100 | 100 | 99 | 100 | 99 | 100 | 99 | 100 | 98 |

TABLE 3

Stability data of an exemplary formulation at pH 4.0 and 3.8 (with seeding)
6.7 mg/mL Formula Ia; 10% w/v SBECD

| | | % LS After Stress Hold After Seeding** | | | | | | | |
|---|---|---|---|---|---|---|---|---|---|
| pH | % LS T$_0$ | 2-8° C. (24 h) | 2-8° C. (48 h) | 2-8° C. (72 h) | 2-8° C. (1 wk) | RT (24 h) | RT (48 h) | RT (72 h) | RT (1 wk) |
| 3.8 | 99 | 100 | 99 | 99 | 88 | 99 | 99 | 99 | 65 |
| 4.0 | 100 | 96 | 79 | 67 | — | 69 | 60 | 58 | — |

**Seeded with suspension of crystalline Formula Ia at approximately 7.5% (20 uL at 200 mg/mL).

TABLE 4

Stability data of an exemplary formulation at pH 4.0 and 3.8 (3x freeze-thaw cycles) 6.7 mg/mL Formula Ia; 10% w/v SBECD

| pH | % LS $T_0$ | % LS After Stress Freeze-thaw (3X) (−) seed | (+) seed** |
|---|---|---|---|
| 3.8 | 99 | 99 | 99 |
| 4.0 | 100 | 99 | 99 |

**Seeded with suspension of crystalline Formula Ia at approximately 7.5% (20 uL at 200 mg/mL).

Example 9: Chemical Stability Studies of Exemplary Solution Formulations (Pre-Lyophilized) at pH 1.8, 2.0, 3.5, 3.8, and 4.0

Pre-lyophilized formulations of Formula Ia (6.67 mg/mL) and 10% w/w SBECD with variable pH values were set up and analyzed for chemical stability. For each condition, samples were staged at ambient and refrigerated conditions. Samples were analyzed for % assay/degs, appearance, reconstitution time, pH, and compared to T=0. The data from these studies is tabulated in Tables 5 and 6 below. The structures of the key impurities/metabolites are shown below. The results of these experiments show that this formulation is chemically stable.

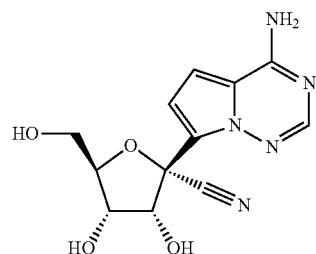

A

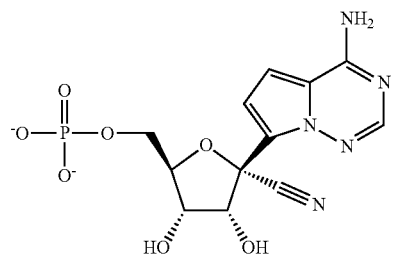

C

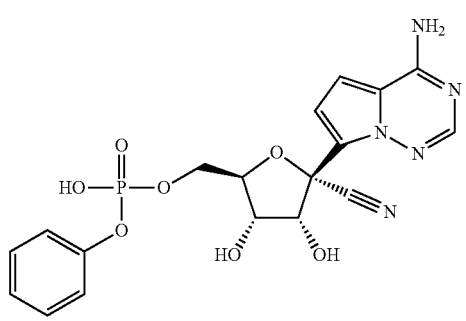

F

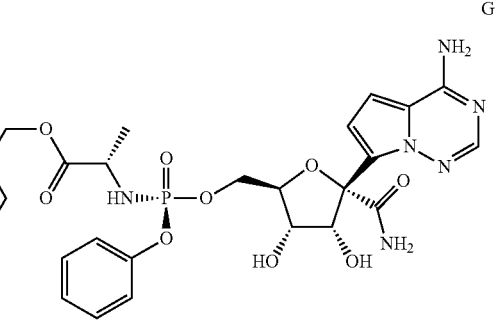

G

TABLE 5

Chemical Stability of exemplary pre-lyo solution formulations at pH 2.0 and 1.8 (degradation identities presented as the difference from T = 0)

| pH | Condition | Time (h) | pH | Formula Ia | Total | C | A | Phenol | F | G | RRT 0.99 |
|---|---|---|---|---|---|---|---|---|---|---|---|
| 2.0 | N/A | 0 | 2.0 | 99.2 | 0.2 | 0.00 | 0.02 | 0.00 | 0.06 | 0.05 | 0.02 |
| | 2-8° C. | 2 | 0.0 | 0.6 | 0.0 | 0.00 | 0.00 | 0.00 | 0.02 | 0.00 | 0.00 |
| | | 3 | 0.0 | 0.2 | 0.0 | 0.00 | 0.00 | 0.00 | 0.02 | 0.00 | 0.00 |
| | | 8 | 0.0 | −0.1 | 0.1 | 0.00 | 0.00 | 0.00 | 0.06 | 0.00 | 0.00 |
| | | 24 | 0.0 | 0.2 | 0.1 | 0.01 | 0.00 | 0.00 | 0.13 | 0.00 | 0.00 |
| | | 48 | 0.0 | −0.5 | 0.3 | 0.01 | 0.01 | 0.00 | 0.25 | 0.00 | 0.00 |
| | Ambient | 1 | 0.0 | 0.1 | 0.0 | 0.00 | 0.00 | 0.00 | 0.03 | 0.00 | 0.00 |
| | | 2 | 0.0 | −0.2 | 0.1 | 0.00 | 0.00 | 0.00 | 0.05 | 0.00 | 0.00 |
| | | 3 | 0.0 | 0.3 | 0.1 | 0.00 | 0.00 | 0.00 | 0.08 | 0.00 | 0.00 |
| | | 8 | 0.0 | −0.2 | 0.2 | 0.01 | 0.01 | 0.00 | 0.22 | 0.00 | 0.00 |
| | | 24 | 0.0 | −0.6 | 0.8 | 0.04 | 0.03 | 0.04 | 0.68 | 0.00 | 0.00 |
| | | 48 | 0.0 | −1.8 | 1.6 | 0.10 | 0.06 | 0.05 | 1.37 | 0.00 | −0.01 |
| 1.8 | N/A | 0 | 1.8 | 99.4 | 0.2 | 0.00 | 0.02 | 0.00 | 0.08 | 0.05 | 0.02 |
| | 2-8° C. | 2 | 0.0 | 0.0 | 0.0 | 0.00 | 0.00 | 0.00 | 0.02 | 0.00 | 0.00 |
| | | 3 | 0.0 | −0.2 | 0.0 | 0.00 | 0.00 | 0.00 | 0.03 | 0.00 | 0.00 |
| | | 8 | 0.0 | −0.2 | 0.1 | 0.00 | 0.00 | 0.00 | 0.08 | 0.00 | 0.01 |
| | | 24 | 0.0 | −0.5 | 0.2 | 0.01 | 0.01 | 0.00 | 0.20 | 0.00 | 0.00 |
| | | 48 | 0.0 | −0.2 | 0.4 | 0.03 | 0.02 | 0.00 | 0.39 | 0.00 | 0.00 |
| | Ambient | 1 | 0.0 | −0.3 | 0.0 | 0.00 | 0.00 | 0.00 | 0.04 | 0.00 | 0.00 |
| | | 2 | 0.0 | −0.1 | 0.1 | 0.00 | 0.00 | 0.00 | 0.08 | 0.00 | 0.00 |
| | | 3 | 0.0 | −0.3 | 0.1 | 0.00 | 0.01 | 0.00 | 0.13 | 0.00 | 0.00 |
| | | 8 | 0.0 | −0.4 | 0.4 | 0.02 | 0.01 | 0.00 | 0.34 | 0.00 | 0.00 |

TABLE 5-continued

Chemical Stability of exemplary pre-lyo solution formulations at pH 2.0 and 1.8 (degradation identities presented as the difference from T = 0)

| pH | Condition | Time (h) | pH | Formula Ia | Total | C | A | Phenol | F | G | RRT 0.99 |
|---|---|---|---|---|---|---|---|---|---|---|---|
| | | 24 | 0.0 | −1.3 | 1.2 | 0.07 | 0.05 | 0.04 | 1.05 | 0.00 | 0.00 |
| | | 48 | 0.0 | −3.5 | 2.4 | 0.16 | 0.09 | 0.08 | 2.09 | 0.00 | 0.00 |

TABLE 6

Chemical Stability of exemplary pre-lyo solution formulations at pH 4.0, 3.8 and 3.5 (degradation identities presented as the difference from T = 0)

| pH | Condition | Time (h) | pH | Formula Ia | Total | C | A | Phenol | F | G | RRT 0.99 | RRT 1.47 |
|---|---|---|---|---|---|---|---|---|---|---|---|---|
| 4.0 | N/A | 0 | 4.0 | 98.6 | 0.1 | NT | 0.02 | NT | 0.02 | 0.06 | 0.02 | 0.00 |
| | 2-8° C. | 7.2 | 0.0 | 0.0 | 0.0 | NT | 0.00 | NT | 0.00 | 0.00 | 0.00 | 0.00 |
| | | 24 | 0.0 | 0.3 | 0.0 | NT | 0.00 | NT | 0.00 | 0.00 | 0.00 | 0.00 |
| | | 96 | 0.0 | 0.2 | 0.0 | NT | 0.00 | NT | 0.01 | 0.00 | 0.00 | 0.00 |
| | | 168 | −0.1 | 0.6 | 0.0 | NT | 0.00 | NT | 0.01 | 0.00 | 0.00 | 0.00 |
| | Ambient | 7.2 | 0.0 | 0.3 | 0.0 | NT | 0.00 | NT | 0.00 | 0.00 | 0.00 | 0.00 |
| | | 24 | 0.0 | 0.3 | 0.0 | NT | 0.00 | NT | 0.01 | 0.00 | 0.00 | 0.00 |
| | | 96 | 0.0 | 0.0 | 0.1 | NT | 0.00 | NT | 0.04 | 0.00 | 0.00 | 0.03 |
| | | 168 | −0.1 | −0.2 | 0.1 | NT | 0.00 | NT | 0.07 | 0.00 | 0.00 | 0.04 |
| 3.8 | N/A | 0 | 3.8 | 98.7 | 0.1 | NT | 0.02 | NT | 0.02 | 0.05 | 0.02 | 0.00 |
| | 2-8° C. | 7.2 | −0.1 | −0.2 | 0.0 | NT | 0.00 | NT | 0.00 | 0.00 | 0.00 | 0.00 |
| | | 24 | 0.0 | 0.3 | 0.0 | NT | 0.00 | NT | 0.00 | 0.00 | 0.00 | 0.00 |
| | | 96 | −0.1 | 0.1 | 0.0 | NT | 0.00 | NT | 0.01 | 0.00 | 0.00 | 0.00 |
| | | 168 | −0.1 | 0.1 | 0.0 | NT | 0.00 | NT | 0.01 | 0.00 | 0.00 | 0.00 |
| | Ambient | 7.2 | 0.0 | 0.0 | 0.0 | NT | 0.00 | NT | 0.01 | 0.00 | 0.00 | 0.00 |
| | | 24 | 0.0 | 0.4 | 0.0 | NT | 0.00 | NT | 0.02 | 0.00 | 0.00 | 0.00 |
| | | 96 | −0.1 | 0.0 | 0.1 | NT | 0.00 | NT | 0.06 | 0.00 | 0.00 | 0.00 |
| | | 168 | −0.1 | 0.0 | 0.1 | NT | 0.00 | NT | 0.10 | 0.00 | 0.00 | 0.00 |
| 3.5 | N/A | 0 | 3.5 | 99.1 | 0.1 | 0.00 | 0.02 | 0.00 | 0.02 | 0.05 | 0.02 | 3.5 |
| | 2-8° C. | 2 | 0.0 | 0.6 | 0.0 | 0.00 | 0.00 | 0.00 | 0.00 | 0.00 | 0.00 | 0.0 |
| | | 8 | 0.0 | 0.3 | 0.0 | 0.00 | 0.00 | 0.00 | 0.00 | 0.00 | 0.00 | 0.0 |
| | | 24 | −0.1 | 0.7 | 0.0 | 0.00 | 0.00 | 0.00 | 0.00 | 0.00 | 0.00 | −0.1 |
| | | 48 | 0.0 | 0.5 | 0.0 | 0.00 | 0.00 | 0.00 | 0.01 | 0.00 | 0.00 | 0.0 |
| | | 72 | −0.1 | 0.7 | 0.0 | 0.00 | 0.00 | 0.00 | 0.01 | 0.00 | 0.00 | −0.1 |
| | | 96 | 0.0 | 0.2 | 0.0 | 0.00 | 0.00 | 0.00 | 0.02 | 0.00 | −0.01 | 0.0 |
| | | 168 | 0.0 | 0.6 | 0.0 | 0.01 | 0.00 | 0.00 | 0.03 | 0.00 | 0.00 | 0.0 |
| | Ambient | 2 | 0.0 | 0.6 | 0.0 | 0.00 | 0.00 | 0.00 | 0.00 | 0.00 | 0.00 | 0.0 |
| | | 8 | 0.0 | 0.2 | 0.0 | 0.00 | 0.00 | 0.00 | 0.01 | 0.00 | 0.00 | 0.0 |
| | | 24 | 0.0 | 0.6 | 0.0 | 0.00 | 0.00 | 0.00 | 0.03 | 0.00 | 0.00 | 0.0 |
| | | 48 | 0.0 | 0.3 | 0.1 | 0.00 | 0.00 | 0.00 | 0.05 | 0.00 | 0.00 | 0.0 |
| | | 72 | −0.1 | 0.2 | 0.1 | 0.00 | 0.00 | 0.00 | 0.08 | 0.00 | 0.00 | −0.1 |
| | | 96 | 0.0 | 0.0 | 0.1 | 0.00 | 0.01 | 0.00 | 0.11 | 0.00 | 0.00 | 0.0 |
| | | 168 | 0.0 | 0.2 | 0.2 | 0.01 | 0.01 | 0.00 | 0.19 | 0.00 | 0.00 | 0.0 |

Example 10: Stability Testing of Exemplary Lyophilized Formulations

The following lyophilized drug product of Formula Ia were prepare and placed into temperature and humidity controlled chambers for predefined time intervals and removed for testing. The drug product vials were tested using analytical methods determined to be stability indicating such as liquid chromatography to monitor product purity. The results of these stability experiments are summarized on Tables 7-9 below.

| Formulation | Pre-lyophilization | Lyophilized |
|---|---|---|
| I | 6.67 mg/mL Formula Ia; 10% SBECD pH 3.5 | 6.25% w/w Formula Ia 93.75% SBECD |
| II | 6.67 mg/mL Formula Ia; 20% SBECD pH 3.5 | 3.23% w/w Formula Ia 96.77% w/w SBECD |

TABLE 7

Four weeks stability data for exemplary lyophilized formulations at 80° C.

| Formulation | Time Point (at 80° C.) | % LS | Total Imp/Deg (%) | Individual Deg Compound F | RRT 0.48 | Compound G |
|---|---|---|---|---|---|---|
| I | T = 0 | 98.9 | 0.1 | 0.03 | — | 0.05 |
| | 1 week | 98.3 | 0.4 | 0.16 | 0.09 | 0.14 |

TABLE 7-continued

Four weeks stability data for exemplary lyophilized formulations at 80° C.

| Formulation | Time Point (at 80° C.) | % LS | Total Imp/Deg (%) | Individual Deg Compound F | RRT 0.48 | Compound G |
|---|---|---|---|---|---|---|
|  | 2 weeks | 97.9 | 0.7 | 0.26 | 0.15 | 0.20 |
|  | 4 weeks | 97.0 | 1.1 | 0.43 | 0.25 | 0.30 |
| II | T = 0 | 98.7 | 0.1 | 0.04 | — | 0.05 |
|  | 1 week | 98.2 | 0.4 | 0.22 | 0.05 | 0.12 |
|  | 2 weeks | 97.5 | 0.7 | 0.33 | 0.09 | 0.17 |
|  | 4 weeks | 96.7 | 1.1 | 0.57 | 0.16 | 0.25 |

TABLE 8

Accelerated chemical stability of exemplary lyophilized formulations at 40° C. 75% RH

| | | Formulation I Condition and Duration | | Formulation II Condition and Duration | | | | | |
|---|---|---|---|---|---|---|---|---|---|
| | | | | Lot 1 | | Lot 2 | | Lot 3 | |
| Test | Compound | Initial | 40° C./ 75% RH 1 Month | Initial | 40° C./ 75% RH 6 Month | Initial | 40° C./ 75% RH 6 Month | Initial | 40° C./ 75% RH 6 Month |
| Assay (%) | Formula Ia | 100.7 | 99.9 | 101.5 | 100.5 | 99.8 | 99.9 | 100.0 | 98.5 |
| Degradation Product Content (%) | Compound C | ND | ND | — | — | — | — | — | — |
|  | Compound A | 0.02 | 0.02 | ND | ND | ND | ND | ND | ND |
|  | Phenol | ND | ND | — | — | — | — | — | — |
|  | Compound F | 0.05 | 0.07 | 0.14 | 0.18 | TR | TR | TR | 0.10 |
|  | RRT 0.48 | ND | 0.00 | — | — | — | — | — | — |
|  | Compound G | 0.05 | 0.06 | — | 0.11 | — | — | — | — |
|  | Total Impurities | 0.0 | 0.1 | 0.1 | 0.3 | 0.0 | 0.0 | 0.0 | 0.1 |
| Water Content (%) | % (w/w) | 0.9 | 1.0 | 1.3 | 1.3 | 1.2 | 1.3 | 1.2 | 1.2 |
| Reconstitution Time (seconds) | N/A | 62 | 83 | 75 | 165 | 110 | 180 | 105 | 180 |
| pH of Solution | N/A | 3.4 | 3.4 | 3.6 | 3.6 | 3.7 | 3.7 | 3.7 | 3.6 |

TABLE 9

Chemical stability of exemplary lyophilized formulations at 60° C. and −20° C.

| | | Formulation I Condition and Duration | | | Formulation II Condition and Duration | | |
|---|---|---|---|---|---|---|---|
| Stability Report Summary | | | 60° C. | −20° C. | | 60° C. | −20° C. |
| Test | Compound | Initial | 2 Weeks | 1 Month | 1 Month | Initial | 1 Month | 1 Month |
| Assay (%) | Formula Ia | 100.7 | 99.4 | 99.9 | 99.9 | 98.5 | 98.1 | 98.3 |
| Degradation Product Content (%) | Compound C | ND | ND | ND | ND | — | — | — |
|  | Compound A | 0.02 | 0.02 | 0.02 | 0.02 | ND | ND | ND |
|  | Phenol | ND | ND | ND | ND | — | — | — |
|  | Compound F | 0.05 | 0.09 | 0.15 | 0.05 | 0.11 | 0.19 | 0.11 |
|  | RRT 0.48 | ND | 0.03 | 0.05 | 0.00 | — | — | — |
|  | Compound G | 0.05 | 0.09 | 0.12 | 0.05 | — | 0.12 | — |
|  | Total Impurities | 0.0 | 0.2 | 0.3 | 0.1 | 0.1 | 0.3 | 0.1 |
| Water Content (%) | % (w/w) | 0.9 | 1.0 | 1.0 | 0.9 | 1.1 | 1.1 | 1.2 |
| Reconstitution Time (seconds) | N/A | 62 | 94.0 | 54 | 74 | 135 | 150 | 150 |
| pH of Solution | N/A | 3.4 | 3.4 | 3.4 | 3.4 | 3.5 | 3.5 | 3.5 |

Example 11: Stability Testing of Exemplary Reconstituted Lyophilized Formulations Simulated reconstituted solutions were prepared and diluted into normal saline (0.9% NaCl), mimicking dilutions into 50 mL and 500 mL IV bags. Target pH and upper limits of pH spec were analyzed over time at ambient and refrigerated conditions. As seen in the data presented in Table 4 below, all pH solutions are physically stable up to 24 h once diluted into normal saline and held at ambient and refrigerated conditions.

TABLE 10

Stability of reconstituted solutions of varying pH.

| Formulation | After dilution into Normal Saline Formula Ia mg/mL | pH | % LS Initial | 24 h 2-8° C. | 24 h RT | 48 h 2-8° C. | 48 h RT |
|---|---|---|---|---|---|---|---|
| 6.67 mg/mL Formula Ia 10% SBECD pH 3.5 | 0.2 | 4.1 | 98 | 100 | 100 | — | — |
|  | 2.0 | 3.7 | 99 | 101 | 100 | — | — |
| 6.67 mg/mL Formula Ia 10% SBECD pH 3.8 | 0.2 | 4.2 | 98 | 97 | 97 | 97 | 96 |
|  | 2.0 | 3.9 | 100 | 100 | 100 | 101 | 101 |
| 6.67 mg/mL Formula Ia 10% SBECD pH 4.0 | 0.2 | 4.2 | 97 | 97 | 96 | 97 | 96 |
|  | 2.0 | 4.0 | 100 | 100 | 99 | 100 | 99 |

Example 12: Stability Comparison of Exemplary Reconstituted Lyophilized Formulations The following lyophilized formulations were prepared.

| Formulation | Pre-lyophilization | Lyophilized |
|---|---|---|
| I | 6.67 mg/mL Formula Ia 10% SBECD pH 3.5 | 6.25% w/w Formula Ia 93.75% w/w SBECD |
| II | 6.67 mg/mL Formula Ia 20% SBECD pH 3.5 | 3.23% w/w Formula Ia 96.77% w/w SBECD |

The lyophilized cakes were reconstituted with SWFI (sterile water for injection) and subsequently diluted into normal saline (0.9% NaCl), mimicking dilutions into 50 mL and 500 mL IV bags. A head-to-head comparison of the physical stability of the 10% SBECD formulation and the 20% SBECD formulation was made. The results are summarized in Tables 11 and 12 below. As seen, the 10% SBECD is physically stable up to 48 hr (without seed) at ambient and refrigerated conditions once diluted into normal saline.

TABLE 11

Stability data for exemplary reconstituted formulations

| Formulation | After dilution into normal saline Formula Ia mg/mL | pH | % LS Initial | % LS After Stress Hold 24 h 2-8° C. | 24 h RT | 48 h 2-8° C. | 48 h RT | 72 h 2-8° C. | 72 h RT |
|---|---|---|---|---|---|---|---|---|---|
| I | 0.2 | 4.2 | 105 | 103 | 103 | 104 | 100 | 104 | 92 |
|  | 2.0 | 3.6 | 106 | 106 | 106 | 106 | 106 | 106 | 107 |
| II | 0.2 | 4.2 | 100 | 99 | 99 | 99 | 99 | 99 | 99 |
|  | 2.0 | 3.8 | 101 | 101 | 102 | 102 | 101 | 102 | 102 |

TABLE 12

Stability data for exemplary reconstituted formulations

| Formulation | After dilution into normal saline Formula Ia mg/mL | pH | % LS Initial | % LS After Stress Hold After Seeding* 3 h 2-8° C. | 3 h RT | 6 h 2-8° C. | 6 h RT | 24 h 2-8° C. | 24 h RT | 48 h 2-8° C. | 48 h RT |
|---|---|---|---|---|---|---|---|---|---|---|---|
| I | 0.2 | 4.2 | 105 | 96 | 92 | 90 | 84 | 66 | 48 | — | — |
|  | 2.0 | 3.6 | 106 | — | — | 106 | 102 | 106 | 89 | 106 | 80 |
| II | 0.2 | 4.2 | 100 | 96 | 93 | 93 | 91 | 83 | 70 | — | — |
|  | 2.0 | 3.8 | 101 | — | — | 102 | 102 | 101 | 101 | 101 | 101 |

*Seeded with 10% crystalline Formula Ia (suspension)

Note:
Test solutions were prepared from lyo cakes reconstituted by the addition of 19 mL SWFI; then diluted 25x or 2.5x fold to achieve target concentrations.

Example 13: In Use Testing of Reconstituted Solutions

Following lyophilized formulation was prepared:

| Pre-lyophilization | Lyophilized |
|---|---|
| 6.67 mg/mL Formula Ia; 10% SBECD; pH 3.5 | 93.75% w/w Formula Ia; 97.25% SBECD |

Lyophilized cakes were reconstituted and diluted into IV bags for final Formula Ia concentrations of 2.0 mg/mL and 0.3 mg/mL. The IV bags and IV tubings were sampled over time and tested for % assay/degradation. The data from these studies is tabulated in Table 13 below. As seen, the tested formulation is stable when held at RT up to 24 hr, and 2-8° C. for 48 hr. Similarly, the formulation is stable when held in tubing up to 6 hr (12× longer than the assumed infusion time of 30 min).

TABLE 13

In use stability data of an exemplary formulation

| Formula Ia (in 100 mL 0.9% Saline) | Condition | Time Point | Formula Ia | Total | C | A | Phenol | F | G | RRT 0.99 |
|---|---|---|---|---|---|---|---|---|---|---|
| 200 mg (IV Bag) | N/A | T = 0 | 100.4 | 0.2 | 0.00 | 0.02 | 0.00 | 0.06 | 0.05 | 0.02 |
|  | Ambient | 4 h | 100.3 | 0.2 | 0.00 | 0.02 | 0.00 | 0.06 | 0.06 | 0.02 |
|  |  | 8 h | 100.2 | 0.2 | 0.00 | 0.02 | 0.00 | 0.06 | 0.06 | 0.02 |
|  |  | 24 h | 100.3 | 0.2 | 0.00 | 0.02 | 0.00 | 0.08 | 0.06 | 0.02 |
|  | N/A | T = 0 | 100.1 | 0.2 | 0.00 | 0.02 | 0.00 | 0.06 | 0.05 | 0.02 |
|  | 2-8° C. | 24 h | 99.8 | 0.2 | 0.00 | 0.02 | 0.00 | 0.06 | 0.05 | 0.02 |
|  |  | 48 h | 100.2 | 0.2 | 0.00 | 0.02 | 0.00 | 0.06 | 0.06 | 0.02 |
| 30 mg (IV Bag) | N/A | T = 0 | 100.9 | 0.2 | 0.00 | 0.02 | 0.00 | 0.06 | 0.05 | 0.03 |
|  | Ambient | 4 h | 100.8 | 0.2 | 0.00 | 0.02 | 0.00 | 0.06 | 0.06 | 0.02 |
|  |  | 8 h | 100.5 | 0.2 | 0.00 | 0.02 | 0.00 | 0.07 | 0.06 | 0.03 |
|  |  | 24 h | 100.4 | 0.2 | 0.00 | 0.02 | 0.00 | 0.08 | 0.06 | 0.02 |
|  | N/A | T = 0 | 100.6 | 0.2 | 0.00 | 0.02 | 0.00 | 0.06 | 0.05 | 0.02 |
|  | 2-8° C. | 24 h | 100.7 | 0.2 | 0.00 | 0.02 | 0.00 | 0.07 | 0.05 | 0.02 |
|  |  | 48 h | 101.1 | 0.2 | 0.00 | 0.02 | 0.00 | 0.06 | 0.06 | 0.02 |
| 200 mg (IV Tube) | Ambient | 6 h | 100.2 | 0.2 | 0.00 | 0.02 | 0.00 | 0.06 | 0.05 | 0.02 |
| 30 mg (IV Tube) | Ambient | 6 Hours | 99.4 | 0.2 | 0.00 | 0.03 | 0.00 | 0.06 | 0.06 | 0.02 |

Results presented as % w/w.
A = "Compound A";
C = "Compound C";
F = "Compound F";
G = "Compound G"

Example 14: Pharmacokinetics Profiles of Exemplary Formulations

PK studies in cyno monkeys (10 mg/Kg intravenous dose of Formula Ia) were conducted with the following exemplary lyophilized formulations. Each formulation was prepared by the addition of 19 mL of sterile water for injection to the lyophilized cake followed by agitation to ensure a uniform reconstituted solution. The reconstituted solution was then sterile filtered prior to administration by IV over the course of 30 minutes. Each formulation was administered to n=3 male cyno monkeys at a concentration of 5 mg/mL and a dose volume of 2 mL/kg for a total dose of 10 mg/kg. For each formulation, plasma samples were collected at the following time intervals: predose, 0.25, 0.48 (before end of infusion), 0.58, 1, 2, 4, 8, 12, and 24 hours postdose (based on the start of infusion). For each formulation, samples for PBMC analysis were taken at intervals of 4 and 24 hours postdose (based on the start of infusion).

| Formulation | Pre-lyophilization | Lyophilized |
|---|---|---|
| I | 6.67 mg/mL Formula Ia 10% SBECD pH 3.5 | 6.25% w/w Formula Ia 93.75% SBECD |
| II | 6.67 mg/mL Formula Ia 20% SBECD pH 3.5 | 3.23% w/w Formula Ia 96.77% SBECD |

Figure 7:
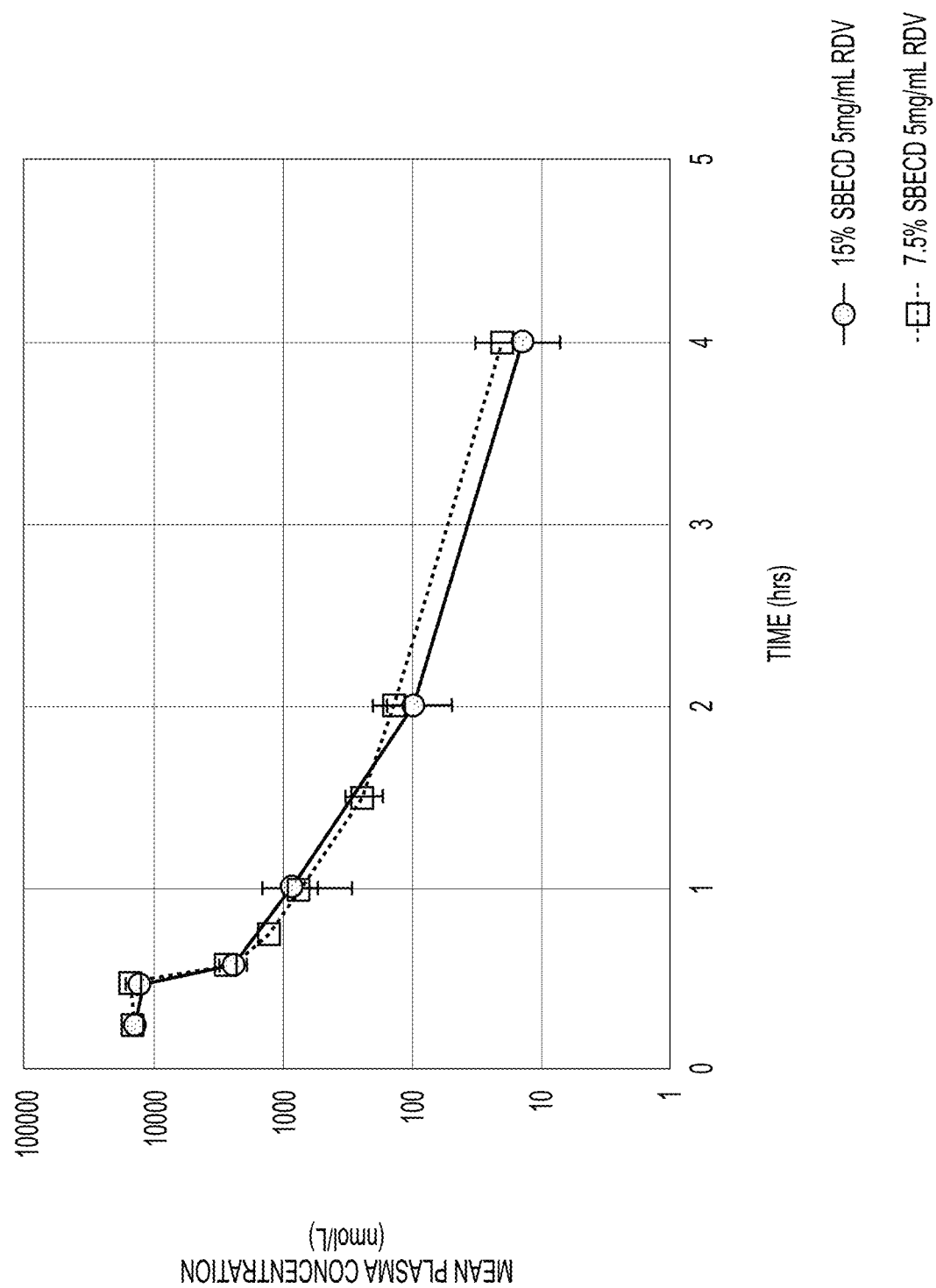

The results from these experiments are tabulated in Table 14 below and shown in FIG. 7. As seen, the two exemplary formulations exhibit similar concentration-time profiles.

TABLE 14

PK data for exemplary formulations

| | | Mean PK Parameter of the Compound of Formula Ia | | | | |
|---|---|---|---|---|---|---|
| Formulation | Dose | $AUC_{inf}$ (hr*nmol/L) | $AUC_{last}$ (hr*nmol/L) | $C_{max}$ (nmol/L) | $t_{1/2}$ (hr) | $T_{max}$ (hr) |
| II | 10 mg/kg | 7030 ± 1140 | 7020 ± 1150 | 14500 ± 2430 | 0.41 ± 0.14 | 0.33 ± 0.13 |
| I | 10 mg/kg | 7320 ± 626 | 7290 ± 624 | 15500 ± 1210 | 0.52 ± 0.22 | 0.48 ± 0.00 |

Example 15: SARS-CoV-2 Antiviral Screening $1.2 \times 10^4$ A549-hACE2 cells in 50 μl phenol red-free DMEM medium supplemented with 2% FBS were seeded in each well of a white opaque 96-well plate (Corning, Cat #3916). On the next day, 2-fold serial dilutions of compounds were prepared in DMSO. The compounds were further diluted as 100 folds in the 2% FBS culture medium. Cell culture fluids were removed and incubated with 50 μl diluted compound solutions and 50 μl of SARS-CoV2-Nano viruses (MOI 0.025). At 48 h post-infection, 50 μl Nano luciferase substrates (Promega, Cat #N1150) were added to each well. Luciferase signals were measured using a Synergy™ Neo2 Multi-Mode microplate reader (BioTek). The relative luciferase signals were calculated by normalizing the luciferase signals of the compound-treated groups to that of the DMSO-treated groups (expressed in percentages). The relative luciferase signals (Y axis) to the log 10 values of compound concentration (X axis) were plotted in the software GraphPad Prism 8. The $EC_{50}$ (compound concentration for reducing 50% of luciferase signals) were calculated using a nonlinear regression model (four parameters).

Using this assay, the $EC_{50}$ for the compound of Formula Ia was calculated as 110 nM.

Example 16: Determination of the Compound of Formula Ia and its Metabolites in AGM PBMCs, Nasal Mucosa, Respiratory, Liver and Kidney Tissues Following Inhalation Administration A single dose pharmacokinetic study with the compound of Formula Ia (RDV, remdesivir or GS-5734) was carried out in male and female African Green Monkeys (AGM). Remdesivir IV formulation (lyophilized powder containing 105 mg of the compound of Formula Ia (3.23% w/w) and 3146 mg of sulfobutylether-β-cyclodextrin sodium Salt (SBECD, Betadex Sulfobutyl Ether Sodium; 96.77% w/w) reconstituted with 19 mL of water for injection to obtain a solution of 5 mg/mL the compound of Formula Ia and 150 mg/mL SBECD at pH 3.6 (range of 3.0-4.0)) was aerosolized using a compressed air nebulizer. The aerosolized compound of Formula Ia was administered by inhalation to AGMs via a head-dome apparatus for 30 (Group 1; n=4) and 90 minutes (Group 2; n=4). The exposure times resulted in an average presented dose of 0.672 mg/kg and 2.14 mg/kg, respectively. The average deposited dose was calculated at 0.168 mg/kg and 0.536 mg/kg, respectively. Plasma, peripheral blood mononuclear cells (PBMCs), trachea, bronchi, lung lobe, liver, kidney, nasal mucosa and nasopharyngeal mucosa samples were collected in this study.

Figure 8:
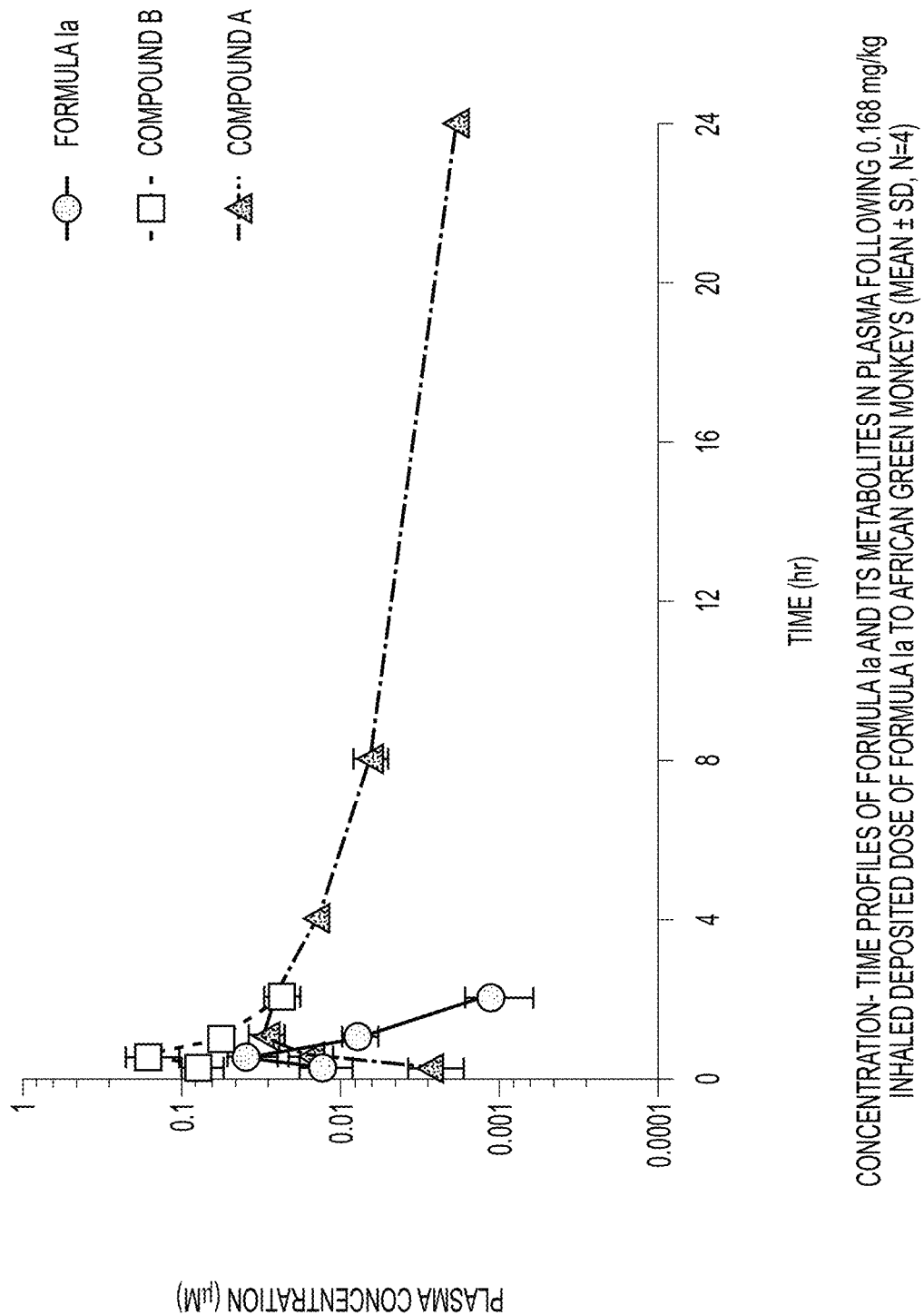
Figure 9:
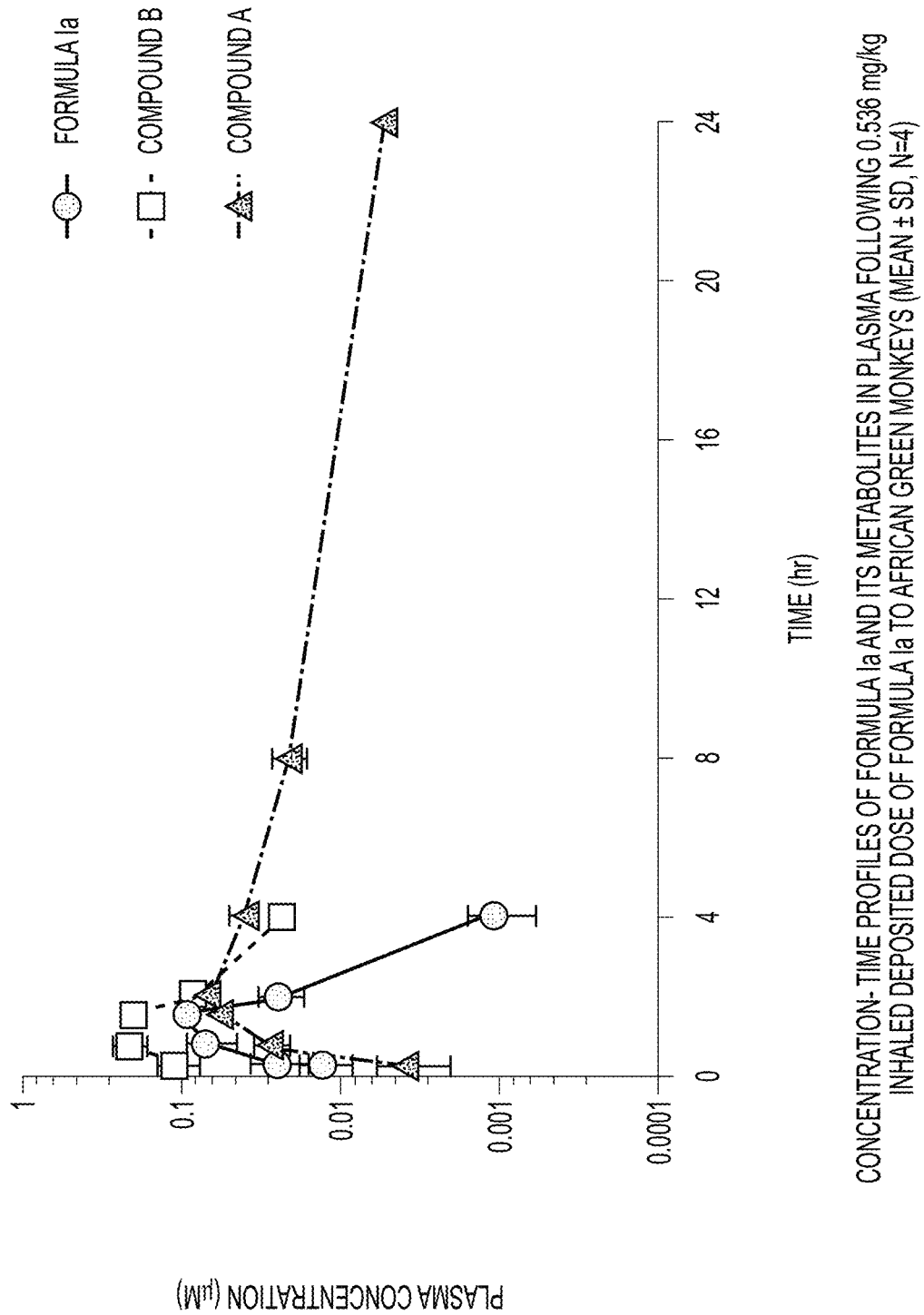

Plasma: Concentrations of the compound of Formula Ia and its two metabolites, A (an adenosine nucleoside analog), and B (an intermediate metabolite) shown below, were determined in plasma by LC/MS/MS. Mean plasma concentrations for the compound of Formula Ia and its metabolites in male and female AGM following head dome inhalation administration of a deposited dose of the compound of Formula Ia at 0.168 mg/kg and 0.536 mg/kg are reported in Table 15 and Table 16, respectively. Plasma pharmacokinetic parameters are summarized in Table 17. Mean plasma concentration-time profiles for the compound of Formula Ia and its metabolites at 0.168 mg/kg and 0.536 mg/kg dose levels are plotted in FIG. 8 and FIG. 9, respectively.

TABLE 15

Mean plasma concentrations of the compound of Formula Ia and its metabolites following 0.168 mg/kg inhaled deposited dose of the compound of Formula Ia to African Green Monkeys (mean ± SD, n = 4)

| Time | Plasma Concentration (μM) | | |
|---|---|---|---|
| (h) | Formula Ia | B | A |
| Pre-dose | BLQ | BLQ | BLQ |
| 0.25 | 0.013 ± 0.005 | 0.077 ± 0.021 | 0.003 ± 0.001 |
| 0.52 | 0.039 ± 0.014 | 0.163 ± 0.062 | 0.017 ± 0.005 |
| 1 | 0.008 ± 0.002 | 0.057 ± 0.011 | 0.031 ± 0.007 |
| 2 | 0.001 ± 0.000 | 0.023 ± 0.002 | 0.025 ± 0.005 |
| 4 | BLQ | BLQ | 0.014 ± 0.002 |
| 8 | BLQ | BLQ | 0.007 ± 0.002 |
| 24 | BLQ | BLQ | 0.002 ± 0.000 |

BLQ: Below lower limit of quantitation. For Formula Ia: 0.001 μM; for B: 0.019 μM; for A: 0.001 μM.

TABLE 16

Mean plasma concentrations of the compound of Formula Ia and its metabolites following 0.536 mg/kg inhaled deposited dose of the compound of Formula Ia to African Green Monkeys (mean ± SD, n = 4)

| Time | Plasma Concentration (μM) | | |
|---|---|---|---|
| (h) | Formula Ia | B | A |
| Pre-dose | BLQ | BLQ | BLQ |
| 0.25 | 0.026 ± 0.012 | 0.112 ± 0.032 | 0.004 ± 0.002 |
| 0.75 | 0.070 ± 0.024 | 0.222 ± 0.027 | 0.029 ± 0.008 |

TABLE 16-continued

Mean plasma concentrations of the compound of Formula Ia and its metabolites following 0.536 mg/kg inhaled deposited dose of the compound of Formula Ia to African Green Monkeys (mean ± SD, n = 4)

| Time (h) | Plasma Concentration (µM) | | |
|---|---|---|---|
|  | Formula Ia | B | A |
| 1.52 | 0.101 ± 0.019 | 0.210 ± 0.043 | 0.058 ± 0.003 |
| 2 | 0.026 ± 0.008 | 0.086 ± 0.004 | 0.071 ± 0.011 |
| 4 | 0.001 ± 0.001 | 0.024 ± 0.004 | 0.043 ± 0.009 |
| 8 | BLQ | BLQ | 0.022 ± 0.005 |
| 24 | BLQ | BLQ | 0.005 ± 0.001 |

BLQ: Below lower limit of quantitation. For Formula Ia: 0.001 µM; for B: 0.019 µM; for A: 0.001 µM

TABLE 17

Mean PK parameters of the compound of Formula Ia and its metabolites following 0.168 mg/kg or 0.536 mg/kg inhaled deposited dose of the compound of Formula Ia to African Green Monkeys (mean ± SD, n = 4)

| PK Parameter | 0.168 mg/kg | | | 0.536 mg/kg | | |
|---|---|---|---|---|---|---|
|  | Formula Ia | B | A | Formula Ia | B | A |
| $C_{max}$ (µM) | 0.039 ± 0.014 | 0.163 ± 0.062 | 0.031 ± 0.007 | 0.101 ± 0.019 | 0.229 ± 0.030 | 0.071 ± 0.011 |
| $T_{max}$ (h) | 0.520 ± 0.000 | 0.520 ± 0.000 | 1.00 ± 0.00 | 1.53 ± 0.00 | 0.945 ± 0.390 | 2.00 ± 0.00 |
| $AUC_{0-24}$ (µM · h) | 0.023 ± 0.008 | 0.126 ± 0.031 | 0.191 ± 0.030 | 0.146 ± 0.045 | 0.418 ± 0.051 | 0.539 ± 0.076 |
| $T_{1/2}$ (h) | 0.273 ± 0.069 | 0.534 ± 0.243 | 7.58 ± 1.03 | 0.342 ± 0.099 | 0.894 ± 0.157 | 7.10 ± 0.36 |

Following inhalation administration of the compound of Formula Ia at a calculated deposited dose of 0.168 mg/kg or 0.536 mg/kg, plasma levels of the compound of Formula Ia increased during inhalation exposure and then rapidly cleared from the systemic circulation upon dose cessation with an elimination half-life of 0.273 or 0.342 h, respectively. Metabolite A slowly appeared in plasma and persisted over the 24-hour time course with a mean estimated terminal elimination half-life of 7.58 or 7.10 h following dosing at either 0.168 mg/kg or 0.536 mg/kg, respectively.

PBMC: Concentrations of the compound of Formula Ia and metabolites A, B, C, D, and E shown below, were determined in PBMCs and tissues by LC/MS/MS. Mean PBMC concentrations of B, A, C, D, and E in AGM following head dome inhalation of the compound of Formula Ia at 0.168 mg/kg and 0.536 mg/kg are reported in Table 18 and Table 19, respectively.

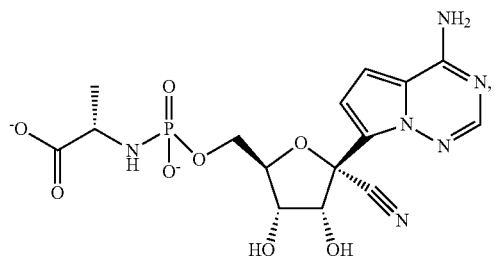

B

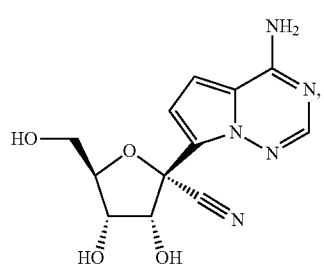

A

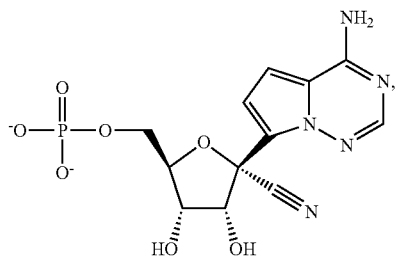

C

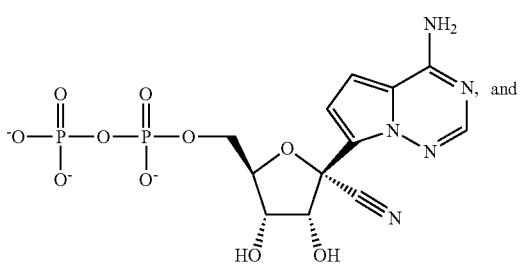

D

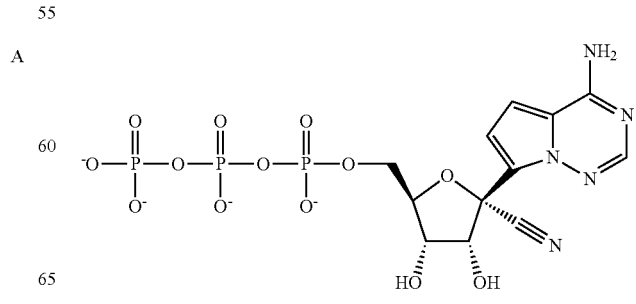

E

TABLE 18

PBMC concentrations of A, B, C, D, and E following 0.168 mg/kg inhaled deposited dose of the compound of Formula Ia to African Green Monkeys (mean ± SD, n = 4)

| Time | Total PBMC Concentrations (μM) | | | | |
|---|---|---|---|---|---|
| (h) | A | B | C | D | E |
| 2 | 0.331 ± 0.092 | 0.105 ± 0.022 | 0.024 ± 0.010 | 0.042 ± 0.023 | 0.071 ± 0.033 |
| 24 | 0.302 ± 0.044 | 0.093 ± 0.024 | 0.009 ± 0.006 | 0.026 ± 0.012 | 0.047 ± 0.023 |

TABLE 19

PBMC concentrations of A, B, C, D, and E following 0.536 mg/kg inhaled deposited dose of the compound of Formula Ia to African Green Monkeys (mean ± SD, n = 4)

| Time | Total PBMC Concentrations (μM) | | | | |
|---|---|---|---|---|---|
| (h) | A | B | C | D | E |
| 2 | 0.409 ± 0.065 | 0.257 ± 0.095 | 0.048 ± 0.022 | 0.133 ± 0.027 | 0.238 ± 0.041 |
| 24 | 0.457 ± 0.130 | 0.115 ± 0.030 | 0.021 ± 0.007 | 0.053 ± 0.020 | 0.127 ± 0.040 |

Figure 10:
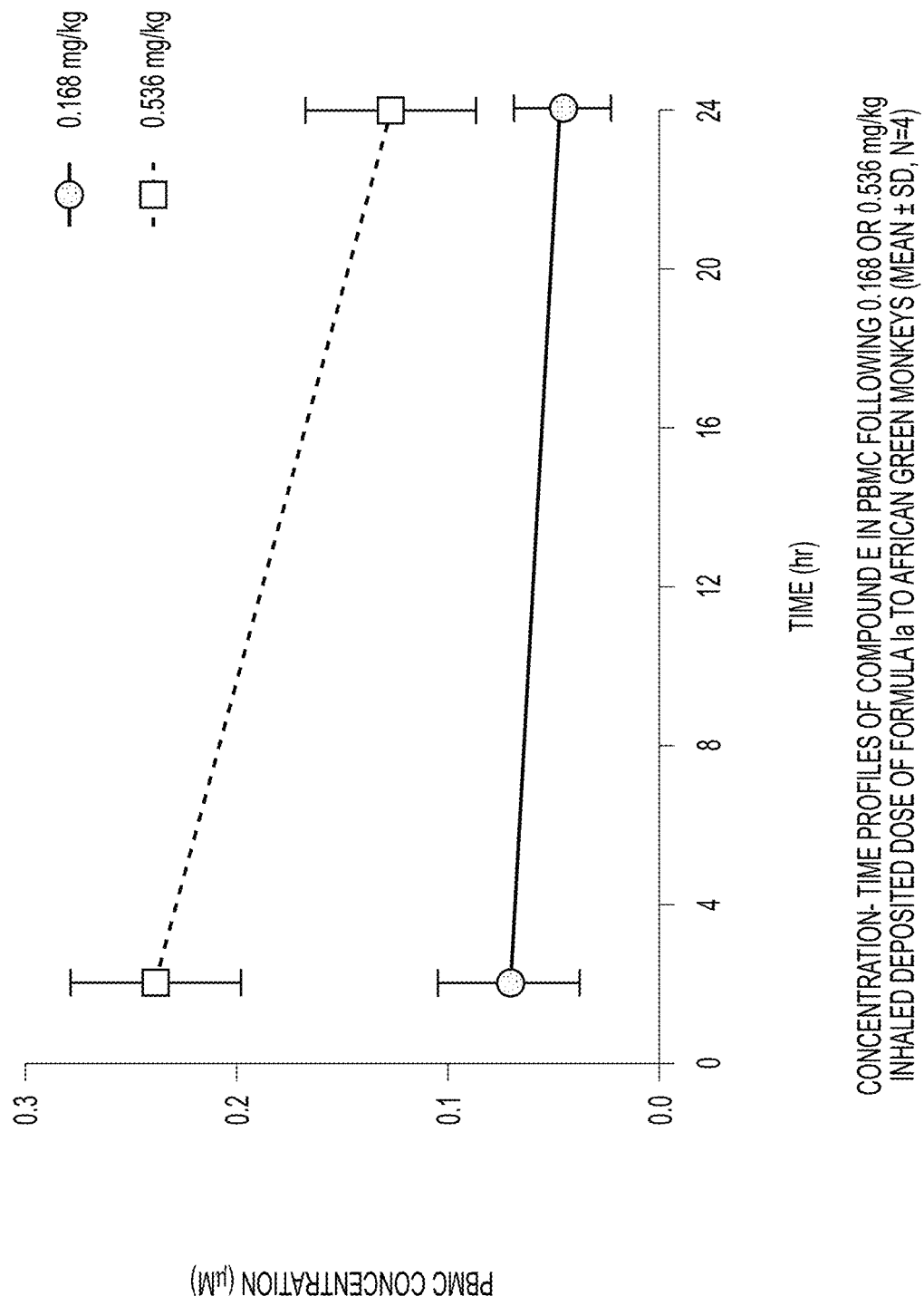

Mean PBMC concentration-time profiles for triphosphate E at 0.168 mg/kg and 0.536 mg/kg dose levels of the compound of Formula Ia are plotted in FIG. 10.

Nasal Mucosa and Nasopharyngeal Mucosa: A qualitative analysis was performed by measuring the LC-MS/MS peak areas for triphosphate E and endogenous ATP in nasal mucosa and nasopharyngeal mucosa. The mucosa contain heterogeneous cell populations and were difficult to characterize; no cell count was performed. Minimal amounts were present in the scrapings and tissue weight could not be measured.

Figure 11:
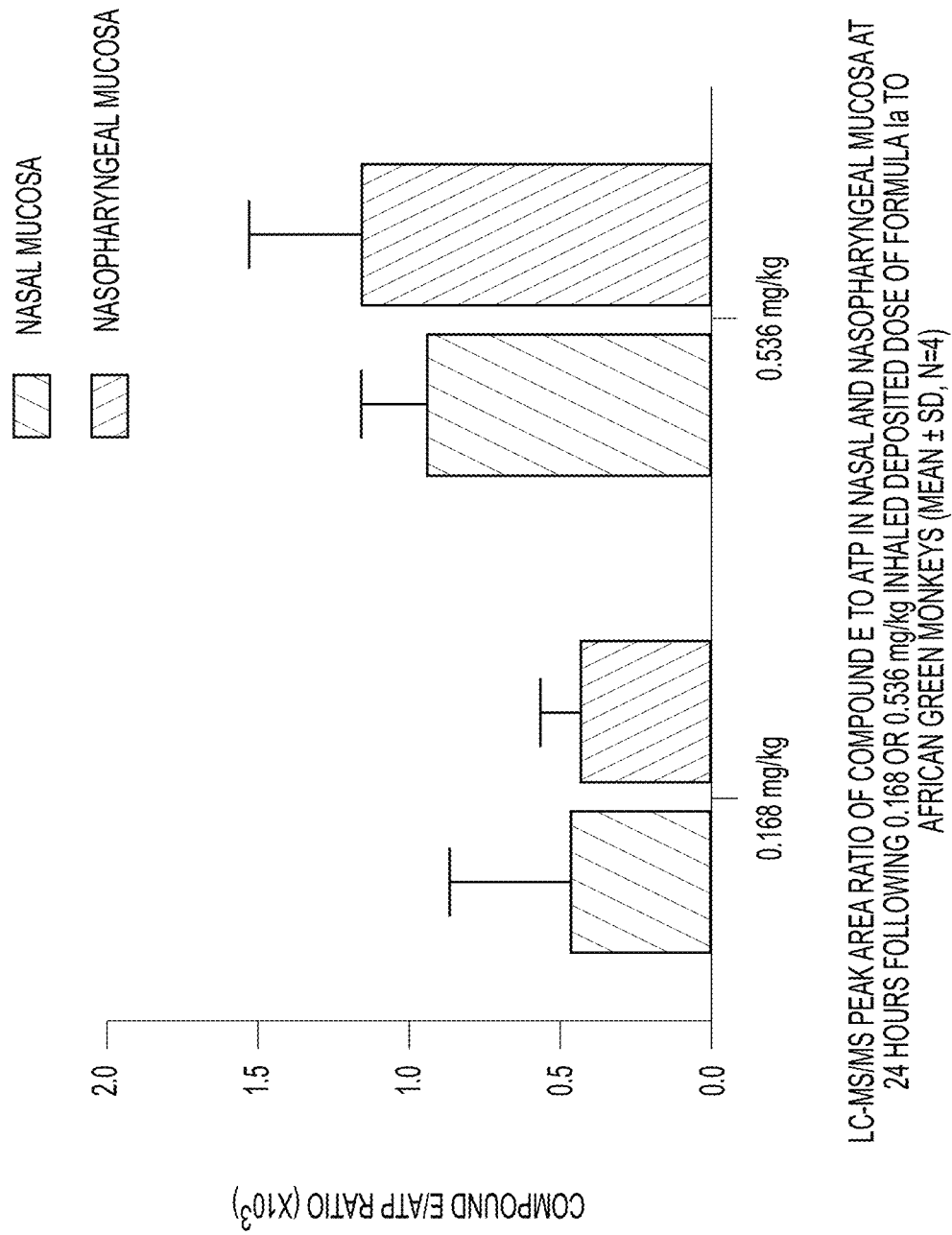

For nasal and nasopharyngeal mucosa, mean peak area ratios of triphosphate E/ATP were determined following both 0.168 mg/kg and 0.536 mg/kg doses of RDV to assess the distribution and activation of RDV into upper respiratory tract. Data are reported in Table 20 and Table 21, respectively, and in FIG. 11.

TABLE 20

LC-MS/MS peak areas of triphosphate E in nasal and nasopharyngeal mucosa at 24 hours following 0.168 mg/kg inhaled deposited dose of the compound of Formula Ia to African Green Monkeys (mean ± SD, n = 4)

| | LC-MS/MS Peak Area | | |
|---|---|---|---|
| Tissue | E Peak Area ($\times 10^5$) | ATP Peak Area ($\times 10^8$) | E/ATP Ratio ($\times 10^3$) |
| Nasal Mucosa | 2.82 ± 2.34 | 6.47 ± 0.40 | 0.455 ± 0.407 |
| Nasopharyngeal Mucosa | 1.93 ± 0.90 | 4.29 ± 0.84 | 0.434 ± 0.131 |

TABLE 21

LC-MS/MS peak areas of triphosphate E in nasal and nasopharyngeal mucosa at 24 hours following 0.536 mg/kg inhaled deposited dose of the compound of Formula Ia to African Green Monkeys (mean ± SD, n = 4)

| | LC-MS/MS Peak Area | | |
|---|---|---|---|
| Tissue | E Peak Area ($\times 10^5$) | ATP Peak Area ($\times 10^8$) | E/ATP Ratio ($\times 10^3$) |
| Nasal Mucosa | 5.29 ± 1.46 | 5.65 ± 0.79 | 0.938 ± 0.222 |
| Nasopharyngeal Mucosa | 4.37 ± 1.72 | 3.69 ± 0.40 | 1.17 ± 0.37 |

Figure 12:
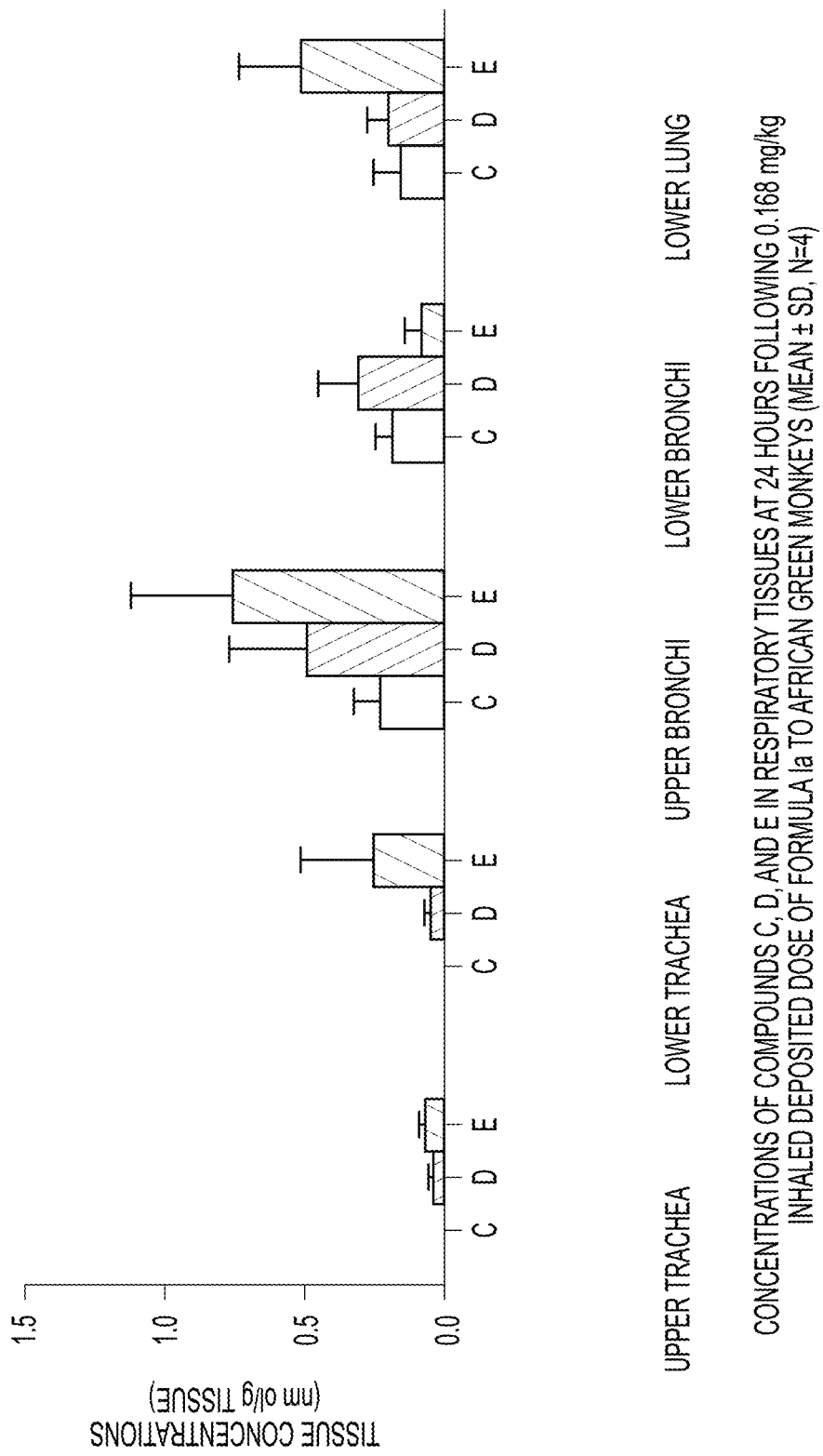
Figure 13:
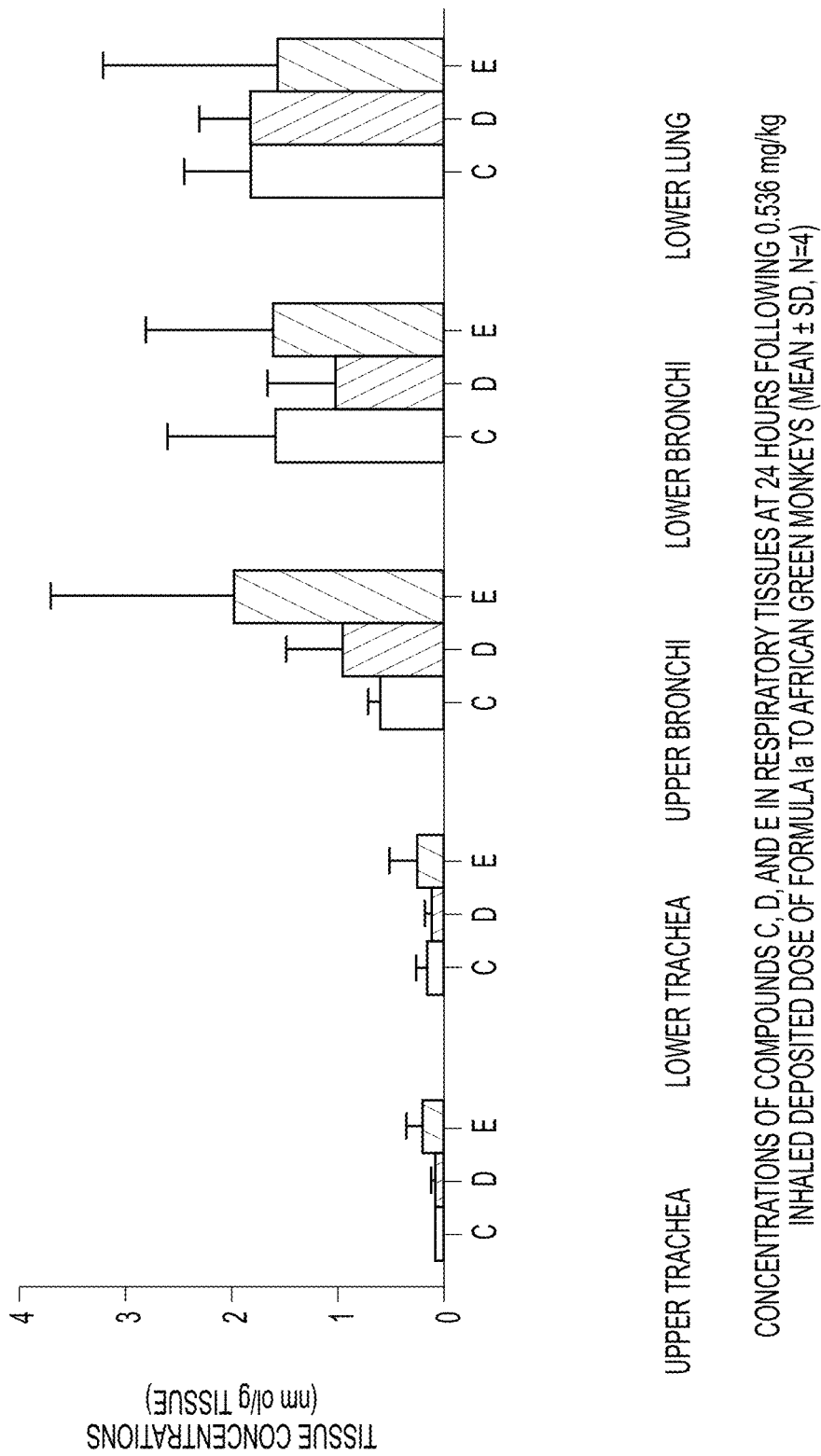

Other Select Tissues: An LC-MS/MS method was used to measure the concentration of the compound of Formula Ia, A, B, C, D, and E in AGM lung, trachea, bronchi, liver and kidney. Liver and kidney were harvested following euthanasia, evidence of increasing lability of phosphorylated metabolites were observed with variable amounts of dephosphorylation appeared to have occurred by the time liver and kidney samples were isolated and flash frozen. Natural nucleotide levels (AMP, ADP, and ATP) in each tissue were also determined in attempts to assess tissue sample integrity. Mean concentrations of the compound of Formula Ia, A, B, C, D, and E at 0.168 mg/kg and 0.536 mg/kg dose levels of RDV in respiratory tissues at 24 hours post dose are reported in Table 22 and Table 23 respectively. Mean concentrations of C, D, and E at 0.168 mg/kg and 0.536 mg/kg dose levels of RDV in respiratory tissues at 24 hours post dose are plotted in in FIG. 12 and FIG. 13, respectively.

TABLE 22

Respiratory Tissue Concentrations of the compound of the compound of Formula Ia, A, B, C, D, and E at 24 hours following 0.168 mg/kg inhaled deposited dose of the compound of Formula Ia to African Green Monkeys (mean ± SD, n = 4)

| Tissue | Formula Ia | A | B | C | D | E | Total Nucleotide |
|---|---|---|---|---|---|---|---|
| Upper Trachea | 0.003 | BLQ | BLQ | BLQ | 0.050 ± 0.013 | 0.069 ± 0.029 | 0.120 ± 0.036 |
| Lower Trachea | 0.002 ± 0.001 | BLQ | BLQ | BLQ | 0.055 ± 0.023 | 0.266 ± 0.251 | 0.146 ± 0.079 |
| Upper Bronchi | BLQ | BLQ | BLQ | 0.235 ± 0.092 | 0.488 ± 0.281 | 0.762 ± 0.360 | 1.49 ± 0.72 |
| Lower Bronchi | 0.002 ± 0.000 | BLQ | BLQ | 0.190 ± 0.062 | 0.314 ± 0.140 | 0.562 ± 0.105 | 1.07 ± 0.10 |
| Lower Lung Lobe | 0.029 ± 0.013 | BLQ | BLQ | 0.164 ± 0.092 | 0.211 ± 0.071 | 0.518 ± 0.225 | 0.852 ± 0.301 |

BLQ: Below Limit of Quantitation. LOQ for A: 0.154 nmol/g tissue; for C: 0.154 nmol/g tissue

TABLE 23

Respiratory tissue concentrations of the compound of Formula Ia, A, B, C, D, and E at 24 hours following 0.536 mg/kg inhaled deposited dose of the compound of Formula Ia to African Green Monkeys (mean ± SD, n = 4)

| Tissue | Formula Ia | A | B | C | D | E | Total Nucleotide |
|---|---|---|---|---|---|---|---|
| Upper Trachea | 0.017 ± 0.017 | BLQ | BLQ | 0.097 ± 0.056 | 0.095 ± 0.041 | 0.208 ± 0.167 | 0.352 ± 0.269 |
| Lower Trachea | 0.028 ± 0.030 | BLQ | BLQ | 0.185 ± 0.124 | 0.114 ± 0.062 | 0.266 ± 0.251 | 0.518 ± 0.437 |
| Upper Bronchi | 0.006 ± 0.004 | BLQ | BLQ | 0.615 ± 0.094 | 0.965 ± 0.520 | 1.99 ± 1.71 | 3.57 ± 2.27 |
| Lower Bronchi | 0.003 ± 0.001 | BLQ | BLQ | 1.58 ± 1.03 | 1.02 ± 0.64 | 1.61 ± 1.20 | 4.21 ± 2.15 |
| Lower Lung Lobe | 0.060 ± 0.017 | BLQ | BLQ | 1.82 ± 0.64 | 1.83 ± 0.49 | 1.58 ± 1.64 | 5.22 ± 0.83 |

Figure 14:
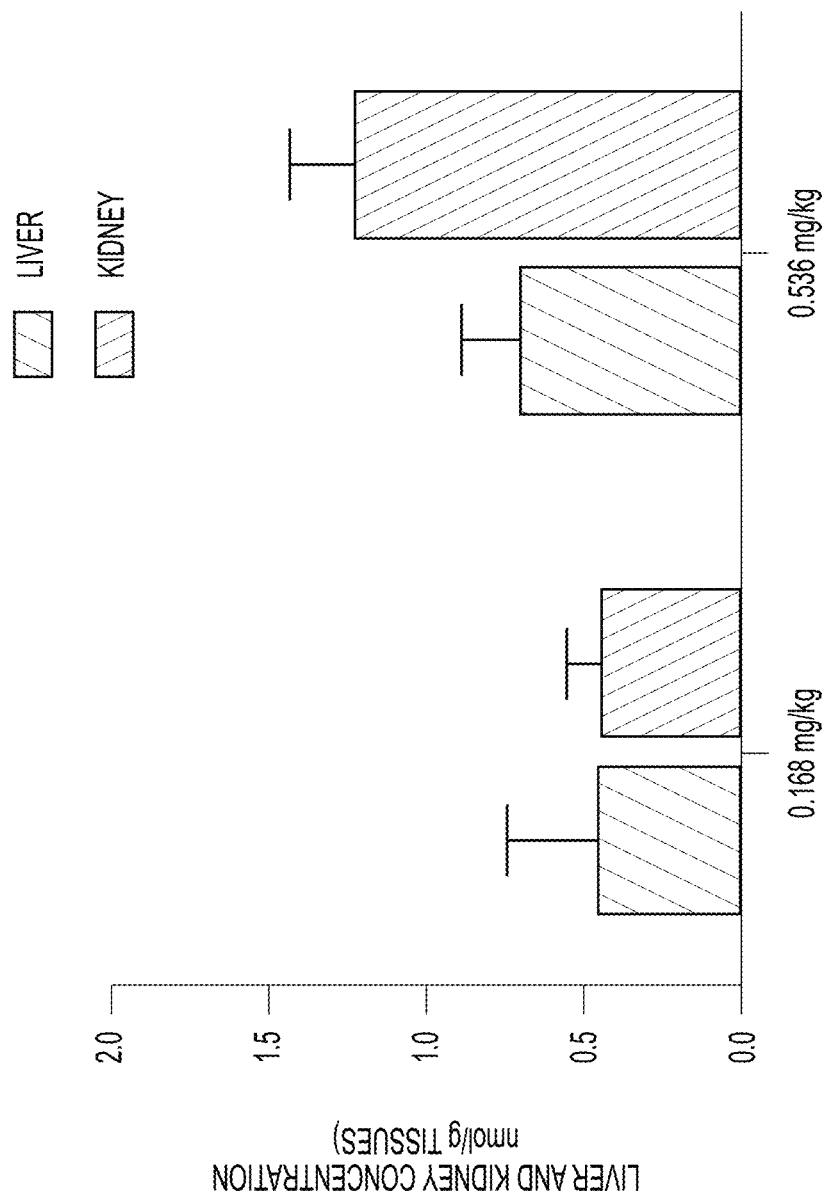
Figure 15:
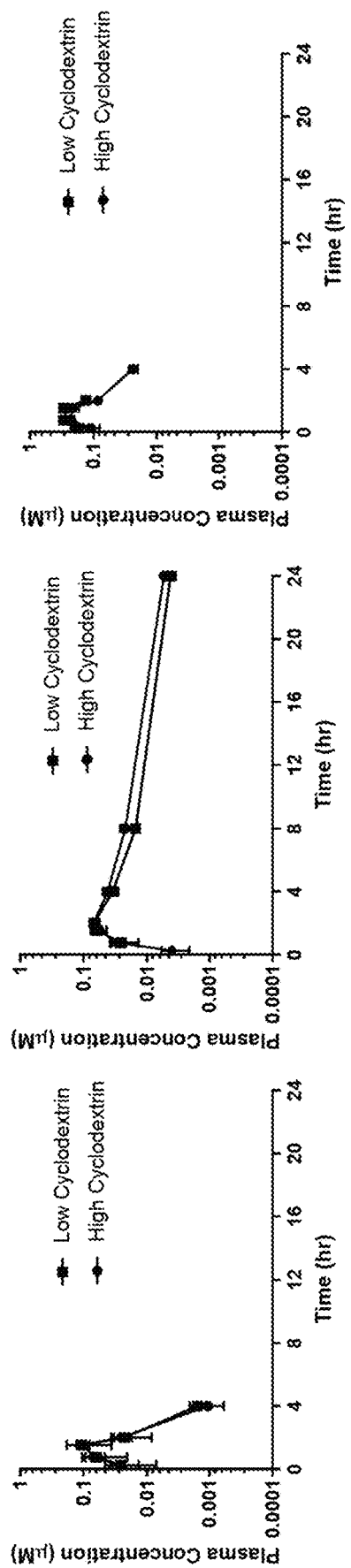
Figure 16:
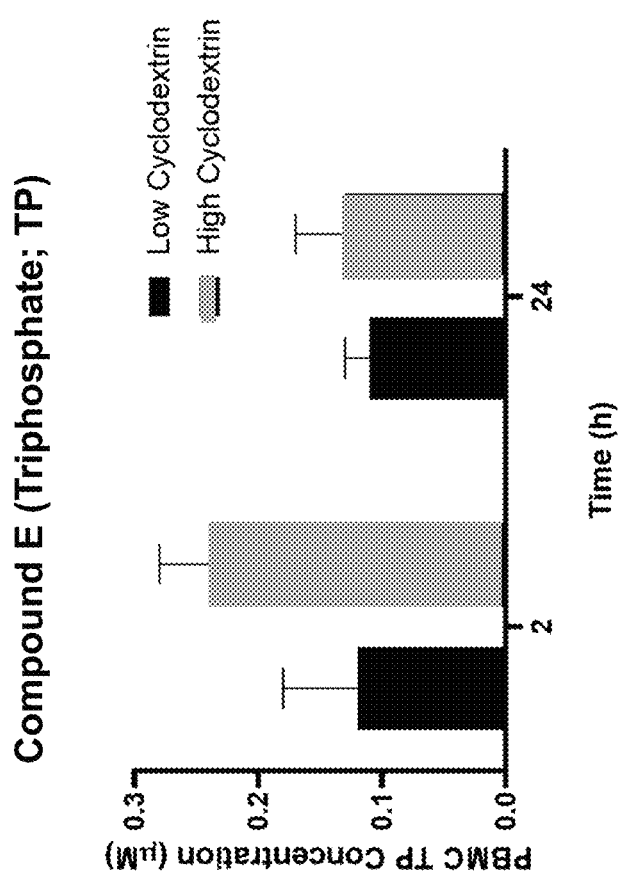
Figure 17:
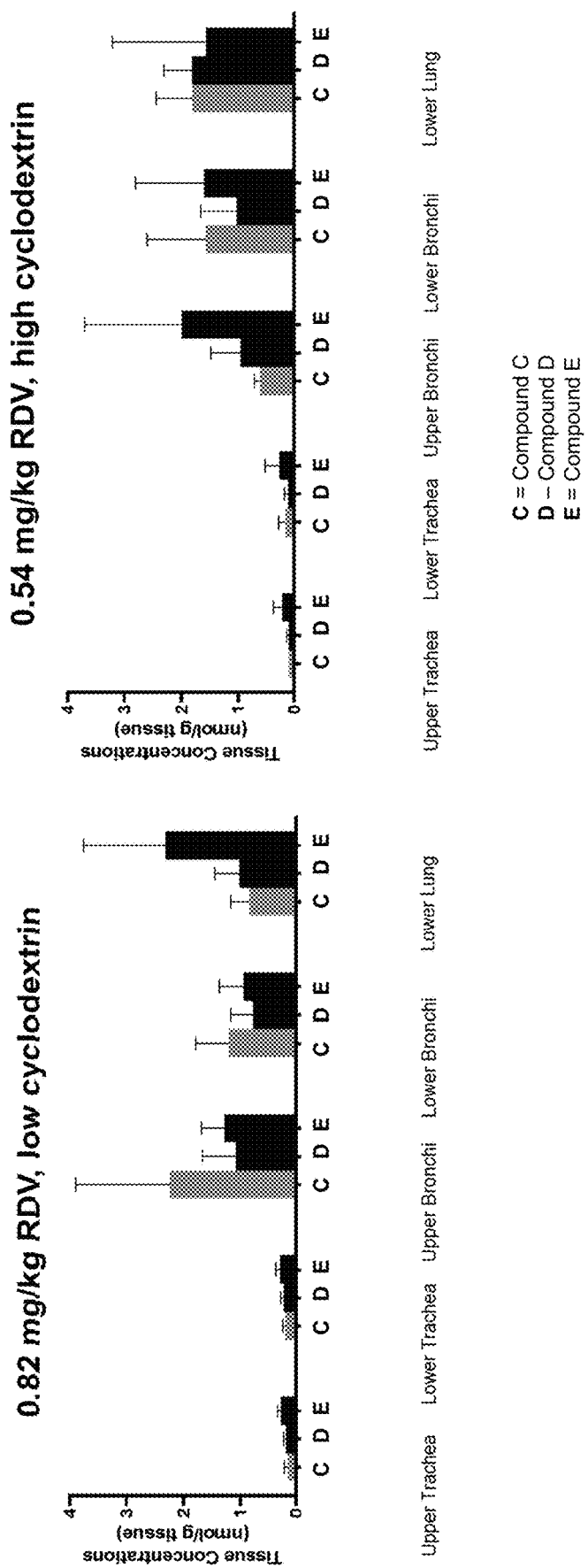
Figure 18:
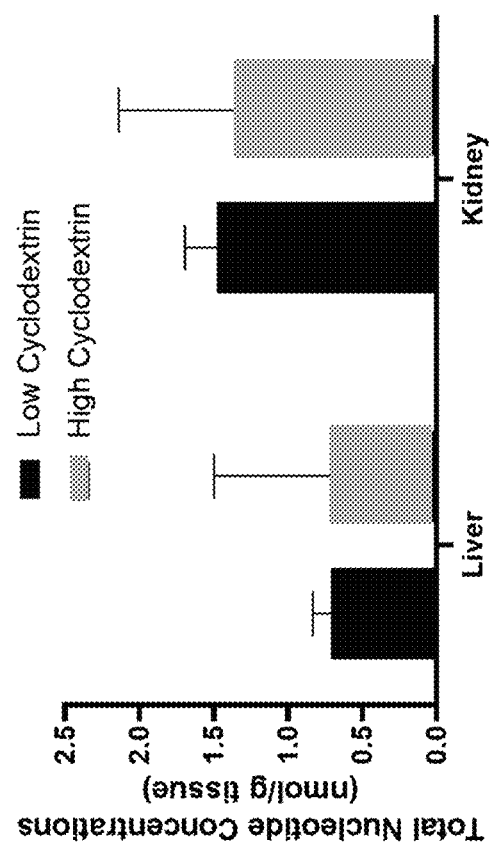

BLQ: Below lower limit of quantitation. For compound A: 0.154 nmol/g tissue; for compound C: 0.154 nmol/g tissue For liver and kidney tissues, mean concentrations of the total metabolite including the compound of Formula Ia, A, B, C, D, and E in these tissues at 0.168 mg/kg and 0.536 mg/kg dose of RDV levels are reported in Table 24 and Table 25, respectively, and shown in FIG. 14.

TABLE 24

Liver and kidney concentrations of the compound of Formula Ia and total nucleotide metabolites at 24 hours following 0.168 mg/kg inhaled deposited dose of the compound of Formula Ia to African Green Monkeys (mean ± SD, n = 4)

| Tissue | Formula Ia (nmol/g tissue) | Total Metabolite Concentrations[a] (nmol/g tissue) |
|---|---|---|
| Liver | 0.003 | 0.446 ± 0.299 |
| Kidney | BLQ | 0.445 ± 0.109 |

BLQ: Below lower limit of quantitation. LOQ for the compound of Formula Ia: 0.002 nmol/g tissue.
[a]Total metabolite includes the compound of Formula Ia, compound A, compound B, compound C, compound D, and compound E.

TABLE 25

Liver and kidney concentrations of the compound of Formula Ia and total nucleotide metabolites at 24 hours following 0.536 mg/kg inhaled deposited dose of RDV to African Green Monkeys (mean ± SD, n = 4)

| Tissue | Formula Ia (nmol/g tissue) | Total Metabolite Concentrations[a] (nmol/g tissue) |
|---|---|---|
| Liver | 0.013 ± 0.016 | 0.695 ± 0.196 |
| Kidney | 0.004 ± 0.001 | 1.23 ± 0.20 |

[a]Total metabolite includes the compound of Formula Ia, compound A, compound B, compound C, compound D, and compound E.

Inhaled compound of Formula Ia distributed into all sections of the respiratory tract as well as other tissues that were collected at 24 h post dose. Efficient formation of triphosphate E was observed in upper trachea, lower trachea, mainstem bronchi and lower bronchi, and lower lung lobe with concentrations of 0.069, 0.266, 0.762, 0.562 and 0.518 nmol/g tissue following the 0.168 mg/kg dose and 0.208, 0.266, 1.99, 1.61 and 1.58 nmol/g tissue following the 0.536 mg/kg dose, respectively. Compounds A, C, D, and E were also observed in liver and kidney with total nucleoside (Compound of Formula Ia, compound A, compound B, compound C, compound D, and compound E) concentrations of 0.446 and 0.445 nmol/g tissue at the 0.168 mg/kg dose and 0.695 and 1.23 nmol/g tissue at the 0.536 mg/kg dose, respectively. Following inhalation of the compound of Formula Ia, triphosphate E was also measured in both nasal and nasopharyngeal mucosa demonstrating distribution of RDV and its activation to the pharmacologically active metabolite in the upper respiratory tract.

Example 17: Intravenous Administration of the Compound of Formula Ia

A pharmacokinetic study following IV administration of the compound of Formula Ia was carried out in African Green Monkeys (AGM). Same Formula Ia formulation as used above in Example 15 was used in these studies (lyophilized powder containing 105 mg of the compound of Formula Ia (3.23% w/w) and 3146 mg of sulfobutylether-β-cyclodextrin sodium Salt (SBECD, Betadex Sulfobutyl Ether Sodium; 96.77% w/w) reconstituted with 19 mL of water for injection to obtain a solution of 5 mg/mL the compound of Formula Ia and 150 mg/mL SBECD at pH 3.6 (range of 3.0-4.0)). The results of this study are shown in Table 26 below.

TABLE 26

IV administration of the compound of Formula Ia

| Tissue | 10 mg/kg IV AGM |
|---|---|
| Formula Ia AUC$_{0-t}$ (μM · h) | 7.26 |
| B AUC$_{0-t}$ (μM · h) | 9.47 |
| A AUC$_{0-t}$ (μM · h) | 9.06 |
| PBMC TP (E) (μM) | 7.54 |
| Lung TP (nmol/g tissue) | 1.03 |
| Upper Trachea TP (nmol/g tissue) | 0.54 |
| Lower Trachea TP (nmol/g tissue) | 0.53 |
| Upper Bronchi TP (nmol/g tissue) | 0.81 |
| Lower Bronchi TP (nmol/g tissue) | 1.12 |
| Liver metabolite (nmol/g tissue) | 17.3 |
| Kidney metabolite (nmol/g tissue) | 39.8 |

Example 18: PBMC (Peripheral Blood Mononuclear Cell) In-Vitro Intracellular Triphosphate Formation Assay In-vitro intracellular triphosphate formation is measured for the compound of Formula I, Formula Ia, or Formula Ib using the following protocol. Freshly-isolated PBMC's are derived from a healthy donor and are suspended to a concentration of 5 million cells/mL in culture medium (RPMI 1164 containing L-glutaimine) prior to the start of the experiment. 10 mL aliquots of PBMCs are transferred to 50 mL conical tubes with loosened caps and compounds are added to a final concentration of 2 μM. 1 mL aliquots are then transferred to the wells of a 24-well plate per sample. The PBMC-compound mixtures are incubated for 2 hours at 37° c./5% CO$_2$ under gentle agitation. Following incubation, PBMCs are spun at 5000 RPM for 3 min and supernatants are aspirated without disturbing the cell pellet. For samples undergoing immediate analysis, samples are resuspended in pre-cooled 1× Tris-buffered saline and are transferred to 1.5 mL conical tubes containing 0.5 mL of nyosil M25. Samples/Oil aliquots are then spun for 1 min at 13,000 RPM. Following centrifugation, all media is aspirated from the tubes without disturbing the oil layer. Water is added on top of the oil layer and the spinning/aspiration process is repeated followed by an additional water wash. After the second wash step, all oil and water is removed and the cell pellet is snap frozen on dry ice and stored at −80° C. until further processing. Samples not undergoing immediate analysis are washed 2× with serum-free culture medium, resuspended in 1 mL of culture medium and incubated at 37c/5% CO$_2$ until they were processed by the aforementioned protocol. Each PBMC sample is treated with 500 μL of dry ice-cold extraction buffer (70% methanol, containing 0.5 μM chloro-adenosine triphosphate as internal standard). The above solution is vortexed for 5 minutes, then centrifuged at 20,000×g for 20 minutes. Supernatant is transferred to clean 1.5 mL eppendorf vials and loaded onto a centrifuging evaporator. Once dry, samples are reconstituted with 80 μL of mobile phase A, centrifuged at 20,000×g for 20 minutes and supernatants transferred to HPLC injection vials for analysis. An aliquot of 10 μL is injected into a Sciex 6500 LC/MS/MS system. Standard calibration curves for PBMC are constructed based on pmol of compound per sample. The value from each sample is then divided by the total number of cells in the sample to yield pmol per million cells. Micromolar concentrations are then derived using an intracellular volume of 0.2 pL per cell.

Example 19: Animal Pharmacokinetics Assay

Animal PK studies for the compound of Formula I, Formula Ia, or Formula Ib are conducted using the following protocol. Animals weighing 3 to 6 kg are used for the in-life portion of the studies. Test articles are dosed to male Cynomolgus monkeys via inhalation. Plasma samples are collected at 0.25, 0.5, 1, 1.5 2, 4, 8, and 24 hr post-administration and PBMC samples are collected at 2 and 24 hr post-administration.

Blood samples (approximately 1 mL) are collected into pre-chilled collection tubes containing K2EDTA and are centrifuged at 4° C. to separate plasma. For PBMC collection, approximately 8 mL of blood samples are collected at room temperature into CPT vacutainer tubes containing sodium heparin for isolation. At each terminal collection, animals are anesthetized and lungs are harvested while animals are alive. Collected lungs are flash-frozen in liquid nitrogen immediately following removal.

The plasma samples from pharmacokinetic studies are subject to protein precipitation by addition of acetonitrile to final concentrations of 75% containing 5-iodotubericidin as internal standards. Analytes in plasma samples are separated on a 4 μm 150×2 mm Synergi Max-RP column (Phenomenex, Torrance, Calif.) using mobile phase containing 0.2% formic acid and a linear gradient from 2% to 100% acetonitrile at a flow rate of 250 μL/min over 7 min. Eight points standard curves are prepared in blank plasma covered concentrations from 5.1 to 5000 nM and show linearity in excess of an R2 value of 0.99. Separately prepared quality control samples of 120 and 3,000 nM in plasma are analyzed at the beginning and end of each sample set to ensure accuracy and precision within 20%.

Each PBMC sample is treated with 500 μL of extraction buffer containing 67 mM ethylenediamine tetraacetic acid (EDTA) in 70% methanol, with 0.5 μM chloro-adenosine triphosphate as internal standard. The extraction buffer is cooled on dry ice. The above solution was vortexed for 5 minutes, then centrifuged at 20,000×g for 20 minutes. Supernatant is transferred to clean 1.5 mL eppendorf vials and loaded onto a centrifuging evaporator. Once dry, samples are reconstituted with 80 μL of 1 mM ammonium phosphate buffer (pH=7), centrifuged at 20,000×g for 20 minutes and supernatants transferred to HPLC injection vials for analysis. An aliquot of 10 μL is injected into an API 5000 LC/MS/MS system. In order to calculate intracellular concentration of metabolites, the total number of cells in each sample is determined using total DNA counting methods (Benech, et al. Peripheral Blood Mononuclear Cell Counting Using a DNA-detection-based Method. 2004 Jul. 1; 330 (1): 172-4). Standard calibration curves for PBMC are constructed based on pmol of compound per sample. The value from each sample is then divided by the total number of cells in the sample to yield pmol per million cells. Micromolar concentrations are then derived using an intracellular volume of 0.2 pL per cell.

Lung samples are prepared by sectioning into smaller pieces and distributing into pre-weighed 15 mL conical tubes, which are kept on dry ice. The ice-cold extraction buffer (0.1% KOH and 67 mM ethylenediamine tetraacetic acid in 70% methanol containing 0.5 μM chloro-adenosine triphosphate as the internal standard, ~2 mL) is added into ~0.5 g of each lung sample. The mixtures are promptly homogenized using an Omni-Tip TH™ with disposable, hard tissue homogenizer probes (Omni International). Aliquots of the homogenate are filtered by using 0.2 μm 96-well polypropylene filter plate (Varian Captiva™). The filtrates are evaporated to dryness and reconstituted with an equal volume of 1 mM ammonium phosphate buffer (pH=7) prior to LC-MS/MS analysis.

The nucleoside triphosphate quantification used ion pairing nucleotide detection LC-MS/MS method. Analytes are separated by a 2.5 μm 2.0×50 mm Luna C18 column (Phenomenex, Torrance, Calif.) using an ion pairing buffer containing 3 mM ammonium phosphate (pH 5) with 10 mM dimethylhexylamine (DMH) and a multistage linear gradient from 10% to 50% acetonitrile at a flow rate of 160 μL/min over 11 min. Seven points standard curves prepared in blank matrices covered concentrations from 24.0 to 17,500 nM and showed linearity in excess of an $R^2$ value of 0.99.

Example 20: Comparative Studies of Representative Cyclodextrin Solution Formulations and HPMC Suspension Formulation of the Compound of Formula Ia Exemplary formulations were prepared as described above and PK studies in AGM monkeys were conducted using the following study designs:

| Group | Route | # of Animals | Target Presented Dose (mg/kg) | Target Deposited Dose (mg/kg) | Measured Deposited Dose (mg/kg) | Exposure Time (min) |
|---|---|---|---|---|---|---|
| Formulation 1: Low cyclodextrin (75 mg/mL) | Head dome inhalation | 3 | 2.2 | 0.55 | 0.82 ± 0.08 | 90 |
| Formulation 2: 0.1% HPMC suspension | Head dome inhalation | 3 | 3.6 | 0.9 | 0.72 ± 0.03 | 10 |
| Formulation 3: High cyclodextrin (150 mg/mL) | Head dome inhalation | 4 | 3.5 | 0.88 | 0.54 ± 0.10 | 90 |

The results of these experiments are presented in FIGS. 15-24 and Tables 27-36 below.

TABLE 27

PK profile of formulations 1 and 3.

| | PK Parameter | | | | | |
|---|---|---|---|---|---|---|
| | Formulation 1 | | | Formulation 3 | | |
| Time (h) | Formula Ia | Compound B | Compound A | Formula Ia | Compound B | Compound A |
| $C_{max}$ (μM) | 0.11 ± 0.07 | 0.29 ± 0.07 | 0.07 ± 0.01 | 0.10 ± 0.02 | 0.23 ± 0.03 | 0.07 ± 0.01 |
| $T_{max}$ (h) | 1.52 ± 0.00 | 1.26 ± 0.45 | 2.00 ± 0.00 | 1.53 ± 0.00 | 0.95 ± 0.39 | 2.00 ± 0.00 |
| $AUC_{0-24}$ (μM · h) | 0.15 ± 0.10 | 0.45 ± 0.09 | 0.44 ± 0.06 | 0.15 ± 0.05 | 0.42 ± 0.05 | 0.54 ± 0.08 |
| $T_{1/2}$ (h) | 0.35 ± 0.08 | 0.71 ± 0.31 | 7.09 ± 1.03 | 0.34 ± 0.10 | 0.89 ± 0.16 | 7.10 ± 0.36 |

TABLE 28

PBMC triphosphate (compound E; TP) levels for formulations 1 and 3.

| Time (h) | PBMC TP (Compound E) Levels (mM) | |
|---|---|---|
| | Formulation 1 | Formulation 3 |
| 2 | 0.12 ± 0.06 | 0.24 ± 0.04 |
| 24 | 0.11 ± 0.02 | 0.13 ± 0.04 |

TABLE 29

Respiratory tissue levels of compounds C, D, and E for formulations 1 and 3.

| | Formulation 1 | | | | | Formulation 3 | | | | |
|---|---|---|---|---|---|---|---|---|---|---|
| | Upper trachea | Lower trachea | Upper branchi | Lower branchi | Lower lung | Upper trachea | Lower trachea | Upper branchi | Lower branchi | Lower lung |
| MP | 0.21 ± 0.05 | 0.22 ± 0.04 | 2.11 ± 1.52 | 1.15 ± 0.54 | 0.81 ± 0.30 | 0.10 ± 0.06 | 0.19 ± 0.12 | 0.62 ± 0.09 | 1.58 ± 1.03 | 1.82 ± 0.64 |
| DP | 0.20 ± 0.03 | 0.23 ± 0.05 | 1.08 ± 0.58 | 0.76 ± 0.41 | 1.02 ± 0.43 | 0.10 ± 0.04 | 0.11 ± 0.06 | 0.97 ± 0.52 | 1.02 ± 0.64 | 1.83 ± 0.49 |
| TP | 0.27 ± 0.06 | 0.29 ± 0.07 | 1.28 ± 0.40 | 0.94 ± 0.43 | 2.32 ± 1.44 | 0.21 ± 0.17 | 0.27 ± 0.25 | 1.99 ± 1.71 | 1.61 ± 1.20 | 1.58 ± 1.64 |

MP = Compound C; DP = Compound D; TP = Compound E.

TABLE 30

Total nucleotides levels in liver and kidney at 24 hours with formulations 1 and 3.

| | Liver and Kidney Total Nucleotide Levels at 24 h post-dose (nmol/g tissue) | |
|---|---|---|
| Tissue | Formulation 1 | Formulation 3 |
| Liver | 0.71 ± 0.13 | 0.70 ± 0.20 |
| Kidney | 1.48 ± 0.21 | 1.23 ± 0.20 |

TABLE 31

Mucosal Samples: Compound E/ATP Ratio for formulations 1 and 3.

| | Mucosa TP/ATP Ratios at 24 h post-dose | |
|---|---|---|
| Tissue | Formulation 1 | Formulation 3 |
| Nasal Mucosa | 0.053 ± 0.038 | 0.940 ± 0.222 |
| Nasopharyngeal Mucosa | 0.119 ± 0.040 | 1.67 ± 0.37 |

TABLE 32

Plasma PK of formulations 1 and 2.

| | PK Parameter | | | | | |
|---|---|---|---|---|---|---|
| | Formulation 1 | | | Formulation 2 | | |
| Time (h) | Formula Ia | Compound B | Compound A | Formula Ia | Compound B | Compound A |
| $C_{max}$ (μM) | 0.11 ± 0.07 | 0.29 ± 0.07 | 0.07 ± 0.01 | 0.04 ± 0.03 | 0.30 ± 0.10 | 0.03 ± 0.02 |
| $T_{max}$ (h) | 1.52 ± 0.00 | 1.26 ± 0.45 | 2.00 ± 0.00 | 0.18 ± 0.00 | 0.50 ± 0.00 | 1.33 ± 0.58 |
| $AUC_{0-24}$ (μM·h) | 0.15 ± 0.10 | 0.45 ± 0.09 | 0.44 ± 0.06 | 0.09 ± 0.10 | 0.71 ± 0.43 | 0.37 ± 0.35 |
| $T_{1/2}$ (h) | 0.35 ± 0.08 | 0.71 ± 0.31 | 7.09 ± 1.03 | 1.39 ± 0.63 | 2.97 ± 1.59 | 9.66 ± 0.78 |

TABLE 33

PBMC metabolite levels for formulations 1 and 2.

| Time | PBMC TP (Compound E) Levels (mM) | |
|---|---|---|
| (h) | Formulation 1 | Formulation 2 |
| 2 | 0.12 ± 0.06 | 0.11 ± 0.02 |
| 24 | 0.11 ± 0.02 | 0.09 ± 0.04 |

TABLE 34

Respiratory tissues metabolite levels for formulations 1 and 2.

| | Formulation 1 | | | | | Formulation 2 | | | | |
|---|---|---|---|---|---|---|---|---|---|---|
| | Upper trachea | Lower trachea | Upper branchi | Lower branchi | Lower lung | Upper trachea | Lower trachea | Upper branchi | Lower branchi | Lower lung |
| MP | 0.21 ± 0.05 | 0.22 ± 0.04 | 2.11 ± 1.52 | 1.15 ± 0.54 | 0.81 ± 0.30 | <0.15 | <0.15 | 0.59 ± 0.27 | 0.79 ± 0.64 | 0.93 ± 0.53 |
| DP | 0.20 ± 0.03 | 0.23 ± 0.05 | 1.08 ± 0.58 | 0.76 ± 0.41 | 1.02 ± 0.43 | <0.15 | <0.15 | 0.39 ± 0.08 | 0.53 ± 0.25 | 1.18 ± 0.20 |
| TP | 0.27 ± 0.06 | 0.29 ± 0.07 | 1.28 ± 0.40 | 0.94 ± 0.43 | 2.32 ± 1.44 | <0.15 | <0.15 | 0.55 ± 0.13 | 0.71 ± 0.40 | 2.51 ± 0.33 |

MP = Compound C; DP = Compound D; TP = Compound E.

TABLE 35

Total nucleotides levels in liver and kidney at 24 hours following inhalation administration of formulations 1 and 2.

| | Liver and Kidney Total Nucleotide Levels at 24 h post-dose (nmol/g tissue) | |
|---|---|---|
| Tissue | Formulation 1 | Formulation 2 |
| Liver | 0.71 ± 0.13 | 0.71 ± 0.79 |
| Kidney | 1.48 ± 0.21 | 1.36 ± 0.78 |

TABLE 36

Mucosal Samples: GS-443902/ATP Ratio for formulations 1 and 2.

| | Mucosa TP/ATP Ratios at 24 h post-dose | |
|---|---|---|
| Tissue | Formulation 1 | Formulation 2 |
| Nasal Mucosa | 0.053 ± 0.038 | 0.013 ± 0.005 |
| Nasopharyngeal Mucosa | 0.119 ± 0.040 | 0.016 ± 0.007 |

As seen, equivalent plasma PK profiles and triphosphate levels in tissues and PBMC were seen between formulations 1 and 3 in AGM.

Further, while Formula Ia was cleared slower with the suspension formulation (formulation 2), the plasma exposures were similar to the solution formulation (formulation 1). In general, tissues and PBMC levels were similar between the formulations 1 and 2. The suspension formulation 2 achieved similar PK profiles to the solution formulation 1 at significantly shorter exposure duration (10 vs. 90 min).

Example 21. Nebulizer Performance Data of an Exemplary Formulation

Aqueous solution containing 5 mg/mL Formula Ia, 15% w/v SBECD at an 8 mL charge was nebulized by the PARI Vios® PRO Aerosol Delivery System (PART LC® Sprint jet nebulizer coupled with a PARI Vios® PRO compressor; hereon referred to as the LC® Sprint) until the end of nebulization. No significant change in -continued Formula Ib

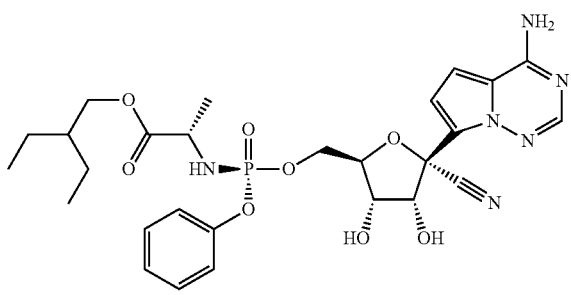

or a pharmaceutically acceptable salt thereof;
ii. water; and
iii. cyclodextrin;
wherein the pharmaceutical formulation is administered to the human via inhalation.

2. The method of claim 1, wherein the method comprises administering to the human at least one additional therapeutic agent.

3. The method of claim 1, wherein the viral infection is a coronavirus infection.

4. The method of claim 1, wherein the viral infection is SARS-CoV-2 infection (COVID-19).

5. The method of claim 1, wherein the viral infection is a SARS virus infection.

6. The method of claim 1, wherein the viral infection is a MERS virus infection.

7. The method of claim 1, wherein the viral infection is a pneumoviridae virus infection.

8. The method of claim 1, wherein the viral infection is a picornaviridae virus infection.

9. The method of claim 1, wherein the viral infection is a flaviviridae virus infection.

10. The method of claim 1, wherein the viral infection is a Filoviridae virus infection.

11. The method of claim 1, wherein the viral infection is an orthomyxovirus infection.

12. The method of claim 11, wherein the viral infection is an influenza virus infection.

13. The method of claim 1, wherein the viral infection is a paramyxoviridae virus infection.

14. The method of claim 1, wherein the pharmaceutical formulation comprises:
i. the compound of Formula Ia:

Formula Ia

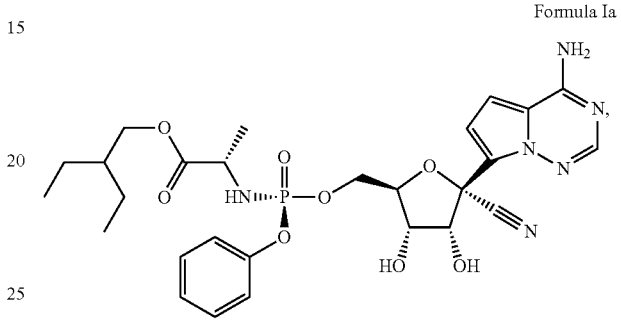

or a pharmaceutically acceptable salt thereof;
ii. water; and
iii. cyclodextrin.

15. The method of claim 14, wherein the viral infection is SARS-CoV-2 infection (COVID-19).

16. The method of claim 7, wherein the pneumoviridae virus infection is respiratory syncytial virus infection.

* * * * *

UNITED STATES PATENT AND TRADEMARK OFFICE
CERTIFICATE OF CORRECTION

PATENT NO. : 11,701,372 B2
APPLICATION NO. : 17/222125
DATED : July 18, 2023
INVENTOR(S) : Scott Ellis et al.

Page 1 of 1

It is certified that error appears in the above-identified patent and that said Letters Patent is hereby corrected as shown below:

On the Title Page

Other Publications
Column 2, Line 1, delete "Dmg" and insert -- Drug --.

In the Claims

Column 98, Lines 40-52, Claim 1, delete " 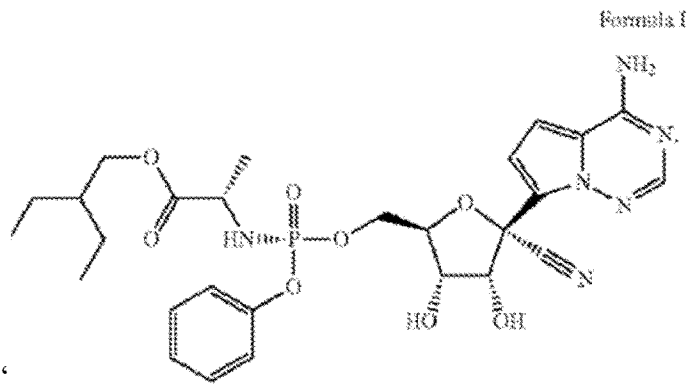 "

and insert -- 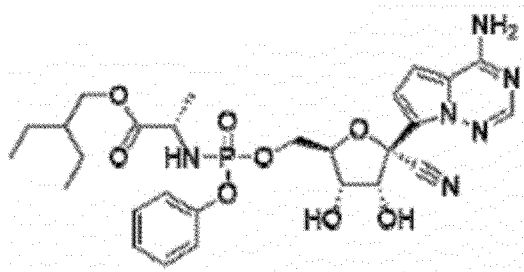 --.

Column 100, Line 2, Claim 10, delete "Filoviridae" and insert -- filoviridae --.

Signed and Sealed this
Eighteenth Day of June, 2024

Katherine Kelly Vidal
*Director of the United States Patent and Trademark Office*